US006500621B2

(12) United States Patent
Köster

(10) Patent No.: US 6,500,621 B2
(45) Date of Patent: *Dec. 31, 2002

(54) DNA DIAGNOSTICS BASED ON MASS SPECTROMETRY

(75) Inventor: Hubert Köster, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/796,416

(22) Filed: Feb. 28, 2001

(65) Prior Publication Data

US 2002/0137046 A1 Sep. 26, 2002

Related U.S. Application Data

(63) Continuation of application No. 09/495,444, filed on Jan. 31, 2000, now Pat. No. 6,300,076, and a continuation of application No. 09/504,245, filed on Feb. 15, 2000, now Pat. No. 6,221,605, application No. 09/796,416, which is a continuation of application No. 09/287,679, filed on Apr. 6, 1999, now Pat. No. 6,258,538, and a continuation of application No. 08/617,256, filed on Mar. 18, 1996, now Pat. No. 6,043,031, and a continuation-in-part of application No. 08/406,199, filed on Mar. 17, 1995, now Pat. No. 5,605,798.

(51) Int. Cl.[7] .............................. C12Q 1/68; C12P 19/34
(52) U.S. Cl. .............................. 435/6; 435/91.2; 436/94
(58) Field of Search ................. 435/6, 91.2; 436/94

(56) References Cited

U.S. PATENT DOCUMENTS

| | | | |
|---|---|---|---|
| 4,214,159 A | 7/1980 | Hillenkamp et al. | 250/288 |
| 4,442,354 A | 4/1984 | Hurst et al. | 250/281 |
| 4,683,195 A | 7/1987 | Mullis et al. | 435/6 |
| 4,725,677 A | 2/1988 | Köster et al. | 536/27 |
| 4,733,073 A | 3/1988 | Becker et al. | 250/288 |
| 4,778,993 A | 10/1988 | Waugh | 250/287 |
| 4,920,264 A | 4/1990 | Becker | 250/282 |

(List continued on next page.)

FOREIGN PATENT DOCUMENTS

| | | |
|---|---|---|
| DE | 4431174 | 3/1996 |
| DE | 4438630 | 5/1996 |
| EP | 0269520 | 6/1988 |
| EP | 0360677 | 3/1990 |
| EP | 0412883 | 2/1991 |

(List continued on next page.)

OTHER PUBLICATIONS

Adler et al. "Cell Membrane Coating with Glutaraldehyde: Application to a versatile Solid–Phase Assay for Thyroid Membrane Proteins and Molecules Interacting with Thyroid Membranes," *Analytical Chemistry* 148:320–327 (1985).

Andersen, et al., Electrospray ionization and matrix assisted laser desorption/ionization mass spectrometry: Powerful analytical tools in recombinant protein chemistry, *Nature Biotech.* 14: 449–457 (1996).

(List continued on next page.)

*Primary Examiner*—Kenneth R. Horlick

(57) ABSTRACT

Fast and highly accurate mass spectrometry-based processes for detecting particular nucleic acid molecules and sequences in the molecules are provided. Depending upon the sequence to be detected, the processes, for example, can be used to diagnose a genetic disease or a chromosomal abnormality, a predisposition to a disease or condition, or infection by a pathogen, or for determining identity or heredity.

21 Claims, 57 Drawing Sheets

U.S. PATENT DOCUMENTS

| | | | |
|---|---|---|---|
| 5,003,059 A | 3/1991 | Brennan | 536/27 |
| 5,045,694 A | 9/1991 | Beavis et al. | 250/287 |
| 5,059,654 A | 10/1991 | Hou et al. | 525/54.1 |
| 5,062,935 A | 11/1991 | Schlag et al. | 204/157.41 |
| 5,064,754 A | 11/1991 | Mills | 435/6 |
| 5,118,605 A | 6/1992 | Urdea | 435/6 |
| 5,118,937 A | 6/1992 | Hillenkamp et al. | 250/282 |
| 5,135,870 A | 8/1992 | Williams | 436/173 |
| 5,143,854 A | 9/1992 | Pirrung et al. | 436/518 |
| 5,149,625 A | 9/1992 | Church et al. | 435/6 |
| 5,202,561 A | 4/1993 | Giessmann et al. | 250/281 |
| 5,210,412 A | 5/1993 | Levis et al. | 250/288 |
| 5,237,016 A | 8/1993 | Ghosh et al. | 525/329.4 |
| 5,288,644 A | 2/1994 | Beavis et al. | 436/94 |
| 5,364,760 A | 11/1994 | Chu et al. | 435/6 |
| 5,373,156 A | 12/1994 | Franzen | 250/288 |
| 5,376,788 A | 12/1994 | Standing et al. | 250/287 |
| 5,380,833 A | 1/1995 | Urdea | 536/22.1 |
| 5,381,008 A | 1/1995 | Tanner et al. | 250/288 |
| 5,382,793 A | 1/1995 | Weinberger et al. | 250/288 |
| 5,399,857 A | 3/1995 | Doroshenko et al. | 250/292 |
| 5,403,711 A | 4/1995 | Walder et al. | 435/6 |
| 5,422,253 A | 6/1995 | Dahlberg et al. | 435/91.53 |
| 5,436,327 A | 7/1995 | Southern et al. | 536/25.34 |
| 5,459,039 A | 10/1995 | Modrich et al. | 435/6 |
| 5,474,895 A | 12/1995 | Ishii et al. | 435/6 |
| 5,478,893 A | 12/1995 | Ghosh et al. | 525/329.4 |
| 5,503,980 A | 4/1996 | Cantor | 435/6 |
| 5,508,169 A | 4/1996 | Deugau et al. | 435/6 |
| 5,510,270 A | 4/1996 | Fodor et al. | 436/518 |
| 5,510,613 A | 4/1996 | Reilly et al. | 250/287 |
| 5,512,439 A | 4/1996 | Hornes et al. | 435/6 |
| 5,541,311 A | 7/1996 | Dahlberg et al. | 536/23.7 |
| 5,547,835 A | 8/1996 | Köster | 435/6 |
| 5,580,733 A | 12/1996 | Levis et al. | 435/6 |
| 5,605,798 A | 2/1997 | Köster | 435/6 |
| 5,608,889 A | 3/1997 | Werlinger et al. | 395/421.07 |
| 5,614,402 A | 3/1997 | Dahlberg et al. | 435/199 |
| 5,622,824 A | 4/1997 | Köster | 435/6 |
| 5,624,711 A | 4/1997 | Sundberg et al. | 427/261 |
| 5,625,184 A | 4/1997 | Vestal et al. | 250/287 |
| 5,627,369 A | 5/1997 | Vestal et al. | 250/287 |
| 5,631,134 A | 5/1997 | Cantor | 435/6 |
| 5,641,959 A | 6/1997 | Holle et al. | 250/287 |
| 5,643,798 A | 7/1997 | Beavis et al. | 436/94 |
| 5,650,489 A | 7/1997 | Lam et al. | 530/334 |
| 5,654,545 A | 8/1997 | Holle et al. | 250/287 |
| 5,663,242 A | 9/1997 | Ghosh et al. | 525/329.4 |
| 5,688,642 A | 11/1997 | Chrisey et al. | 435/6 |
| 5,691,141 A | 11/1997 | Köster | 435/6 |
| 5,691,142 A | 11/1997 | Dahlberg et al. | 435/6 |
| 5,700,642 A | 12/1997 | Monforte et al. | 435/6 |
| 5,710,028 A | 1/1998 | Eyal et al. | 435/91.1 |
| 5,719,028 A | 2/1998 | Dahlberg et al. | 435/6 |
| 5,742,049 A | 4/1998 | Holle et al. | 250/282 |
| 5,760,393 A | 6/1998 | Vestal et al. | 250/282 |
| 5,770,272 A | 6/1998 | Biemann et al. | 427/421 |
| 5,777,324 A | 7/1998 | Hillenkamp | 250/288 |
| 5,777,325 A | 7/1998 | Weinberger et al. | 250/287 |
| 5,795,714 A | 8/1998 | Cantor et al. | 435/6 |
| 5,795,763 A | 8/1998 | Dahlberg et al. | 435/194 |
| 5,821,063 A | 10/1998 | Patterson et al. | 435/6 |
| 5,830,655 A | 11/1998 | Monforte et al. | 435/6 |
| 5,837,450 A | 11/1998 | Dahlberg et al. | 435/6 |
| 5,843,654 A | 12/1998 | Heisler et al. | 435/6 |
| 5,843,669 A | 12/1998 | Kaiser et al. | 435/6 |
| 5,846,710 A | 12/1998 | Bajaj | 435/6 |
| 5,846,717 A | 12/1998 | Brow et al. | 435/6 |
| 5,851,765 A | 12/1998 | Köster | 435/6 |
| 5,853,989 A | 12/1998 | Jeffreys et al. | 435/6 |
| 5,854,486 A | 12/1998 | Dreyfus | 250/288 |
| 5,856,092 A | 1/1999 | Dale et al. | 435/6 |
| 5,864,137 A | 1/1999 | Becker et al. | 250/287 |
| 5,869,242 A | 2/1999 | Kamb | 435/6 |
| 5,871,911 A | 2/1999 | Dahlberg et al. | 435/6 |
| 5,872,003 A | 2/1999 | Köster | 435/283.1 |
| 5,885,775 A | 3/1999 | Haff et al. | 435/6 |
| 5,888,780 A | 3/1999 | Dahlberg et al. | 435/91.53 |
| 5,888,819 A | 3/1999 | Goelet et al. | 435/5 |
| 5,900,481 A | 5/1999 | Lough et al. | 536/55.3 |
| 5,925,520 A | 7/1999 | Tully et al. | 435/6 |
| 5,928,906 A | 7/1999 | Köster et al. | 435/91.2 |
| 5,965,363 A | 10/1999 | Monforte et al. | 435/6 |
| 5,976,798 A | 11/1999 | Parker et al. | 435/6 |
| 6,004,744 A | 12/1999 | Goelet et al. | 435/5 |
| 6,022,688 A | 2/2000 | Jurinke et al. | 435/6 |
| 6,024,925 A | 2/2000 | Little et al. | 422/100 |
| 6,027,890 A | 2/2000 | Ness et al. | 435/6 |
| 6,043,031 A | 3/2000 | Köster et al. | 435/6 |
| 6,074,823 A | 6/2000 | Köster | 435/6 |
| 6,090,558 A | 7/2000 | Butler et al. | 435/6 |
| 6,104,028 A | 8/2000 | Hunter et al. | 250/288 |
| 6,111,251 A | 8/2000 | Hillenkamp | 250/288 |
| 6,133,436 A | 10/2000 | Köster et al. | 536/24.3 |
| 6,140,053 A | 10/2000 | Köster | 435/6 |
| 6,146,854 A | 11/2000 | Köster et al. | 435/1.1 |
| 6,194,144 B1 | 2/2001 | Koster | 435/6 |
| 6,197,498 B1 | 3/2001 | Koster | 435/6 |
| 6,207,370 B1 | 3/2001 | Little et al. | 435/6 |
| 6,221,601 B1 | 4/2001 | Koster et al. | 435/6 |
| 6,221,605 B1 | 4/2001 | Koster | 435/6 |
| 6,225,061 B1 | 5/2001 | Becker | 435/6 |
| 6,225,450 B1 | 5/2001 | Köster | 536/22.1 |
| 6,235,478 B1 | 5/2001 | Koster | 435/6 |
| 6,238,871 B1 | 5/2001 | Koster | 435/6 |
| 6,258,538 B1 | 7/2001 | Koster et al. | 435/6 |
| 6,265,716 B1 | 7/2001 | Hunter et al. | 250/288 |
| 6,268,131 B1 | 7/2001 | Kang et al. | 435/6 |
| 6,268,144 B1 | 7/2001 | Koster et al. | 435/6 |
| 6,277,573 B1 | 8/2001 | Koster | 435/6 |
| 6,300,076 B1 | 10/2001 | Koster | 435/6 |
| 6,303,309 B1 | 10/2001 | Jurinke et al. | 435/6 |
| 6,322,970 B1 | 11/2001 | Little et al. | 435/6 |
| 2002/0005478 A1 | 1/2002 | Hillenkamp | 250/288 |

FOREIGN PATENT DOCUMENTS

| | | |
|---|---|---|
| EP | 0593789 | 4/1994 |
| EP | 0655501 | 5/1995 |
| EP | 0648280 | 5/1999 |
| GB | 2260811 | 4/1993 |
| JP | 59-131909 | 6/1984 |
| JP | 6294796 | 10/1994 |
| WO | 8903432 | 4/1989 |
| WO | 8906700 | 7/1989 |
| WO | 8909282 | 10/1989 |
| WO | 8912694 | 12/1989 |
| WO | 9003382 | 4/1990 |
| WO | 9007582 | 7/1990 |
| WO | 9014148 | 11/1990 |
| WO | 9113075 | 9/1991 |
| WO | 9115600 | 10/1991 |
| WO | 9205287 | 4/1992 |
| WO | 9213629 | 8/1992 |
| WO | 9215712 | 9/1992 |
| WO | 9320236 | 10/1993 |
| WO | 9323563 | 11/1993 |
| WO | 9400562 | 1/1994 |
| WO | 9411530 | 5/1994 |
| WO | 9416101 | 7/1994 |
| WO | 9421822 | 9/1994 |
| WO | 9428418 | 10/1994 |

| WO | 9507361 | 3/1995 |
| WO | 9957318 | 3/1995 |
| WO | 9513381 | 5/1995 |
| WO | 9515400 | 6/1995 |
| WO | 9531429 | 11/1995 |
| WO | 9610648 | 4/1996 |
| WO | 9614406 | 5/1996 |
| WO | 9615262 | 5/1996 |
| WO | 9617080 | 6/1996 |
| WO | 9621042 | 7/1996 |
| WO | 9629431 | 9/1996 |
| WO | 9630545 | 10/1996 |
| WO | 9632504 | 10/1996 |
| WO | 9636731 | 11/1996 |
| WO | 9636986 | 11/1996 |
| WO | 9636987 | 11/1996 |
| WO | 9637630 | 11/1996 |
| WO | 9627681 | 12/1996 |
| WO | 9708306 | 3/1997 |
| WO | 9716699 | 5/1997 |
| WO | 9733000 | 9/1997 |
| WO | 9737041 | 10/1997 |
| WO | 9742348 | 11/1997 |
| WO | 9743617 | 11/1997 |
| WO | 9812734 | 3/1998 |
| WO | 9820019 | 5/1998 |
| WO | 9820020 | 5/1998 |
| WO | 9820166 | 5/1998 |
| WO | 9833808 | 8/1998 |
| WO | 9854571 | 12/1998 |
| WO | 9912040 | 3/1999 |
| WO | 9931278 | 6/1999 |
| WO | 0056446 | 9/2000 |
| WO | 0060361 | 10/2000 |

OTHER PUBLICATIONS

Ardrey, Bob, Electrospray mass spectrometry, *Spectroscopy Europe 4*: 10–20 (1992).

Arlinghaus et al., "Applications of resonance ionization spectroscopy for semiconductor, environmental and biomedical analysis, and for DNA sequencing," *SPIE*, vol. 1435, *Opt. Methods Ultrasensitive Detect. Anal. Tech. Appl.* pp. 26–35 (1991).

Barany F., Genetic disease detection and DNA amplification using cloned thermostable ligase, *Proc. Natl. Acad. Sci. 88*: 189–193 (1991).

Barrell, DNA Sequencing: Present Limitations and Prospects for the Future, *FASEB Journal 5*: 40–45 (1991).

Beck et al., Applications of dioxetane chemiluminescent probes to molecular biology, *Anal. Chem. 62*: 2258–2270 (1990).

Beck et al., Chemiluminescent detection of DNA: application for DNA sequencing and hybridization, *Nucl Acids Res 17*: 5115–5123 (1989).

Berkenkamp et al., Infrared MALDI mass spectrometry of large nucleic acids, *Science 281*: 260–262 (1998).

Braun et al., Improved Analysis of Microsatellites Using Mass Spectrometry, *Genomics 46*: 18–23 (1997).

Braun et al., Detecting CFTR gene mutations by using primer oligo base extension and mass spectrometry, *Clinical Chemistry 43*: 1151–1158 (1997).

Broude et al., Enhanced DNA sequencing by hybridization, *Proc. Natl. Acad. Sci. USA 91*: 3072–3076 (1994).

Caldwell et al., Mid–infrared matrix assisted laser desorption ionization with a water/glycerol matrix, *Applied Surface Science 127–129*: 242–247 (1998).

Chakrabarti et al., Sequence of simian immunodeficiency virus from macaque and its relationship to other human simian retroviruses, *Nature 328*: 543–547 (1987).

Chee, Enzymatic multiples DNA sequencing, *Nucleic Acids Res. 19*(12): 3301–3305 (1991).

Chen et al., "Laser mass spectrometry for DNA fingerprinting for forensic applications", *Annual Meeting of the Society of Photo Optical Instrumentation Engineers*, Jul. 24–29, 1994.

Chrisey et al., Fabrication of patterned DNA surfaces, *Nucl. Acids. Res. 24*: 3040–3047 (1996).

Chrisey et al., Covalent attachment of synthetic DNA to self–assembled monolayer films, *Nucl. Acids Res. 24*: 3031–3039 (1996).

Connolly, Oligonucleotides Containing Modified Bases, *Oligonucleotides and Analogues, A Practical Approach*, Edited by F. Eckstein, Oxford University Press Ch. 7, pp. 155–183 (1991).

Covey, et al., The determination of protein, oligonucleotide and peptide molecular weights by ion–spray mass spectrometry, *Rapid Comm. Mass Spectrom. 2*: 249–256 (1988).

Crain, Mass spectrometric techniques in nucleic acid research, *Mass Spectrom. Rev. 9*: 505–554 (1990).

Database WPI, WPI Acc. No. 96140362/199615, citing German Patent No. DE4431174 published Mar. 7, 1996 [see item DV].

Database WPI, WPI Acc. No. 96222896/199623, citing German Patent No. DE4438630 published May 2, 1996 [see item DW].

Derwent #010108710 WPI Acc. No. 95–009963/199502 (citing, Japanese Patent Application No. JP 6294796, published Oct. 21, 1994) [see item DX].

Derwent #01022178 WPI Acc. No. 95–123433/199516 (citing International PCT application No. WO 9507361, published Mar. 16, 1995) [see item EQ].

Derwent #007515331 WPI Acc. No. 88–149264/198822 (citing, European Patent Application No. EP 269520, published Jun. 1, 1988) [see item DO].

Derwent #008221916 WPI Acc. No. 90–108917/199015 (citing, European Patent Application No. EP 360677, published Mar. 28, 1990) [see item DP].

Derwent #008541935 WPI Acc. No. 91–045998/199107 (citing, European Patent Application No. EP 412883, published Feb. 13, 1991) [see item DO].

Derwent #001797565 WPI Acc. No. 61–011665/198601 (citing, Japanese Patent Application No. JP 59–131909, now Patent JP84141909, published Jan. 20, 1986) [see item FV].

Doktycz et al., "Analysis of Polymerase Chain Reaction–Amplified DNA Products by Mass Spectrometry Using Matrix Assisted Laser Desorption and Electrospray: Current Status" *Anal. Biochem. 230*: 205–214 (1995).

Eckstein (ed.), *Oligonucleotides and Analogues*, IRL Press, Oxford (1991).

Edmonds et al., Thermospray liquid chromatography–mass spectrometry of nucleosides and of enzymatic hydrolysates of nucleic acids, *Nucleic Acids Research 13*: 8197–8206 (1985).

Ehring et al., Photochemical versus thermal mechanisms in matrix–assisted laser desorption/ionization probed by back side desorption, *Rapid Comm in Mass Spect 10*: 821–824 (1996).

Feng et al., The RNA Component of Human Telomerase, *Science 269*(5228): 1236–1241 (1995).

Ferrie et al., Development, multiplexing, and application of ARMS tests for common mutations in the CFTR gene, *Am. J. Hum. Genet. 51*: 251–262 (1992).

Frank and Köster, DNA chain length and the influence of base composition on electrophoretic mobility of oligodeoxyribonucleotides in polyacrylamide–gels, *Nucl. Acids Res. 6*: 2069–2087 (1979).

Fu et al., A DNA sequencing strategy which requires only five bases of known terminal sequence for priming, Paper presented, Genome Mapping and Sequencing Conference, Cold Spring Harbor Laboratory, N.Y. May 10–14, 1995.

Fu et al., Sequencing double–stranded DNA by strand displacement, *Nucl Acids Res 25*: 677–679 (1997).

Fu et al., A DNA sequencing strategy that requires only five bases of known terminal sequence for priming, *Proc. Natl. Acad. Sci. USA 92*: 10162–10166 (1995).

Fu et al., Efficient preparation of short DNA sequence ladders potentially suitable for MALDI–TOF DNA sequencing, *Genetic Analysis 12*: 137–142 (1996).

Fu et al., Sequencing exons 5 to 8 of the p53 gene by MALDI–TOF mass spectrometry, *Nat Biotechnol 16*: 381–384 (1998).

Ganem et al., Detection of oligonucleotides duplex forms by ion–spray mass spectrometry, *Tetrahedron Letters 34*(9): 1445–1448 (1993).

*Genetics in Medicine*, Thompson, J.S. and M.W. Thompson, eds., W.B. Saunders Co., Philadelphia, PA (1986).

Gildea et al., A versatile acid–labile linker for modification of synthetic biomolecules, *Tetrahedron Letters 31*: 7095–7098 (1990).

Gross et al., Investigations of the metastable decay of DNA under ultraviolet matrix–assisted laser desorption/ionization conditions with post–source–decay analysis and hydrogen/deuterium exchange, *J Amer Soc for Mass Spect 9*: 866–878 (1998).

Gruić–Sovulj I. et al., Matrix–assisted laser desorption/ionization mass spectrometry of transfer ribonucleic acids isolated from yeast, *Nucleic Acids Res. 25*(9): 1859–61 (1997).

Gust et al., Taxonomic classification of Hepatitis A virus, *Interviroloy 20*: 1–7 (1983).

Guyader et al., Genome organization and transactivation of the human immunodeficiency virus type 2, *Nature 328*: 662–669 (1987).

Haglund et al., Matrix–assisted laser–desorption mass spectrometry of DNA using an infrared free–electron laser, *SPIE 1854*: 117–128 (1993).

Higuchi et al., Kinetic PCR analysis: Real–time monitoring of DNA amplification reactions, *Bio/Technology 11*: 1026–1030 (1993).

Hillenkamp et al., Matrix Assisted UV–Laser Desorption/Ionization: A New Approach to Mass Spectrometry of Large Biomolecules, *Biological Mass Spectrometry*, Editors: A. L. Burlingame and J. A. McCloskey, Elsevier Science Publishers, B. V., Amsterdam, pp. 49–61 (1989).

Hillenkamp et al., Laser desorption mass spectrometry Part 1: Basic mechanisms and techniques, *Mass Spectrometry in the Biological Sciences: A tutorial*, pp. 165–179 (1992).

Hsiung et al., A new simpler photoaffinity analogue of peptidyl rRNA, *Nucl Acids Res 1*: 1753–1762 (1974).

Human Gene Mutations, D.N. Cooper and M. Krawczak, BIOS Publishers, (1993).

Huth–Fehre et al., Matrix–assisted laser desorption mass spectrometry of oligodeoxythymidylic acids, *Rapid Comm in Mass Spect 6*: 209–213 (1992).

Jacobson et al., Applications of Mass Spectrometry to DNA Sequencing, *Genet. Anal. Tech. Appl. 8*(8): 223–229 (1991).

Jacobson et al., "Applications of mass spectrometry to DNA fingerprinting and DNA sequencing", *International Symposium on the Forensic Aspects of DNA Analysis*, pp. 1–18, Mar. 29–Apr. 2, 1993.

Ji et al., Two–dimensional electrophoretic analysis of proteins expressed by normal and cancerous human crypts: Application of mass spectrometry to peptide–mass fingerprinting, *Electrophoresis 15*: 391–405 (1994).

Juhasz et al., Applications of delayed extraction matrix–assisted laser desorption ionization time–of–flight mass spectrometry to oligonucleotide analysis, *Anal. Chem. 68*: 941–946 (1996).

Jurinke et al., Recovery of nucleic acids from immobilized biotin–streptavidin complexes using ammonium hydroxide and applications in MALDI–TOF mass spectrometry, *Anal. Chem. 69*: 904–910 (1997).

Jurinke et al., Detection of hepatitis B virus DNA in serum samples via nested PCR and MALDI–TOF mass spectrometry, *Genetic Analysis 13*: 67–71 (1996).

Jurinke et al., Application of nested PCR and mass spectrometry for DNA–based virus detection: HBV–DNA detected in the majority of isolated anti–HBc positive sera, *Genetic Analysis 14*: 97–102 (1998).

Jurinke et al., Analysis of ligase chain reaction products via matrix–assisted laser desorption/ionization time–of–flight–mass spectrometry, *Analyt Biochem 237*: 174–181 (1996).

Kirpekar et al., DNA sequence analysis by MALDI mass spectromety, *Nucleic Acids Res. 26*: 2554–9 (1998).

Köster et al., A strategy for rapid and efficient DNA sequencing by mass spectrometry, *Nature Biotech 14*: 1123–1128 (1996).

Köster et al., Oligonucleotide Synthesis and Multiplex DNA Sequencing using Chemiluminescent Detection, *Nucleic Acids Research, Symposium Series No. 24* pp. 318–321 (1991).

Köster et al., Well–defined insoluble primers for the enzymatic synthesis of oligo– and polynucleotides, *Hoppe Seylers Z. Physiol. Chem. 359*(11): 1579–1589 (1978).

Köster et al., Polymer support oligonucleotide synthesis— XV$^{1,2}$, *Tetrahedron 40*: 102–112 (1984).

Köster et al., N–acyl protecting groups for deoxynucleotides: A quantitative and comparative study, *Tetrahedron 37*: 363–369 (1981).

Köster et al., Some improvements in the synthesis of DNA of biological interest, *Nucl Acids Res 7*: 39–59 (1980).

Kuppuswamy et al., Single nucleotide primer extension to detect genetic diseases: Experimental application to hemophilia B (factor IX) and cystic fibrosis genes, *Proc. Natl. Acad. Sci. USA 88*: 1143–1147 (1991).

Landegren et al., DNA diagnostic–Molecular techniques and automation, *Science 242*: 229–237 (1988).

Landegren et al., A ligase–mediated gene detection technique, *Science 241*: 1077–1080 (1988).

Lawrance et al., Megabase–scale mapping of the HLA gene complex by pulsed field gel electrophoresis, *Science 235*:1387–1389 (1987).

Li et al., High–Resolution MALDI Fourier Transform Mass Spectrometry of Oligonucleotides, *Anal Chem 68*: 2090–2096 (1996).

Light–Wahl et al., Observation of small oligonucleotide duplex by electrospray ionization mass spectrometry, *J. Am. Chem. Soc. 115*: 804–805 (1993).

Little et al., Verification of 50– to 100–mer DNA and RNA sequences with high–resolution mass spectrometry, *Proc. Natl. Acad. Sci. USA 92*: 2318–2322 (1995).

Little et al., Direct detection of synthetic and biologically generated double–stranded DNA by MALDI–TOF MS, *J. Mass Spec 17*: 1–8 (1997).

Little et al., Detection of RET proto–oncogene codon 634 mutations using mass spectrometry, *J. Mol Med. 75*: 745–750 (1997).

Little et al., Identification of apolipoprotein E polymorphisms using temperature cycled primer oligo base extension and mass spectrometry, *Eur. J. Chem. Clin. Biochem. 35(7)*: 545–8 (1997).

Little et al., MALDI on a chip: analysis of arrays of low–femtomole to subfemtomole quantitites of synthetic oligonucleotides and DNA diagnostic products dispensed by a piezoelectric pipet, *Anal Chem 69*: 4540–4546 (1997).

Little et al., Mass spectrometry from miniaturized arrays for full comparative DNA analysis, *Nature Med 3*: 1413–1416 (1997).

Liu et al., Rapid screening of genetic polymorphisms using buccal cell DNA with detection by matrix–assisted laser desorption/ionization mass spectrometry, *Rapid Comm in Mass Spect 9*: 735–743 (1995).

Liu et al., "Use of a Nitrocellulose Film Substrate in Matrix–Assisted Laser Desorption/Ionization Mass Spectrometry for DNA Mapping and Screening", *Anal. Chem. 67*: 3482–3490 (1995).

Lopez–Galindez et al.,Characterization of genetic variation and 3'–adizo–3'deoxythymidine–resistance mutations of human immunodeficiency virus by the RNase A mismatch cleavage method,*Proc. Natl. Acad. Sci. USA 88*: 4280–4284 (1991).

Lyamichev et al., Structure–specific endonucleolytic cleavage of nucleic acids by eubacterial DNA polymerase, *Science 260(5109)*: 778–83 (1993).

Matthews and Kricka, Analytical strategies for the use of DNA probes, *Analytical Biochem. 169*: 1–25 (1988).

*Methods in Enzymology* vol. 193: Mass Spectrometry (McCloskey, editor), p. 425 Academic Press, New York (1990).

Mizusawa et al., Improvement of the Dideoxy Chain Termination Method of DNA Sequencing by use of Deoxy–7–Deazaguanosine Triphosphate in Place of dGTP, *Nucleic Acids Research*, vol. 14, No. 3, pp. 1319–1325 (1986).

Monforte and Becker, High–throughput DNA analysis by time–of–flight mass spectrometry, *Nature Medicine 3*: 360–362 (1997).

Naito et al., Detection of Tyrosine Hydroxylase mRNA and Minimal Neuroblastoma Cells by the Reverse Transcription– Polymerase Chain Reaction, *European Journal of Cancer 27*: 762–765 (1991).

Nelson et al., Time of flight mass spectrometry of nucleic acids by laser ablation and ionization from a frozen aqueous matrix, *Rapid Comm. in Mass Spect. 4*: 348–351 (1990).

Nelson et al., Volatilization of High Molecular Weight DNA by Pulsed Laser Ablation of Frozen Aqueous Solutions, *Science 246*: 1585–1587 (1989).

Nielsen et al., Sequence–selective recognition of DNA by strand displacement with a thymine–substituted polyamide, *Science 254*: 1497–1500 (1991).

Nikiforov et al., The use of 96–well polystyrene plates for DNA hybridization–based assays: an evaluation of different approaches to oligonucleotide immobilization, *Anal Biochem 227*: 201–209 (1995).

Nikiforov et al., Genetic bit analysis: a solid phase method for typing single nucleotide polymorphisms, *Nucleic Acids Res 22(20)*: 4167–4175 (1994).

Nordhoff et al., Ion stability of nucleic acids in infrared matrix–assisted laser desorption/ionization mass spectrometry, *Nuc Acids Res. 21*: 3347–3357 (1993).

Nordoff et al., Matrix–assisted laser desorption/ionization mass spectrometry of nucleic acids with wavelength in the ultraviolet and infrared, *Rapid Comm. Mass Spect 6*: 771–776 (1992).

O'Donnell et al., MassArray as an enabling technology for the industrial–scale analysis of DNA, *Genetic Engineering News 17(21)*: 39–41, Dec. 1997.

O'Donnell et al., High–density, covalent attachment of DNA to silicon wafers for analysis by MALDI–TOF, mass spectrometry, *Analytical Chemistry 69*: 2438–2443 (1997).

O'Donnell–Maloney et al., Microfabrication and array technologies for DNA sequencing and diagnostics, *Genetic Analysis: Biomolecular Engineering 13*: 151–157 (1996).

Ordoukhanian et al., Design and Synthesis of a Versatile Photocleavable DNA Building Block. Application to Phototriggered Hybridization, *J. Am. Chem. Soc. 117*: 9570–9571 (1995).

*Organic Charge Transfer Complex* by R. Foster, Academic Press (1969).

Overberg et al., Laser Desorption Mass Spectrometry. Part II Performance and Applications of Matrix–Assisted Laser Desorption/Ionization of Large Biomolecules, *Mass Spectrometry in the Biological Sciences: A Tutorial*. Editor: M. L. Gross, Kluwer Publications, The Netherlands, pp. 181–197 (1992).

Palejwala et al., Quantitative Multiplex Sequence Analysis of Mutational Hot Spots. Frequency and Specificity of Mutations Induced by a Site–Specific Ethenocytosine in M13 Viral DNA, *Biochemistry 32*: 4105–4111 (1993).

Pasini et al., RET mutations in human disease, *Trends in Genetics 12(4)*: 138–144 (1996).

*PCR*, C.R. Newton and A. Graham, BIOS Publishers, (1994).

Pieles et al., Matrix–assisted laser desorption ionization time–of–flight mass spectrometry: a powerful tool for the mass and sequence analysis of natural and modified oligonucleotides, *Nucleic Acids Res. 21(14)*: 3191–3196 (1993).

Pierce Catalog, pp. T123–T154, 1994.

Pomerantz et al., Determination of oligonucleotide composition from mass spectrometrically measured molecular weight, *Am. Soc. Mass Spectrom. 4*: 204–09 (1993).

Ratner et al., Complete nucleotide sequence of the AIDS virus, HTLV–III, *Nature 313*: 227–284 (1985).

*Reactive Molecules*, The neutral reactive intermediates in organic chemistry, by C. Wentrup, John Wiley & Sons (1984).

Rolfs et al., *PCR: Clinical Diagnostics and Research*, Springer–Verlag, (1992).

Ruppert et al., Preparation of plasmid DNA as sequencing templates in a microtiter plate format, Paper presented, Genome Mapping and Sequencing Conference, Cold Spring Harbor Laboratory, N.Y. May 10–14, 1995.

Ruppert et al., A filtration method for plasmid isolation using microtitier filter plates, *Anal. Biochem. 230*: 130–134 (1995).

Ruppert et al., A rapid and high throughput method for plasmid isolation, Presented: Automation in Mapping and DNA Sequencing Conference, Aug. 31–Sep. 2, 1994.

Sambrook et al., Molecular Cloning: A Laboratory Manual, Cold Spring Harbor Laboratory Press (1989).

Schieltz et al., Progress towards DNA sequence determination using laser ablation time–of–flight mass spectrometry, paper presented at 40th ASMS Conference on Mass Spectrometry and Allied topics, Washington, D.C., Jun. 1992.

Schneider and Chait, Increased stability of nucleic acids containing 7–deaza–guanosine and 7–deaza–adenosine may enable rapid DNA sequencing by matrix–assisted laser desorption mass spectrometry, *Nucleic Acids Res. 23*(9): 1570–1575 (1995).

Schram, Mass spectrometry of nucleic acid components, *Biomed. App. Mass Spectrom. 34*: 203–287 (1990).

Seela and Röling, 7–deazapurine containing DNA: efficiency of $c^7G_dTP$, $c^7A_dTP$ and $c^7I_dTP$ incorporation during PCR–amplification and protection from endodeoxyribonuclease hydrolysis, *Nucleic Acids Res. 20*: 55–61 (1992).

Seela and Kehne, Palindromic octa– and dodecanucleotides containing 2'–deoxytubercidin: Synthesis, hairpin formation, and recognition by the endodeoxyribonuclease EcoRI, *Biochemistry 26*: 2232–2238 (1987).

Sequenom Obtains Important New Patent for DNA Mass Array™ Technology, Press Release: May 24, 1999, http://www.sequenom.com/pr/pressrelease/52499.html.

Sequenom Advances the Industrial Genomics Revolution with the Launch of Its DNA MassArray™ Automated Process Line, Press Release: Sep. 28, 1998, http://www.sequenom.com/pressrelease.htm.

Sequenom Reports DNA MassArray™ Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Sequenom Uses DNA MassArray™ to Sequence Section of Human Cancer–Related p53 Gene, Press Release: Mar. 27, 1998, http://www.sequenom.com/pressrelease.htm.

Sequenom Reports On Use of Its DNA MassArray™ Technology to Analyze Genes Associated with Alzheimer's Disease and Arterioslcerosis: Technology Has Applications in Drug Development, Press Release: Sep. 22, 1997, http://www.sequenom.com/pressrelease.htm.

Sequenom Obtains Patents for DNA MassArray™ Technology, Press Release: Apr. 27, 1999, http://www.sequenom.com/pressrelease/42799.htm.

Sequenom Signs Agreement With Bruker–Franzen Analytik to Develop Mass Spectrometer for DNA Massarray Analysis, Press Release: Jan. 12, 1998, http://www.sequenom.com/pressrelease.htm.

Shaler et al., Effect of Impurities on the matrix–assisted laser desorption mass spectra of single–stranded oligodeoxynucleotides, *Anal. Chem. 68*: 576–579 (1996).

Siegert et al., Matrix–assisted laser desorption/ionization time–of–flight mass spectrometry for the detection of polymerase chain reaction products containing 7–deasapurine moieties, *Anal. Biochem. 243*: 55–65 (1996).

Sinha et al., Polymer support oligonucleotide synthesis XVIII: Use of B–cyanoethyl–N, N–dialkylamino–/N–morpholino phosphoramidite of deoxynucleosides for the synthesis of DNA fragments simplifying deprotection and isolation of final product, *Nucleic Acids Res. 12*: 4539–4557 (1984).

Sinha et al., β–cyanoethyl N, N–dialkylamino/N–morpholinomonochloro phosphoamidites, new phosphitylating agents facilitating ease of deprotection and work–up of synthesized oligonucleotides, *Tetrahedron Lett. 24*: 5843–5846 (1983).

Siuzdak, The emergence of mass spectrometry in biochemical research, *Proc. Natl. Acad. Sci. USA 91*: 11290–11297 (1994).

Smith et al., Capillary zone electrophoresis–mass spectrometry using an electrospray ionization interface, *Anal. Chem. 60*: 436–441 (1988).

Smith et al., New Developments in Biochemical Mass Spectrometry: Electrospray Ionization, *Anal. Chem. 62*: 882–899 (1990).

Sokolov, Primer extension technique for the detection of single nucleotide in genomic DNA, *Nucleic Acid Res. 18*(12): 3671 (1990).

Sproat et al., The synthesis of protected 5'–amino–2', 5'–dideoxyribonucleoside–3'–O–phosphoramidites; applications of 5'–amino–oligodeoxynucleotides, *Nucleic Acids Res. 15*: 6181–6196 (1987).

Stahl et al., Solid Phase DNA Sequencing using the Biotin–Avidin System, *Nucleic Acids Research 16*(7): 3025–3039 (1988).

Syvanen et al., Detection of Point Mutations by Solid–Phase Methods, *Human Mutation 3*(3): 172–179 (1994).

Tang et al., Matrix–assisted laser desorption/ionization mass spectrometry of immobilized duplex DNA probes, *Nucleic Acid Res. 23*(16): 3126–3131 (1995).

Tang et al., Matrix–assisted Laser Desorption/Ionization of Restriction Enzyme–digested DNA, *Rapid Communications in Mass Spectrometry 8*(2): 183–186 (1994).

Tang et al., Detection of 500–nucleotide DNA by laser desorption mass spectrometry, *Rapid Commun. Mass Spectrom. 8*: 727–730 (1994).

Tang, et al., Improving mass resolution in MALDI/TOF analysis of DNA, American Society of Mass Spectrometrists Conference: May 21 to 26, 1995.

*The Human Genome*, T. Strachan, BIOS Scientific Publishers (1992).

*Time of Flight Mass Spectrometry of DNA for Rapid Sequence Determination*. Technical Progress Report, Jul. 31, 1991–Jul. 31, 1992, Arizona State University., Tempe.

Trainor, DNA Sequencing, Automation and the Human Genome, *Anal. Chem. 62*: 418–426 (1990).

Valaskovic, et al., Attomole–sensitivity electrospray source for large–molecule mass spectrometry, *Anal. Chem. 67*: 3802–3805 (1995).

Vorm et al., Improved resolution and very high sensitivity in MALDI TOF of matrix surfaces made by fast evaporation, *Anal. Chem. 66*: 3281–3287 (1994).

Wain–Hobson et al., Nucleotide sequence of the AIDS virus, LAV, *Cell 40*: 9–17 (1985).

Walker et al., Multiplex strand displacement amplification (SDA) and detection of DNA sequences from *Mycobacterium tuberculosis* and other mycobacteria, *Nucleic Acids Res.* 22(13): 2670–2677 (1994).

Wang, Solid phase synthesis of protected peptides via photolytic cleavage of the α-methylphenacyl ester anchoring linkage, *J. Org. Chem.* 41(20): 32583–261 (1976).

Wiedmann M. et al., Ligase chain reaction (LCR)—overview and applications, *PCR Methods Appl.* 3(4): S51–S64 (1994).

William, Time of flight mass spectrometry of DNA laser–ablated from frozen aqueous solutions: applications to the Human Genome Project, *Intl. J. Mass Spectrom. and Ion Processes 131*: 335–344 (1994).

Wolter et al., Negative ion FAB mass spectrometric analysis of non–charged key intermediated in oligonucleotide synthesis: rapid identification of partially protected dinucleoside monophosphates, *Biomedical Environmental Mass Spectrometry 14*: 111–116 (1987).

Wong, Ch. 12: Conjugation of proteins to solid matrices, *Chemistry of Protein Conjugation and Cross Linking 12*: 295–217 (1993).

Wu et al., Matrix–assisted Laser Desorption Time–of–flight Mass Spectrometry of Oligonucleotides Using 3–Hydroxypicolinic Acid as an Ultraviolet–sensitive Matrix, *Rapid Comm Mass Spec 7*: 142–146 (1993).

Wu et al., Time–of–Flight Mass Spectrometry of Underivatized Single–Stranded DNA Oligomers by Matrix–Assisted Laser Desorption, *Anal. Chem. 66*: 1637–1645 (1994).

Wu et al., Allele–specific enzymatic amplification of β–globin genomic DNA for diagnosis of sickle cell anemia, *Proc. Natl. Acad. Sci. USA* 86: 2757–2760 (1989).

Yamashita et al., Electrospray ion source. Another variation on the free–jet theme, *J. Phys. Chem.* 88: 4451–4459 (1984).

Bai et al., "Matrix–Assisted Laser Desprption/Ionization Mass Spectrometry of Restriction Enzyme–Digested Plasmid DNA Using an Active Nafion Substrate", *Rapid Comm. Mass Spec.*, 8:687–691 (1994).

Bannwarth, "Solid–phase synthesis of oligodeoxynucleotides containing phosphoramidate internucleotide linkages and their specific chemical cleavage", *Helvetica Chimica Acta*, 71:1517–1525 (1988).

Benner and Jaklevic, "DNA Base–Pair Substitutions Detected in Double–Stranded DNA With Matrix–Assisted Laser Desorption/Ionization Time–of–Flight Mass Spectrometry", *Eur. Mass Spectrum.*, 1:479–485 (1995).

Chang et al., "Detection of ΔF508 Mutation of the cystic Fibrosis Gene by Matrix–Assisted Laser Desorption/Ionization Mass Spectrometry", *Rapid Comm. in Mass Spectrom.*, 9:772–774 (1995).

Cosstick et al., "Synthesis and Properties of dithymidine phosphate analogues containing 3'–thiothimidine", *Nucl. Acid Res.*, 18:829–835 (1990).

Fitzgrald et al., "Basic Matrices for the Matrix–Assisted Laser Desorption/Ionization Mass Spectrometry of Proteins and Oligonucleotides", *Anal. Chem.*, 65:3204–3211 (1993).

Liu et al., "Use of Nitrocellulose Film Substrate in Matrix–Assisted Laser Desorption/Ionization Mass Spectrometry for DNA Mapping and Screening", *Anal. Chem.*, 67:3482–3490 (1995).

Nakayame et al., "Direct Sequencing of polymerase chain reaction amplified DNA fragments through the incorporation of deoxynucleoside a–thiotriphosphates", *Nucl. Acids Res.*, 16:9947–9959 (1988).

Siegert et al., "Matrix–assisted laser desorption/ionization Time–of–flight mass Spectrometry for the detection of polymerase chain reaction products containing 7–Deazapurinr moieties", *Anal. Biochem.*, 243:55–65 (1966).

Wu et al., The ligation amplification reaction (LAR)–amplification of specific DNA sequences using sequential rounds of template–dependent ligation *Genomics*, 4:560–569 (1989).

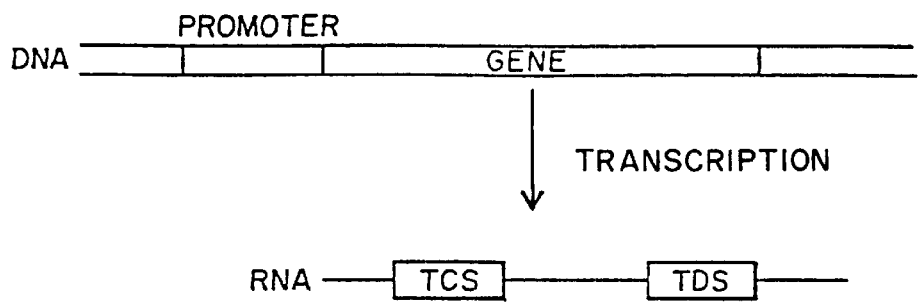
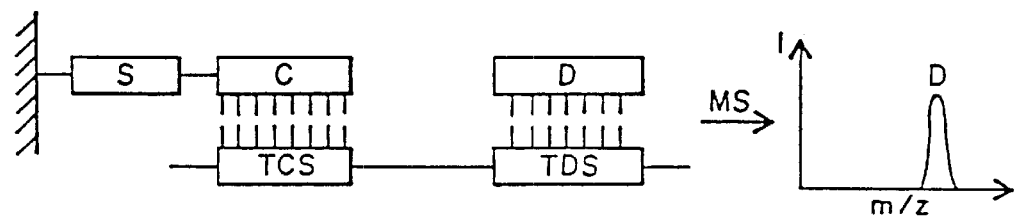
FIG. 6A
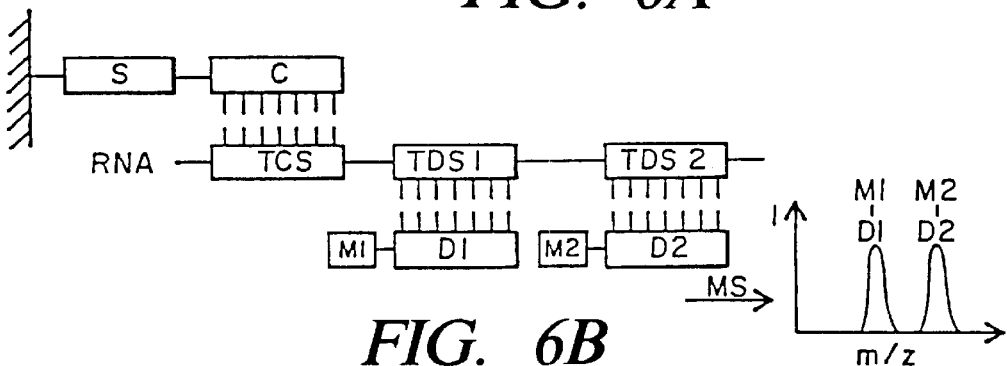
FIG. 6B
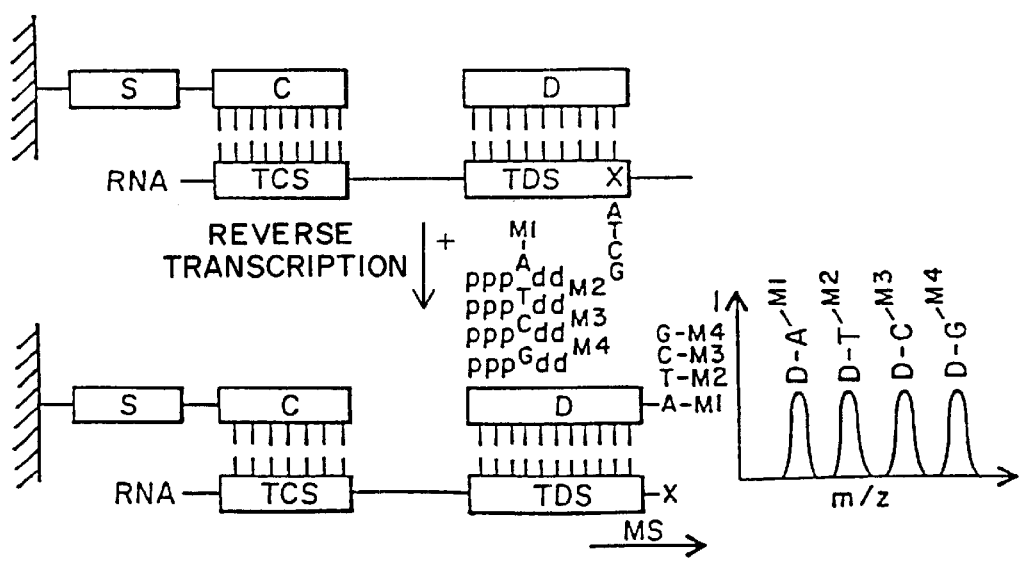
FIG. 6C

MOLECULAR WEIGHT OF THE VARIABLE FRAGMENTS IN Da:

| | | | ε2/ε2 | ε3/ε3 | ε4/ε4 | ε2/ε3 | ε2/ε4 | ε3/ε4 |
|---|---|---|---|---|---|---|---|---|
| 91 bp | SENSE | 28421 | X | X | | X | X | X |
| | ANTISENSE | 27864 | | | | | | |
| 83 bp | SENSE | 25747 | X | | | X | X | |
| | ANTISENSE | 25591 | | | | | | |
| 72 bp | SENSE | 22440 | | | X | | X | X |
| | ANTISENSE | 21494 | | | | | | |
| 48 bp | SENSE | 14844 | | X | X | X | X | X |
| | ANTISENSE | 14857 | | | | | | |
| 35 bp | SENSE | 10921 | | X | X | X | X | X |
| | ANTISENSE | 10751 | | | | | | |

FIG. 34A

```
              506507508
              IleIlePhe
primer    ACCATTAAAGAAAAATATCATCTTTGGTGTGTTTCCTATGATGAATATAGAAGCGTCATC (SEQ. ID. NO. 60)
wildtype                        ACCACAAAGGATACTACTTATATC          (7289,8)  (SEQ. ID. NO. 61)
ΔF508                     TAGAAACCACAAAGGATACTACTACTTATATC         (8846,8)  (SEQ. ID. NO. 62)
ΔI507                     TA---ACCACAAAGGATACTACTACTTATATC         (7891,2)  (SEQ. ID. NO. 63)
                TAG---AAACCACAAAGGATACTACTACTTATATC                (8846,8)  (SEQ. ID. NO. 64)
```

FIG. 34B

```
              506507508
              IleIlePhe
primer    ACCATTAAAGAAAAATATCATCTTTGGTGTGTTTCCTATGATGAATATAGAAGCGTCATC (SEQ. ID. NO. 60)
wildtype                        ACCACAAAGGATACTACTTATATC          (7289,8)  (SEQ. ID. NO. 61)
ΔF508              CTTTTATAGTAGAAACCACAAAGGATACTACTACTTATATC        (11612,6) (SEQ. ID. NO. 65)
ΔI507              CTTTTATAGTA---ACCACAAAGGATACTACTACTTATATC        (10657,0) (SEQ. ID. NO. 66)
506Ser             CTTTTATAG---AAACCACAAAGGATACTACTACTTATATC        (10666,0) (SEQ. ID. NO. 67)
                 CGTAGAAACCACAAAGGATACTACTACTTATATC                (9465,2)  (SEQ. ID. NO. 68)
```

ΔF508 (7916,9/7891,2)
Homozygous

ΔF508 (7913,0/7891,2)
Homozygous

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

GCAAGTGAAT CCTGAGCGTG                                          20

(2) INFORMATION FOR SEQ ID NO: 2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

GTGTGAAGGG TTCATATGC                                           19

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

ATCTATATTC ATCATAGGAA ACACCACA                                 28

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

GTATCTATAT TCATCATAGG AAACACCATT                               30

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GCTTTGGGGC ATGGACATTG ACCCGTATAA                                    30

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CTGACTACTA ATTCCCTGGA TGCTGGGTCT                                    30

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

TTGCCTGAGT GCAGTATGGT                                               20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

AGCTCTATAT CGGGAAGCCT                                               20

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

TTGTGCCACG CGGTTGGGAA TGTA                                          24

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

AGCAACGACT GTTTGCCCGC CAGTTG                                        26
```

(2) INFORMATION FOR SEQ ID NO: 11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

TACATTCCCA ACCGCGTGGC ACAAC                                       25

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

AACTGGCGGG CAAACAGTCG TTGCT                                       25

(2) INFORMATION FOR SEQ ID NO: 13:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

ACCATTAAAG AAAATATCAT CTTTGGTGTT TCCTATGATG AATATAGAAG CGTCATC      57

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

ACCACAAAGG ATACTACTTA TATC                                         24

(2) INFORMATION FOR SEQ ID NO: 15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

TAGAAACCAC AAAGGATACT ACTTATATC                                   29

(2) INFORMATION FOR SEQ ID NO: 16:

(i) SEQUENCE CHARACTERISTICS:
        (A) LENGTH: 26 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

TAACCACAAA GGATACTACT TATATC                                              26

(2) INFORMATION FOR SEQ ID NO: 17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

TAGAAACCAC AAAGGATACT ACTTATATC                                           29

(2) INFORMATION FOR SEQ ID NO: 18:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

CTTTTATAGT AGAAACCACA AAGGATACTA CTTATATC                                 38

(2) INFORMATION FOR SEQ ID NO: 19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

CTTTTATAGT AACCACAAAG GATACTACTT ATATC                                    35

(2) INFORMATION FOR SEQ ID NO: 20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

CTTTTATAGA AACCACAAAG GATACTACTT ATATC                                    35

(2) INFORMATION FOR SEQ ID NO: 21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

CGTAGAAACC ACAAAGGATA CTACTTATAT C                                      31

(2) INFORMATION FOR SEQ ID NO: 22:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

GAATTACATT CCCAACCGCG TGGCACAACA ACTGGCGGGC AAACAGTCGT TGCTGATT         58

(2) INFORMATION FOR SEQ ID NO: 23:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

AATCAGCAAC GACTGTTTGC CCGCCAGTTG TTGTGCCACG CGGTTGGGAA TGTAATTC         58

(2) INFORMATION FOR SEQ ID NO: 24:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GGCACGGCTG TCCAAGGAGC TGCAGGCGGC GCAGGCCCGG CTGGGCGCGG ACATGGAGGA        60

CGTGTGCGCC GCCTGGTGCA GTACCGCGGC GAGGTGCAGG CCATGCTCGG CCAGAGCACC       120

GAGGAGCTGC GGGTGCGCCT CGCCTCCCAC CTGCGCAAGC TGCGTAAGCG GCTCCTCCGC       180

GATGCCGATG ACCTGCAGAA GTCCCTGGCA GTGTACCAGG CCGGGGCCCG CGAGGGCGCC       240

GAGCGCGGCC TC                                                          252

(2) INFORMATION FOR SEQ ID NO: 25:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

GCAACATTTT GCTGCCGGTC ACGGTTCGAA CGTACGGACG TCCAGCTGAG ATCTCCTAGG        60

GGCCCATGGC TCGAGCTTAA GCATTAGTAC CAGTATCGAC AAAGGACACA                 110

(2) INFORMATION FOR SEQ ID NO: 26:

(i) SEQUENCE CHARACTERISTICS:
       (A) LENGTH: 110 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 26:

TGTGTCCTTT GTCGATACTG GTACTAATGC TTAAGCTCGA GCCATGGGCC CCTAGGAGAT      60

CTCAGCTGGA CGTCCGTACG TTCGAACCGT GACCGGCAGC AAAATGTTGC                110

(2) INFORMATION FOR SEQ ID NO: 27:

(i) SEQUENCE CHARACTERISTICS:
       (A) LENGTH: 217 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 27:

AACGTGCTGC CTTCCACCGC GATGTTGATG ATTATGTGTC TGAATTTGAT GGGGGCAGGC      60

GGCCCCCGTC TGTTTGTCGC GGGTCTGGTG TTGATGGTGG TTTCCTGCCT TGTCACCCTC      120

GACCTGCAGC CCAAGCTTGG GATCCACCAC CATCACCATC ACTAATAATG CATGGGCTGC      180

AGCCAATTGG CACTGGCCGT CGTTTTACAA CGTCGTG                              217

(2) INFORMATION FOR SEQ ID NO: 28:

(i) SEQUENCE CHARACTERISTICS:
       (A) LENGTH: 217 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 28:

CACGACGTTG TAAAACGACG GCCAGTGCCA ATTGGCTGCA GCCCATGCAT TATTAGTGAT      60

GGTGATGGTG GTGGATCCCA AGCTTGGGCT GCAGGTCGAG GGTGACAAGG CAGGAAACCA     120

CCATCAACAC CAGACCCGCG ACAAACAGAC GGGGGCCGCC TGCCCCCATC AAATTCAGAC     180

ACATAATCAT CAACATCGCG GTGGAAGGCA GCACGTT                              217

(2) INFORMATION FOR SEQ ID NO: 29:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 29:

GTAAAACGAC GGCCAGT                                                    17

(2) INFORMATION FOR SEQ ID NO: 30:

(i) SEQUENCE CHARACTERISTICS:
       (A) LENGTH: 17 base pairs
       (B) TYPE: nucleic acid
       (C) STRANDEDNESS: single
       (D) TOPOLOGY: linear -continued

```
        (ii) MOLECULE TYPE: cDNA (xi) SEQUENCE DESCRIPTION: SEQ ID NO: 30:

CAGGAAACAG CTATGAC                                                   17

(2) INFORMATION FOR SEQ ID NO: 31:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO: 31:

CTTCCACCGC GATGTTGA                                                  18

(2) INFORMATION FOR SEQ ID NO: 32:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO: 32:

TTGTAAAACG ACGGCCAGT                                                 19

(2) INFORMATION FOR SEQ ID NO: 33:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO: 33:

GTCACCCTCG ACCTGCAG                                                  18
```

DNA DIAGNOSTICS BASED ON MASS SPECTROMETRY

RELATED APPLICATIONS

This application is a continuation of U.S. application Ser. No. 09/495,444, filed Jan. 31, 2000, U.S. Pat. No. 6,300,076 and U.S. application Ser. No. 09/504,245, filed Feb. 15, 2000, U.S. Pat. No. 6,221,605. This application is a continuation of U.S. application Ser. No. 09/287,679, filed Apr. 6, 1999 U.S. Pat. No. 6,258,538. This application is also a continuation of U.S. application Ser. No. 08/617,256, filed Mar. 18, 1996 and now U.S. Pat. No. 6,043,031. This application is also a continuation-in-part of U.S. application Ser. No. 08/406,199 filed Mar. 17, 1995, and now U.S. Pat. No. 5,605,798. U.S. application Ser. No. 08/617,258 is a continuation-in-part of U.S. application Ser. No. 08/406,199. The subject matter of each of these applications is herein incorporated by reference in its entirety.

BACKGROUND OF THE INVENTION

The genetic information of all living organisms (e.g. animals, plants and microorganisms) is encoded in deoxyribonucleic acid (DNA). In humans, the complete genome is comprised of about 100,000 genes located on 24 chromosomes (The Human Genome, T. Strachan, BIOS Scientific Publishers, 1992). Each gene codes for a specific protein which after its expression via transcription and translation, fulfills a specific biochemical function within a living cell. Changes in a DNA sequence are known as mutations and can result in proteins with altered or in some cases even lost biochemical activities; this in turn can cause genetic disease. Mutations include nucleotide deletions, insertions or alterations (i.e. point mutations). Point mutations can be either "missense", resulting in a change in the amino acid sequence of a protein or "nonsense" coding for a stop codon and thereby leading to a truncated protein.

More than 3000 genetic diseases are currently known (Human Genome Mutations, D. N. Cooper and M. Krawczak, BIOS Publishers, 1993), including hemophilias, thalassemias, Duchenne Muscular Dystrophy (DMD), Huntington's Disease (HD), Alzheimer's Disease and Cystic Fibrosis (CF). In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klienfelter's Syndrome (XXY). Further, there is growing evidence that certain DNA sequences may predispose an individual to any of a number of diseases such as diabetes, arteriosclerosis, obesity, various autoimmune diseases and cancer (e.g. colorectal, breast, ovarian, lung).

Viruses, bacteria, fungi and other infectious organisms contain distinct nucleic acid sequences, which are different from the sequence contained in the host cell. Therefore, infectious organisms can also be detected and identified based on their specific DNA sequences.

Since the sequence of about 16 nucleotides is specific on statistical grounds even for the size of the human genome, relatively short nucleic acid sequences can be used to detect normal and defective genes in higher organisms and to detect infectious microorganisms (e.g. bacteria, fungi, protists and yeast) and viruses. DNA sequences can even serve as a fingerprint for detection of different individuals within the same species. (Thompson, J. S. and M. W. Thompson, eds., *Genetics in Medicine*, W. B. Saunders Co., Philadelphia, Pa. (1986).

Several methods for detecting DNA are currently being used. For example, nucleic acid sequences can be identified by comparing the mobility of an amplified nucleic acid fragment with a known standard by gel electrophoresis, or by hybridization with a probe, which is complementary to the sequence to be identified. Identification, however, can only be accomplished if the nucleic acid fragment is labeled with a sensitive reporter function (e.g. radioactive ($^{32}$P, $^{35}$S), fluorescent or chemiluminescent). However, radioactive labels can be hazardous and the signals they produce decay over time. Non-isotopic labels (e.g. fluorescent) suffer from a lack of sensitivity and fading of the signal when high intensity lasers are being used. Additionally, performing labeling, electrophoresis and subsequent detection are laborious, time-consuming and error-prone procedures. Electrophoresis is particularly error-prone, since the size or the molecular weight of the nucleic acid cannot be directly correlated to the mobility in the gel matrix. It is known that sequence specific effects, secondary structures and interactions with the gel matrix are causing artifacts.

In general, mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g. argon atoms), the molecular ion is fragmented forming secondary ions by the so-called collision induced dissociation (CID). The fragmentation pattern/pathway very often allows the derivation of detailed structural information. Many applications of mass spectrometric methods are known in the art, particularly in biosciences, and can be found summarized in *Methods of Enzymology*, Vol. 193:"Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Recent reviews summarizing this field include K. H. Schram, "Mass Spectrometry of Nucleic Acid Components, Biomedical Applications of Mass Spectrometry" 34, 203–287 (1990); and P. F. Crain, "Mass Spectrometric Techniques in Nucleic Acid Research, "Mass Spectrometry Reviews 9, 505–554 (1990).

However, nucleic acids are very polar biopolymers that are very difficult to volatilize. Consequently, mass spectrometric detection has been limited to low molecular weight synthetic oligonucleotides by determining the mass of the parent molecular ion and through this, confirming the already known oligonucleotide sequence, or alternatively, confirming the known sequence through the generation of secondary ions (fragment ions) via CID in the MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Wolter et al. *Biomedical Environmental Mass Spectrometry* 14: 111–116 (1987)).

Two more recent ionizations/desorption techniques are electrospray/ionspray (ES) and matrix-assisted laser desorption/ionization (MALDI). ES mass spectrometry has been introduced by Yamashita et al. (*J. Phys. Chem.* 88: 4451–59 (1984); PCT Application No. WO 90/14148) and current applications are summarized in recent review articles (R. D. Smith et al., *Anal. Chem.* 62: 882–89 (1990) and B. Ardrey, Electrospray Mass Spectrometry, *Spectroscopy Europe* 4: 10–18 (1992)). The molecular weights of a tetradecanucleotide (Covey et al. "The Determination of Protein, Oligonucleotide and Peptide Molecular Weights by Ionspray Mass Spectrometry," *Rapid Communications in Mass Spectrometry* 2: 249–256 (1988)), and of a 21-mer (*Methods in Enzymology* 193, "Mass Spectrometry" (McCloskey, editor), p. 425, 1990, Academic Press, New York) have been published. As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp et al. ("Matrix Assisted UV-Laser Desorption/Ionization: A New Approach to Mass Spectrometry of Large Biomolecules," *Biological Mass Spectrometry* (Burlingame and McCloskey, editors), Elsevier Science Publishers, Amsterdam, pp. 49–60, 1990). Since, in most cases, no multiple molecular ion peaks are produced with this technique, the mass spectra, in principle, look simpler compared to ES mass spectrometry.

Although DNA molecules up to a molecular weight of 410,000 daltons have been desorbed and volatilized (Nelson et al., "Volatilization of High Molecular Weight DNA by Pulsed Laser Ablation of Frozen Aqueous Solutions, *Science* 246: 1585–87 (1989)), this technique has so far only shown very low resolution (oligothymidylic acids up to 18 nucleotides, Huth-Fehre et al., *Rapid Communications in Mass Spectrometry* 6: 209–13 (1992); DNA fragments up to 500 nucleotidase in length, Tang, K. et al., *Rapid Communications in Mass Spectrometry* 8: 727–730 (1994); and a double-stranded DNA of 28 base pairs (Williams et al., "Time-of Flight Mass Spectrometry of Nucleic Acids by Laser Ablation and Ionization from a Frozen Aqueous Matrix," *Rapid Communications in Mass Spectrometry* 4: 348–351 (1990)).

Japanese Patent No. 59-131909 describes an instrument, which detects nucleic acid fragments separated either by electrophoresis, liquid chromatography or high speed gel filtration. Mass spectrometric detection is achieved by incorporating into the nucleic acids, atoms which normally do not occur in DNA such as S, Br, I or Ag, Au, Pt, Os, Hg.

SUMMARY OF THE INVENTION

The instant invention provides mass spectrometric processes for detecting a particular nucleic acid sequence in a biological sample. Depending on the sequence to be detected, the processes can be used, for example, to diagnose (e.g. prenatally or postnatally) a genetic disease or chromosomal abnormality; a predisposition to a disease or condition (e.g. obesity, atherosclerosis, cancer), or infection by a pathogenic organism (e.g. virus, bacteria, parasite or fungus); or to provide information relating to identity, heredity, or compatibility (e.g. HLA phenotyping).

In a first embodiment, a nucleic acid molecule containing the nucleic acid sequence to be detected (i.e. the target) is initially immobilized to a solid support. Immobilization can be accomplished, for example, based on hybridization between a portion of the target nucleic acid molecule, which is distinct from the target detection site and a capture nucleic acid molecule, which has been previously immobilized to a solid support. Alternatively, immobilization can be accomplished by direct bonding of the target nucleic acid molecule and the solid support. Preferably, there is a spacer (e.g. a nucleic acid molecule) between the target nucleic acid molecule and the support. A detector nucleic acid molecule (e.g. an oligonucleotide or oligonucleotide mimetic), which is complementary to the target detection site can then be contacted with the target detection site and formation of a duplex, indicating the presence of the target detection site can be detected by mass spectrometry. In preferred embodiments, the target detection site is amplified prior to detection and the nucleic acid molecules are conditioned. In a further preferred embodiment, the target detection sequences are arranged in a format that allows multiple simultaneous detections (multiplexing), as well as parallel processing using oligonucleotide arrays ("DNA chips").

In a second embodiment, immobilization of the target nucleic acid molecule is an optional rather than a required step. Instead, once a nucleic acid molecule has been obtained from a biological sample, the target detection sequence is amplified and directly detected by mass spectrometry. In preferred embodiments, the target detection site and/or the detector oligonucleotides are conditioned prior to mass spectrometric detection. In another preferred embodiment, the amplified target detection sites are arranged in a format that allows multiple simultaneous detections (multiplexing), as well as parallel processing using oligonucleotide arrays ("DNA chips").

In a third embodiment, nucleic acid molecules which have been replicated from a nucleic acid molecule obtained from a biological sample can be specifically digested using one or more nucleases (using deoxyribonucleases for DNA or ribonucleases for RNA) and the fragments captured on a solid support carrying the corresponding complementary sequences. Hybridization events and the actual molecular weights of the captured target sequences provide information on whether and where mutations in the gene are present. The array can be analyzed spot by spot using mass spectrometry. DNA can be similarly digested using a cocktail of nucleases including restriction endonucleases. In a preferred embodiment, the nucleic acid fragments are conditioned prior to mass spectrometric detection.

In a fourth embodiment, at least one primer with 3' terminal base complementarity to a an allele (mutant or normal) is hybridized with a target nucleic acid molecule, which contains the allele. An appropriate polymerase and a complete set of nucleoside triphosphates or only one of the nucleoside triphosphates are used in separate reactions to furnish a distinct extension of the primer. Only if the primer is appropriately annealed (i.e. no 3' mismatch) and if the correct (i.e. complementary) nucleotide is added, will the primer be extended. Products can be resolved by molecular weight shifts as determined by mass spectrometry.

In a fifth embodiment, a nucleic acid molecule containing the nucleic acid sequence to be detected (i.e. the target) is initially immobilized to a solid support. Immobilization can be accomplished, for example, based on hybridization between a portion of the target nucleic acid molecule, which is distinct from the target detection site and a capture nucleic acid molecule, which has been previously immobilized to a solid support. Alternatively, immobilization can be accomplished by direct bonding of the target nucleic acid molecule and the solid support. Preferably, there is a spacer (e.g. a nucleic acid molecule) between the target nucleic acid molecule and the support. A nucleic acid molecule that is complementary to a portion of the target detection site that is immediately 5' of the site of a mutation is then hybridized with the target nucleic acid molecule. The addition of a complete set of dideoxynucleosides or 3'-deoxynucleoside triphosphates (e.g. pppAdd, pppTdd, pppCdd and pppGdd) and a DNA dependent DNA polymerase allows for the addition only of the one dideoxynucleoside or 3'-deoxynucleoside triphosphate that is complementary to X. The hybridization product can then be detected by mass spectrometry.

In a sixth embodiment, a target nucleic acid is hybridized with a complementary oligonucleotides that hybridize to the target within a region that includes a mutation M. The heteroduplex is than contacted with an agent that can specifically cleave at an unhybridized portion (e.g. a single strand specific endonuclease), so that a mismatch, indicating the presence of a mutation, results in a the cleavage of the target nucleic acid. The two cleavage products can then be detected by mass spectrometry.

In a seventh embodiment, which is based on the ligase chain reaction (LCR), a target nucleic acid is hybridized with a set of ligation educts and a thermostable DNA ligase, so that the ligase educts become covalently linked to each other, forming a ligation product. The ligation product can then be detected by mass spectrometry and compared to a known value. If the reaction is performed in a cyclic manner, the ligation product obtained can be amplified to better facilitate detection of small volumes of the target nucleic acid. Selection between wildtype and mutated primers at the ligation point can result in a detection of a point mutation.

The processes of the invention provide for increased accuracy and reliability of nucleic acid detection by mass spectrometry. In addition, the processes allow for rigorous controls to prevent false negative or positive results. The processes of the invention avoid electrophoretic steps, labeling and subsequent detection of a label. In fact it is estimated that the entire procedure, including nucleic acid isolation, amplification, and mass spec analysis requires only about 2–3 hours time. Therefore the instant disclosed processes of the invention are faster and less expensive to perform than existing DNA detection systems. In addition, because the instant disclosed processes allow the nucleic acid fragments to be identified and detected at the same time by their specific molecular weights (an unambiguous physical standard), the disclosed processes are also much more accurate and reliable than currently available procedures.

BRIEF DESCRIPTION OF THE FIGURES

FIG. 6A is a diagram showing mass spectrometric analysis of a nucleic acid molecule, which has been amplified by a transcription amplification procedure. An RNA sequence is captured via its TCS sequence, so that wildtype and mutated target detection sites can be detected as above by employing appropriate detector oligonucleotides (D).

FIG. 6B is a diagram showing multiplexing to detect two different (mutated) sites on the same RNA in a simultaneous fashion using mass-modified detector oligonucleotides M1–D1 and M2–D2.

FIG. 6C is a diagram of a different multiplexing procedure for detection of specific mutations by employing mass modified dideoxynucleoside or 3'-deoxynucleoside triphosphates and an RNA dependent DNA polymerase. Alternatively, DNA dependent RNA polymerase and ribonucleotide triphosphates can be employed. This format allows for simultaneous detection of all four base possibilities at the site of a mutation (X).

FIG. 10A-1 shows the absorbance or the 26-mer before hybridization. FIG. 10A-2 shows the filtrate of the centrifugation after hybridization. FIG. 10A-3 shows the results after the first wash with 50 mM ammonium citrate. FIG. 10A-4 shows the results after the second wash with 50 mM ammonium citrate.

FIG. 34A is a schematic representation of the oligo base extension of the mutation detection primer b using ddTTP. FIG. 34B is a schematic representation of the oligo base extension of the mutation detection primer b using ddCTP. The theoretical mass calculation is given in parenthesis. The sequence shown is part of the exon 10 of the CFTR gene that bears the most common cystic fibrosis mutation ΔF508 and more rare mutations ΔI507 as well at Ile506Ser.

unmodified and 7-deazapurine modified 99-mer (173216 and 94400 counts).

Figure 40A:
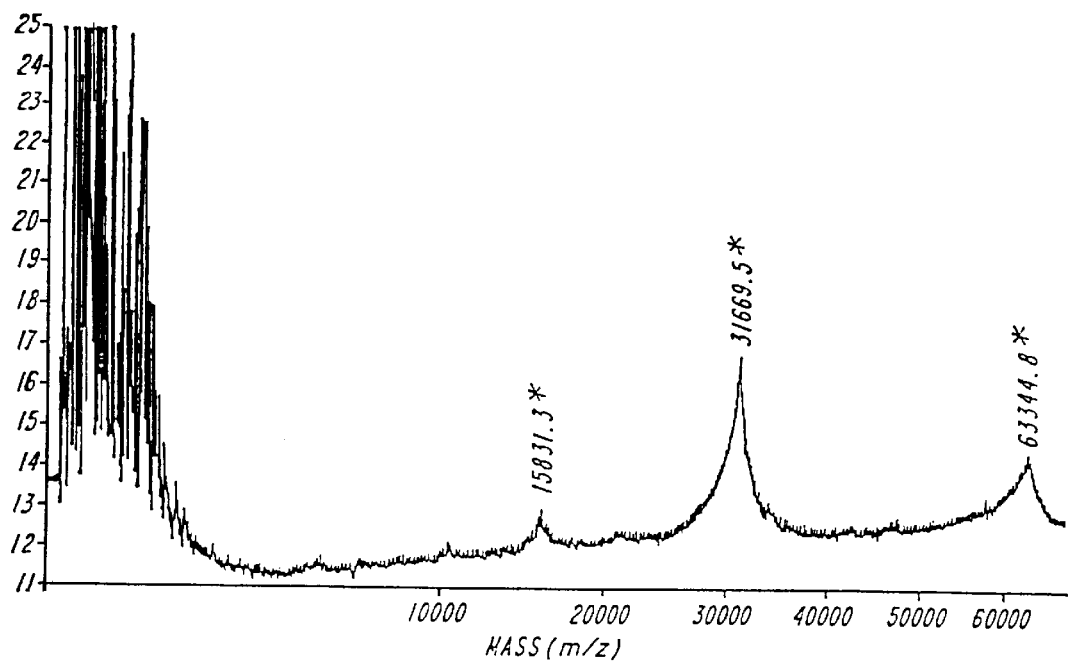
Figure 40B:
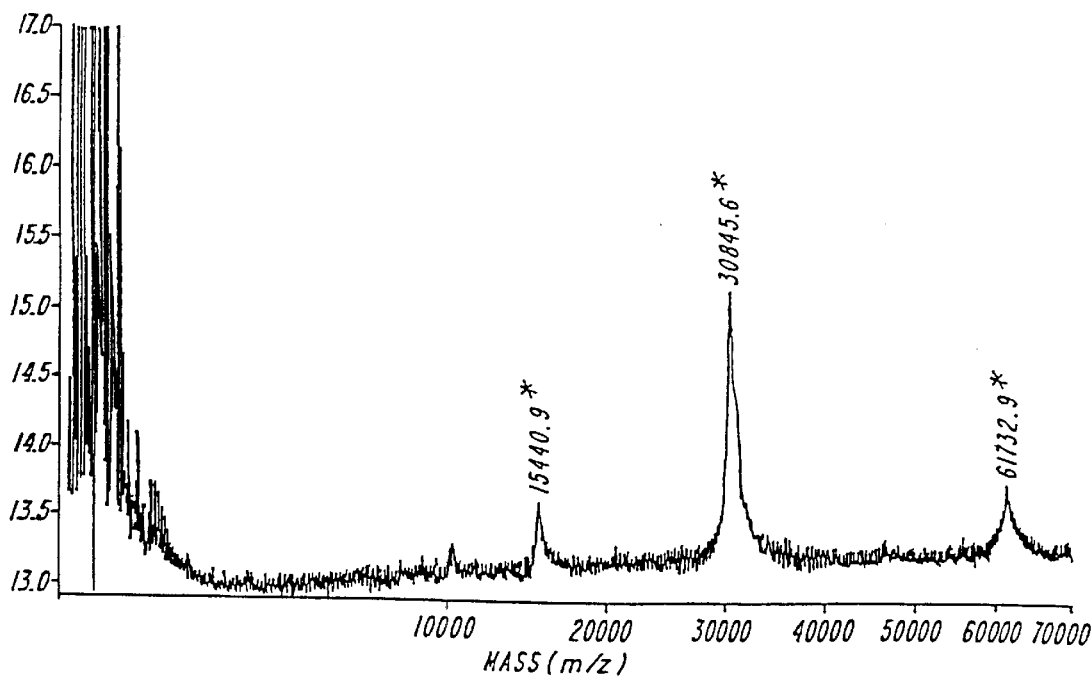

FIG. 40A shows a MALDI-TOF mass spectrum of the unmodified 103-mer PCR products (sum of twelve single shot spectra). The mean value of the masses calculated for the two single strands (31768 u and 31759 u) is 31763 u. Mass resolution: 18. FIG. 40B shows a MALDI-TOF mass spectrum of 7-deazapurine containing 103-mer PCR product (sum of three single shot spectra). The mean value of the masses calculated for the two single strands (31727 u and 31719 u) is 31723 u. Mass resolution: 67.

Figure 41A:
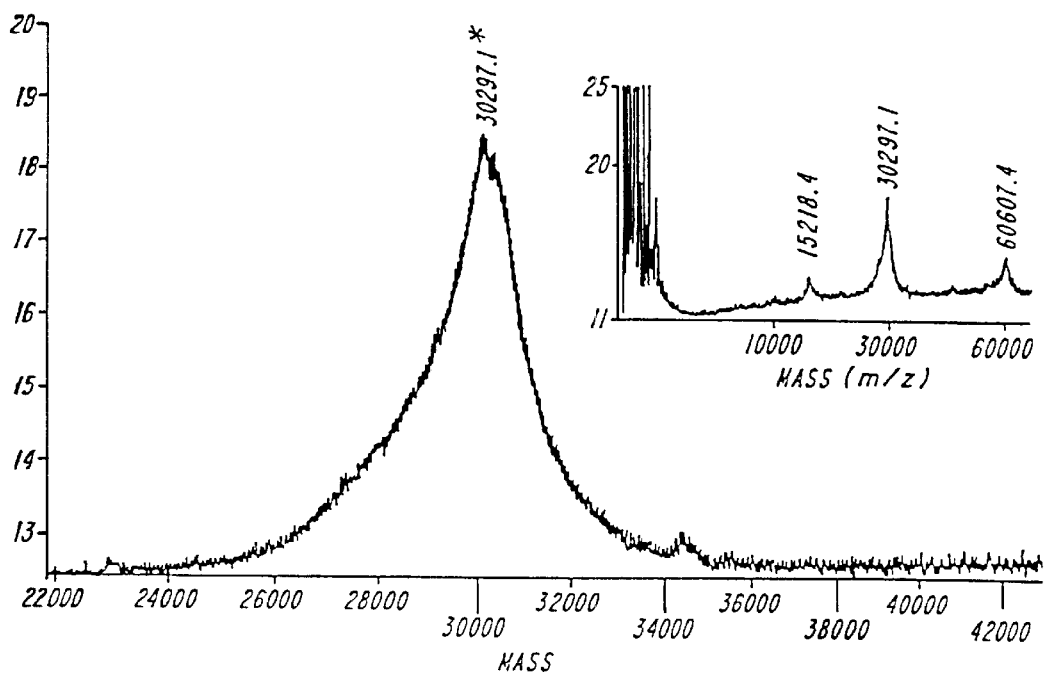
Figure 41B:
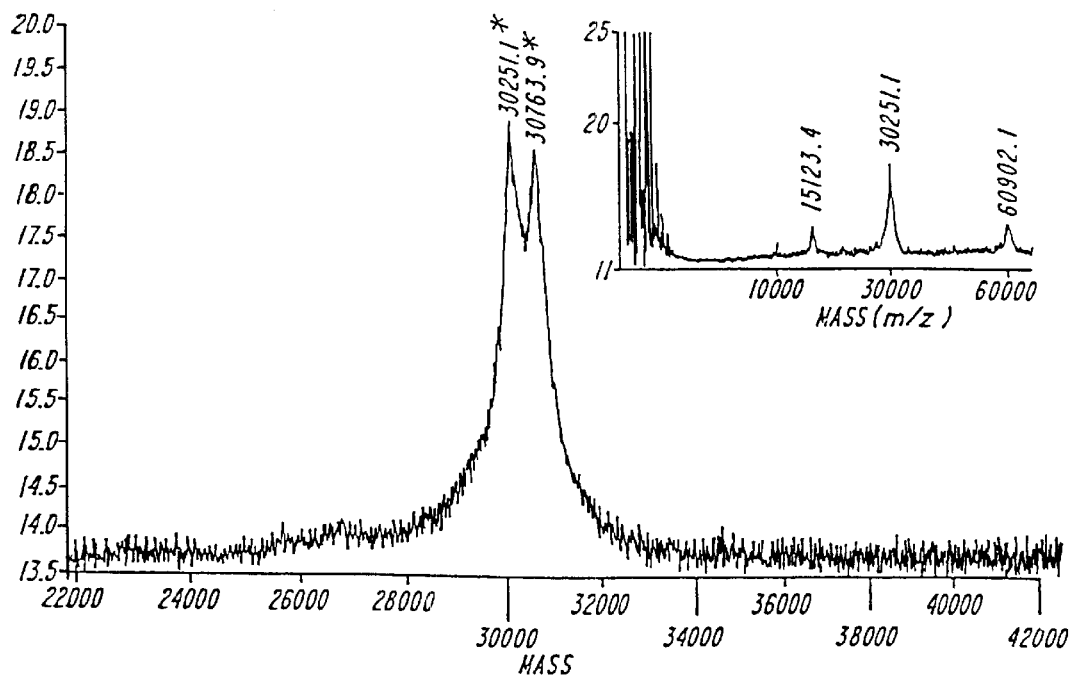

FIG. 41A shows a MALDI-TOF mass spectrum of the unmodified 99-mer PCR product (sum of twenty single shot spectra). Values of the masses calculated for the two single strands: 30261 u and 30794 u. FIG. 41B shows a MALDI-TOF mass spectrum of the 7deazapurine containing 99-mer PCR product (sum of twelve single shot spectra). Values of the masses calculated for the two single strands: 30224 u and 30750 u.

Figure 42A:
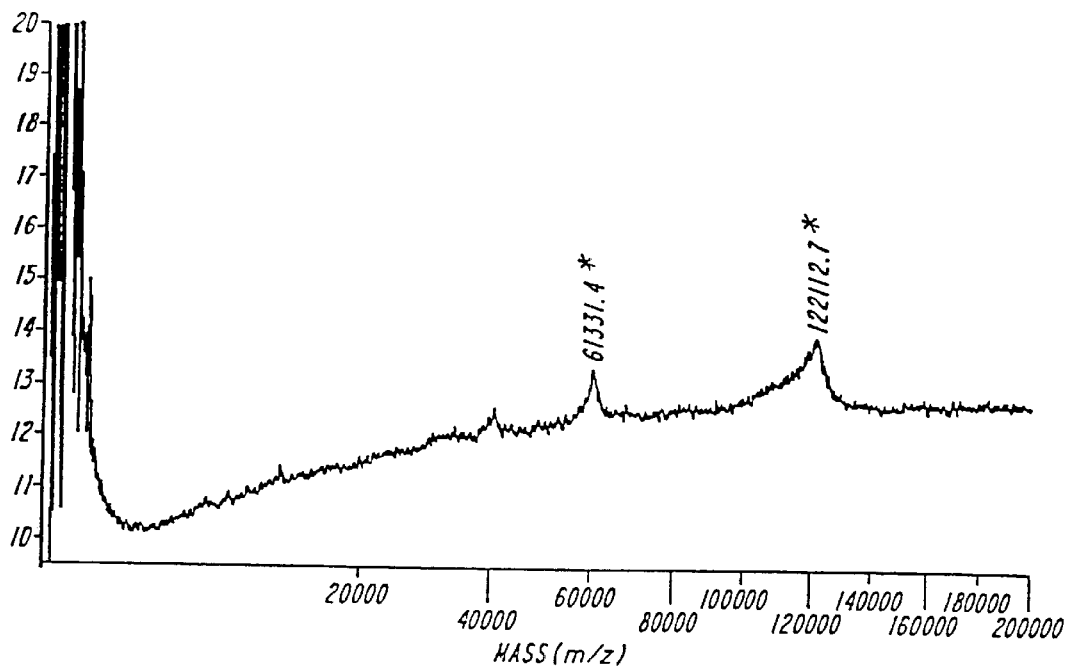
Figure 42B:
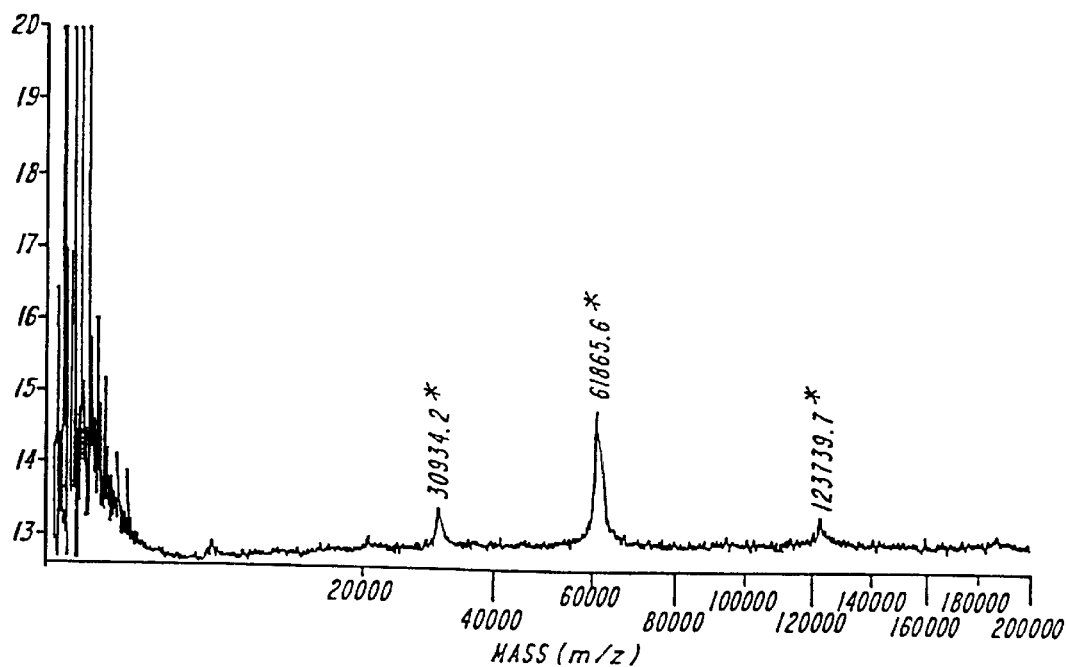

FIG. 42A shows a MALDI-TOF mass spectrum of the unmodified 200-mer PCR product (sum of 30 single shot spectra). The mean value of the masses calculated for the two single strands (61873 u and 61595 u) is 61734 u. Mass resolution: 28. FIG. 42B shows a MALDI-TOF mass spectrum of 7-deazapurine containing 200-mer PCR product (sum of 30 single shot spectra). The mean value of the masses calculated for the two single strands (61772 u and 61514 u) is 61643 u. Mass resolution: 39.

Figure 43A:
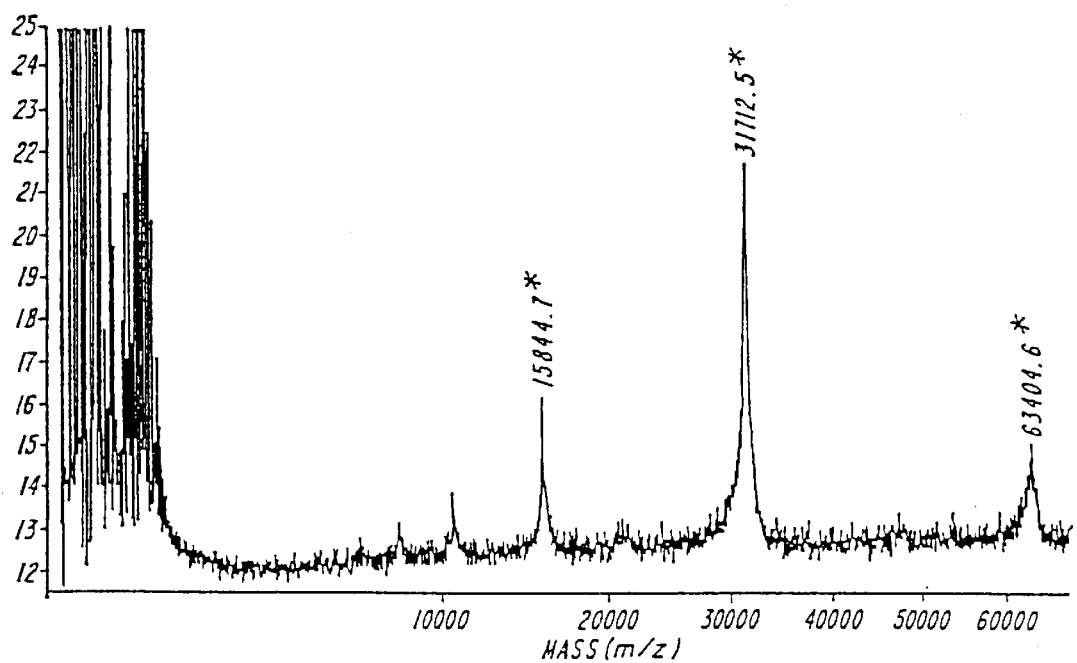
Figure 43B:
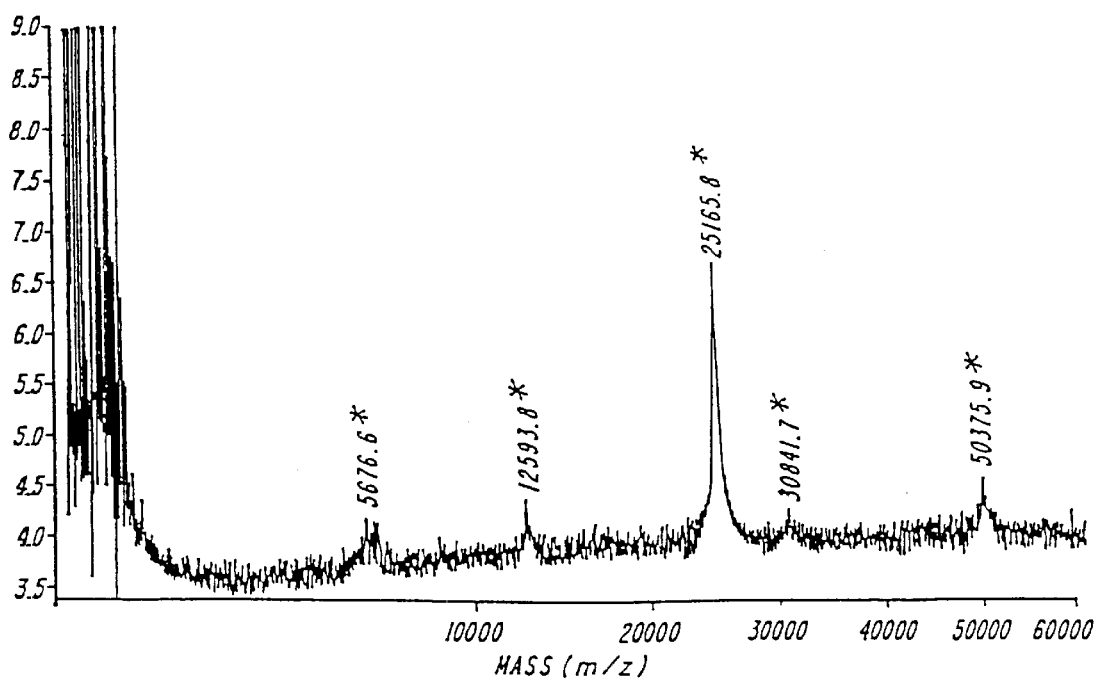
Figure 44A:
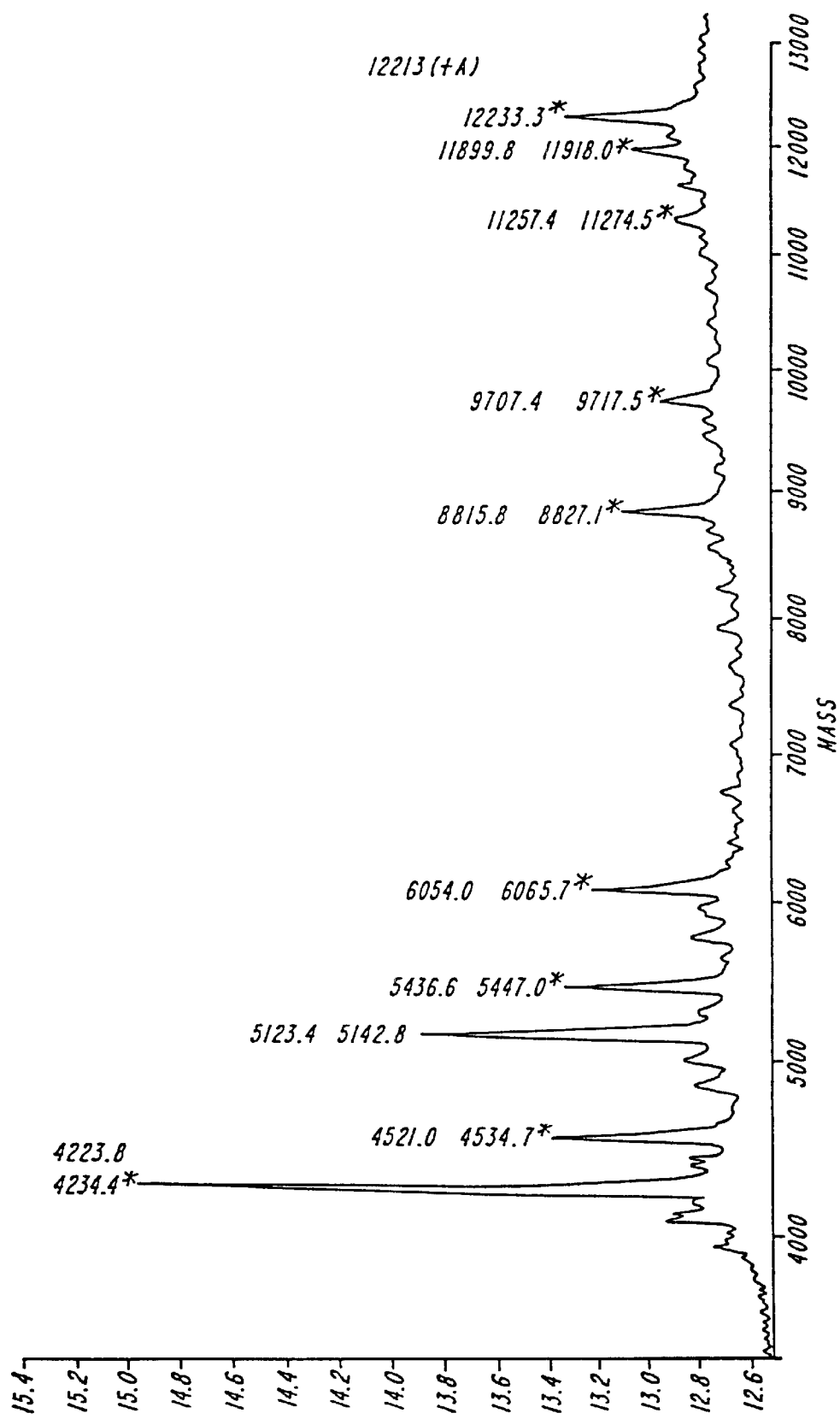
Figure 44B:
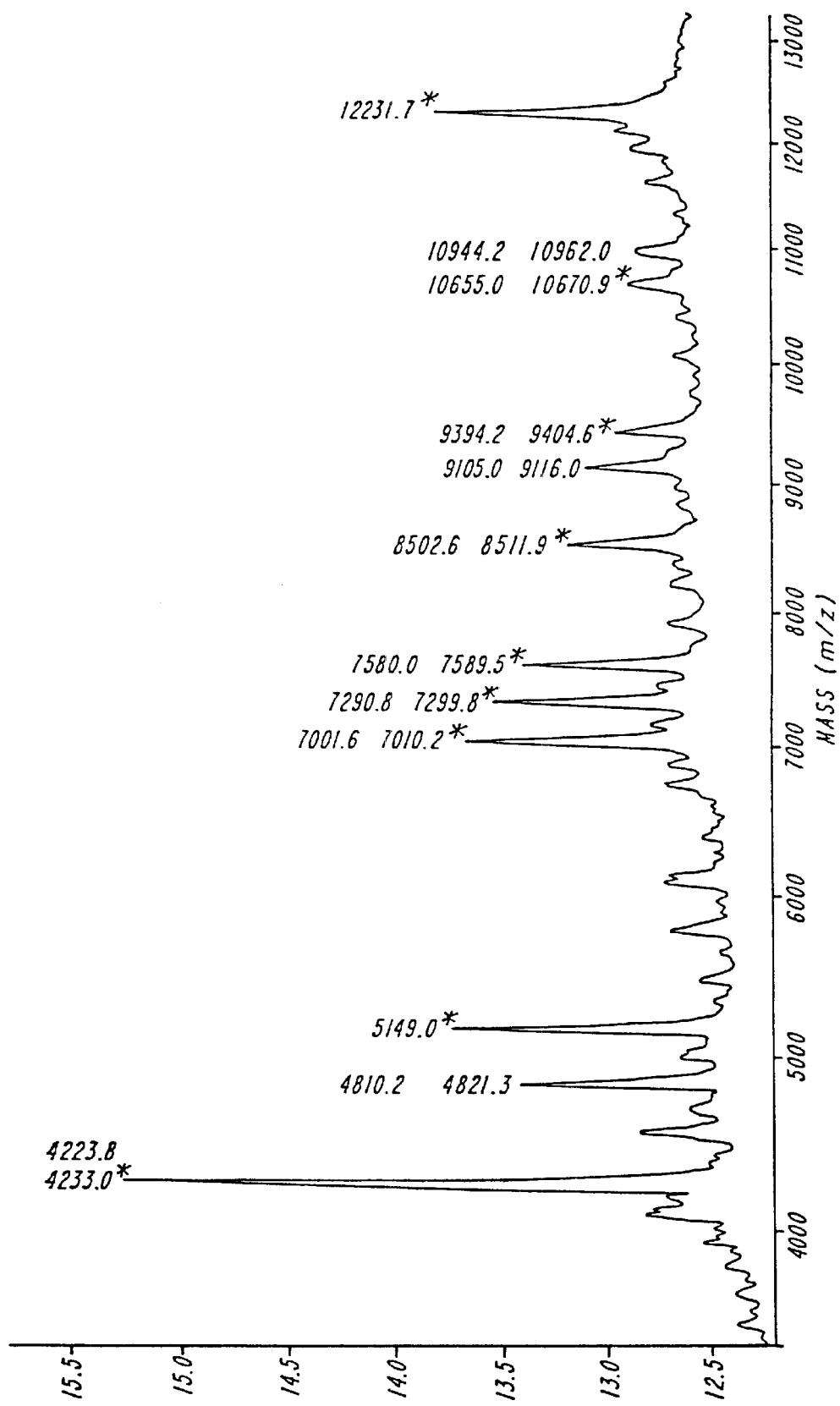
Figure 44C:
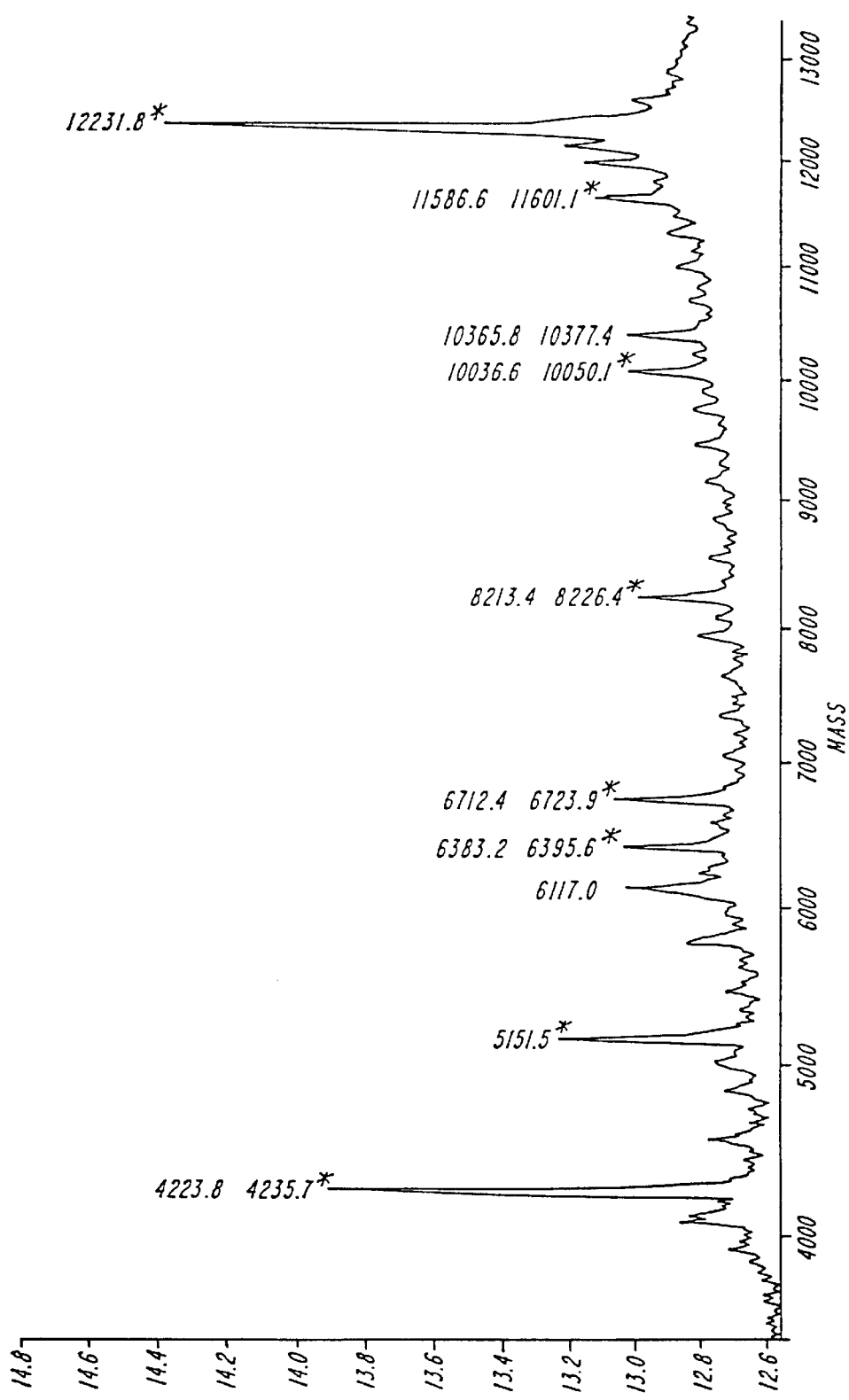
Figure 44D:
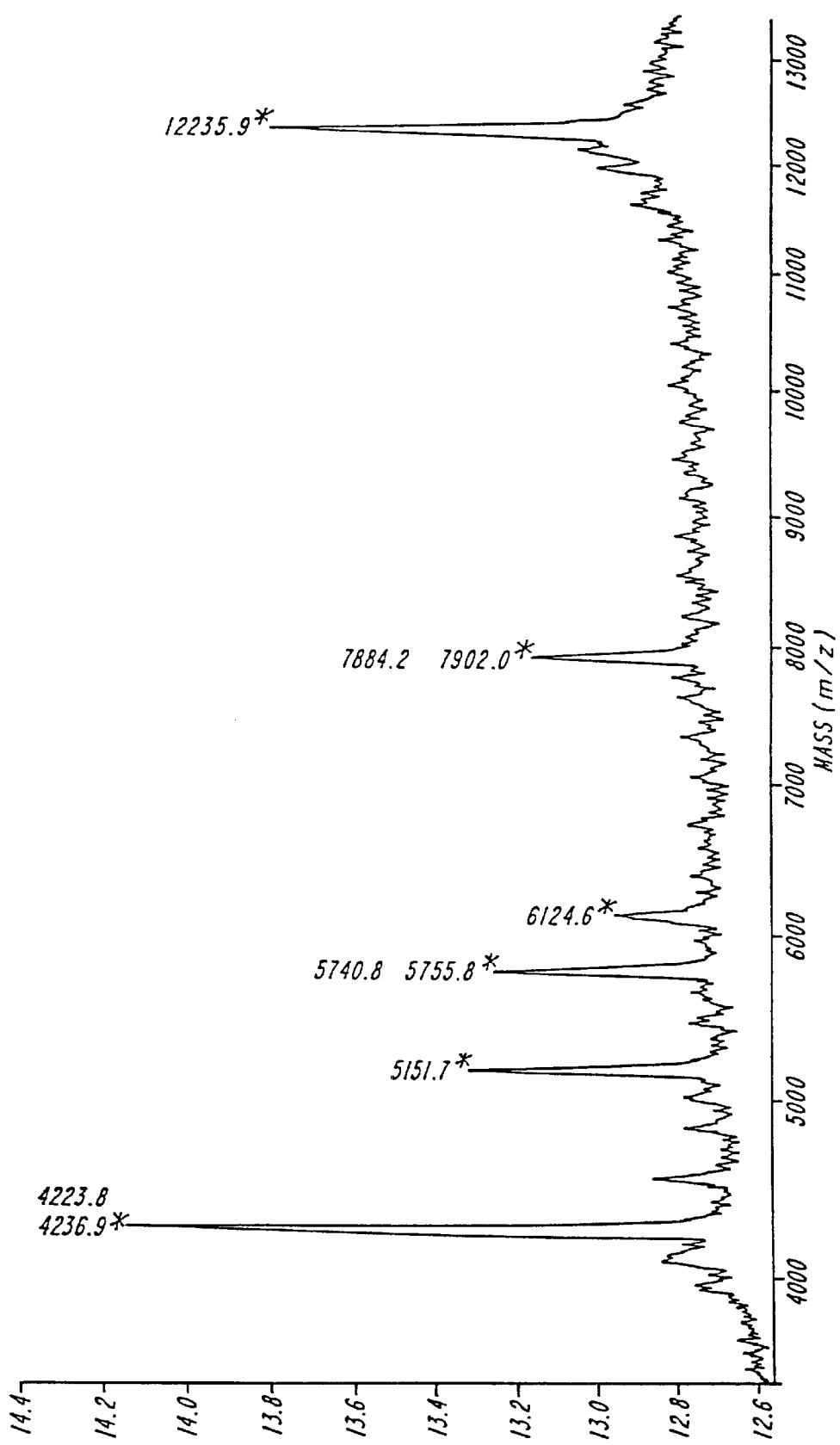

FIG. 43A shows a MALDI-TOF mass spectrum of 7-deazapurine containing 100-mer PCR product with ribomodified primers. The mean value of the masses calculated for the two single strands (30529 u and 31095 u) is 30812 u. FIG. 43B shows a MALDI-TOF mass spectrum of the PCR-product after hydrolytic primer-cleavage. The mean value of the masses calculated for the two single strands (25104 u and 25229 u) is 25167 u. The mean value of the cleaved primers (5437 u and 5918 u) is 5677 u.

FIGS. 44A–D show the MALDI-TOF mass spectrum of the four sequencing ladders obtained from a 39-mer template (SEQ. ID. No. 13), which was immobilized to streptavidin beads via a 3' biotinylation. A 14-mer primer (SEQ. ID. No. 14) was used in the sequencing.

Figure 45:
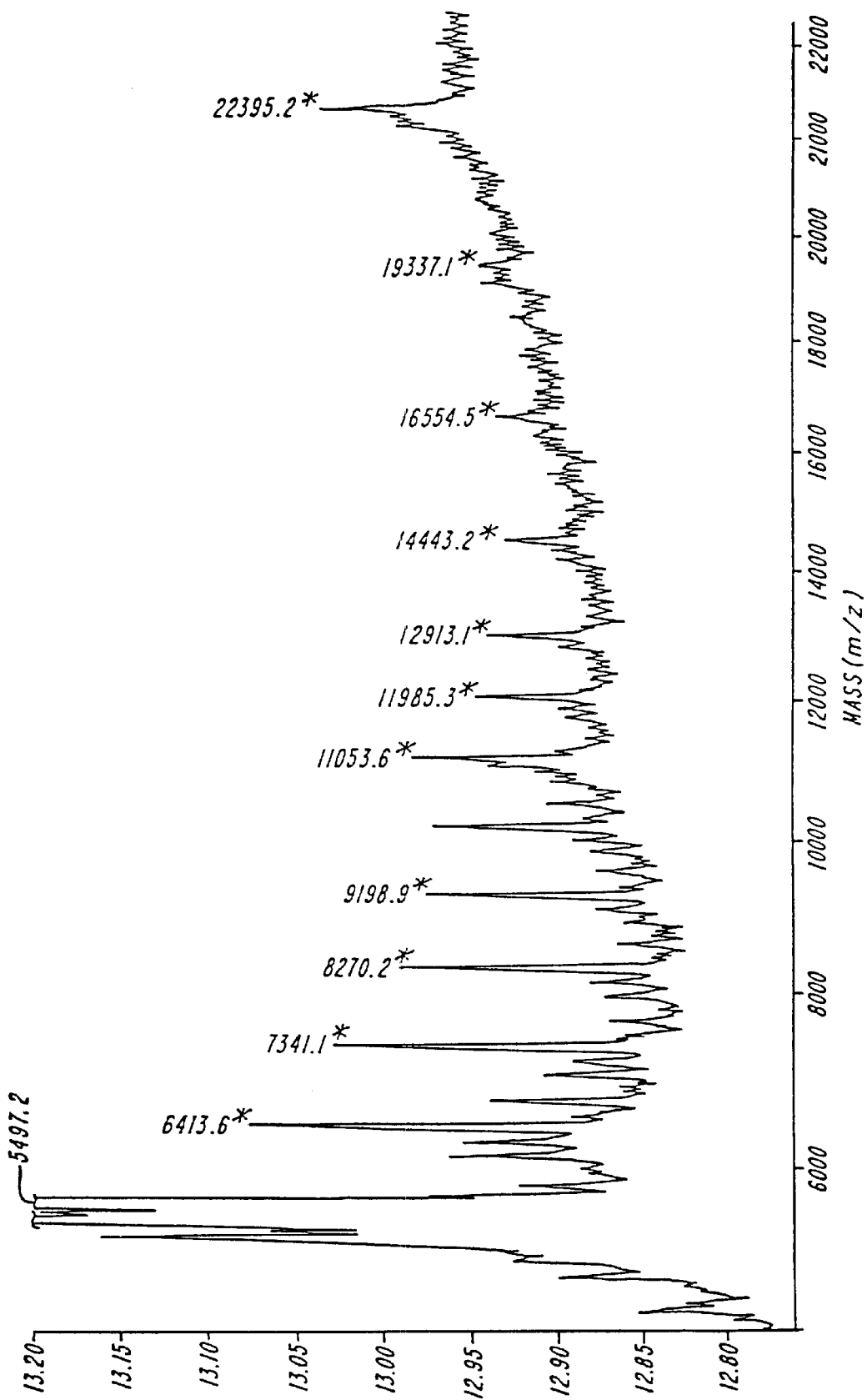

FIG. 45 shows a MALDI-TOF mass spectrum of a solid state sequencing of a 78-mer template (SEQ. ID. No. 15), which was immobilized to streptavidin beads via a 3' biotinylation. A 18-mer primer (SEQ. ID. No. 16) and ddGTP were used in the sequencing.

Figure 46:
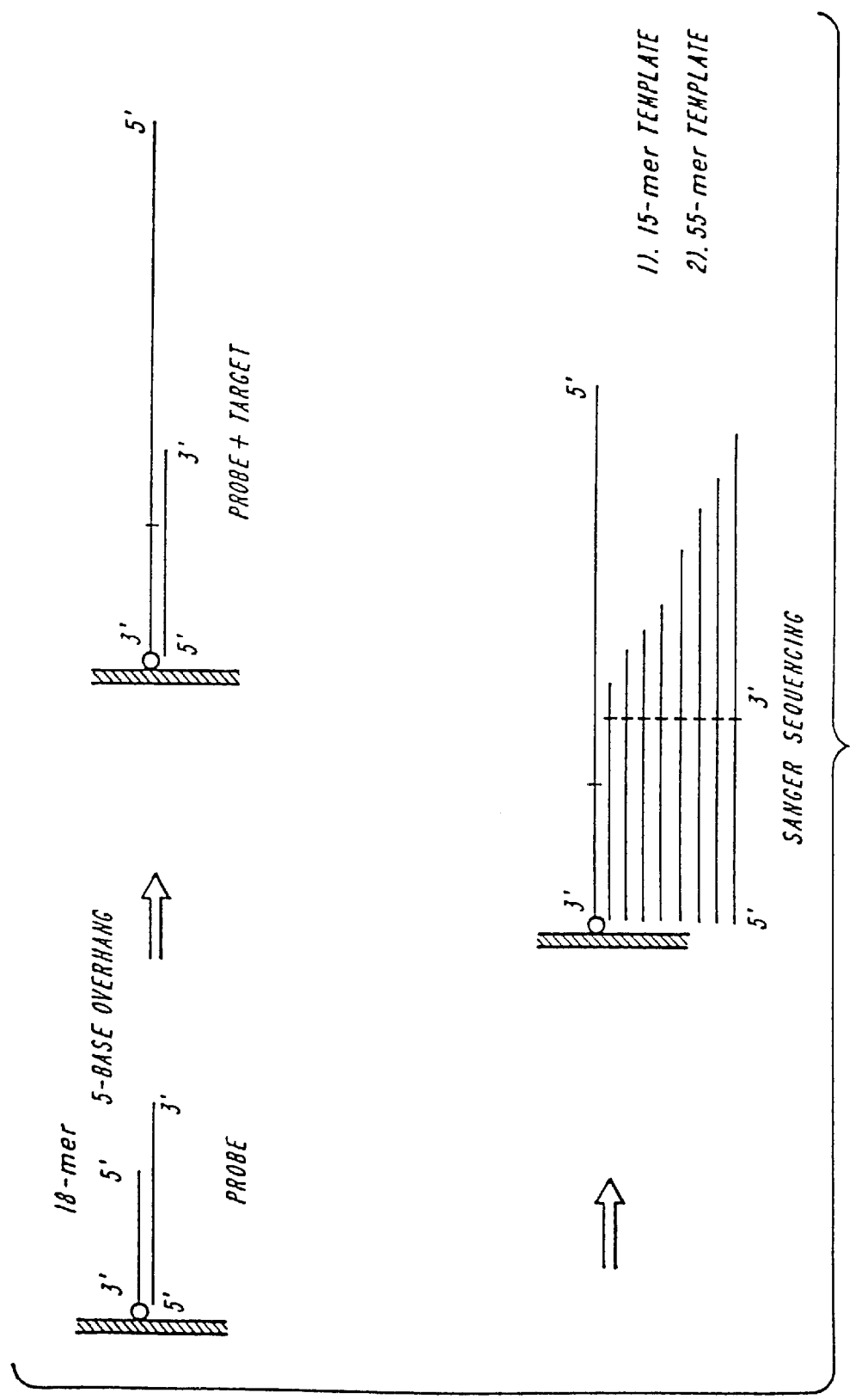
Figure 47A:
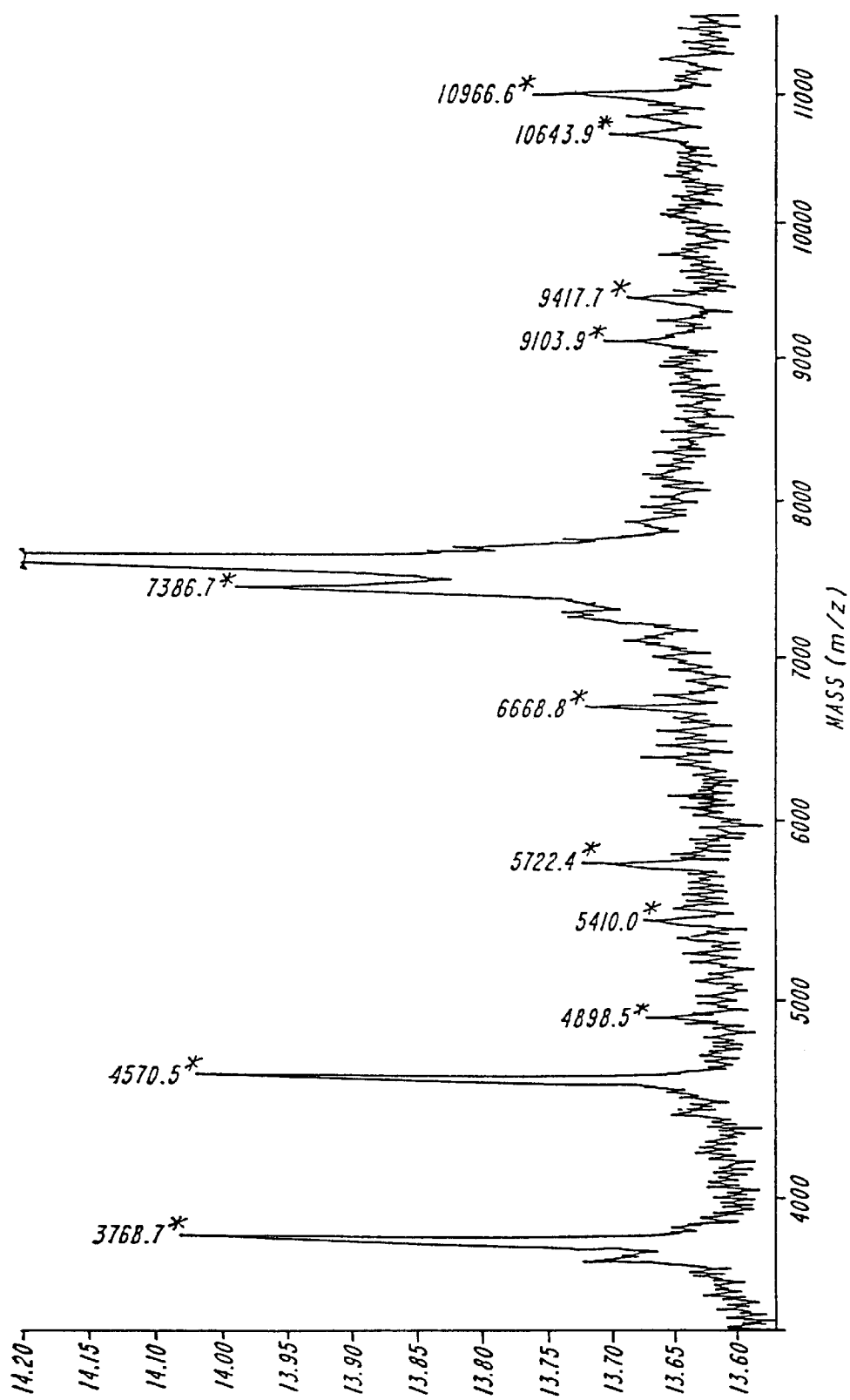
Figure 47B:
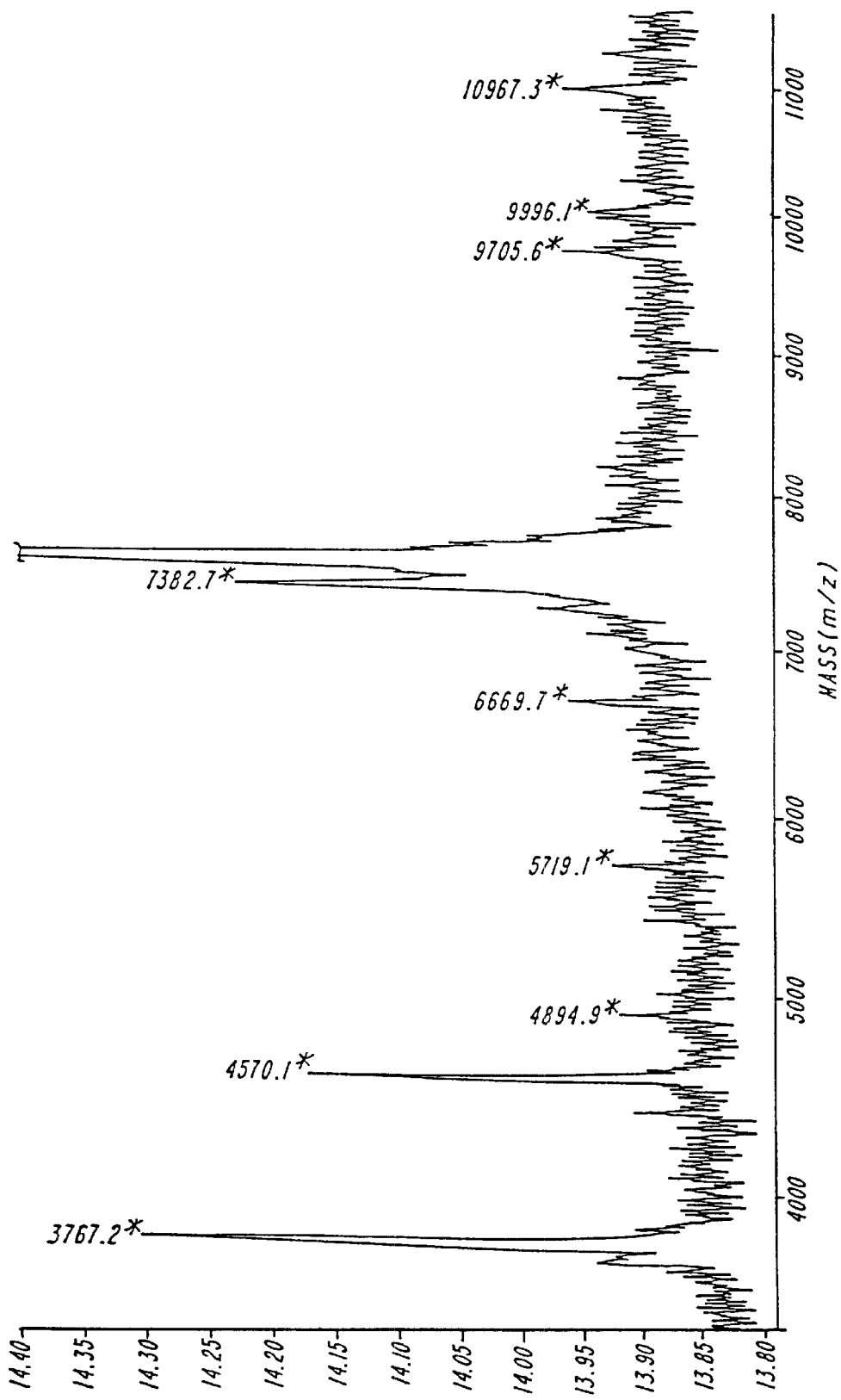
Figure 47C:
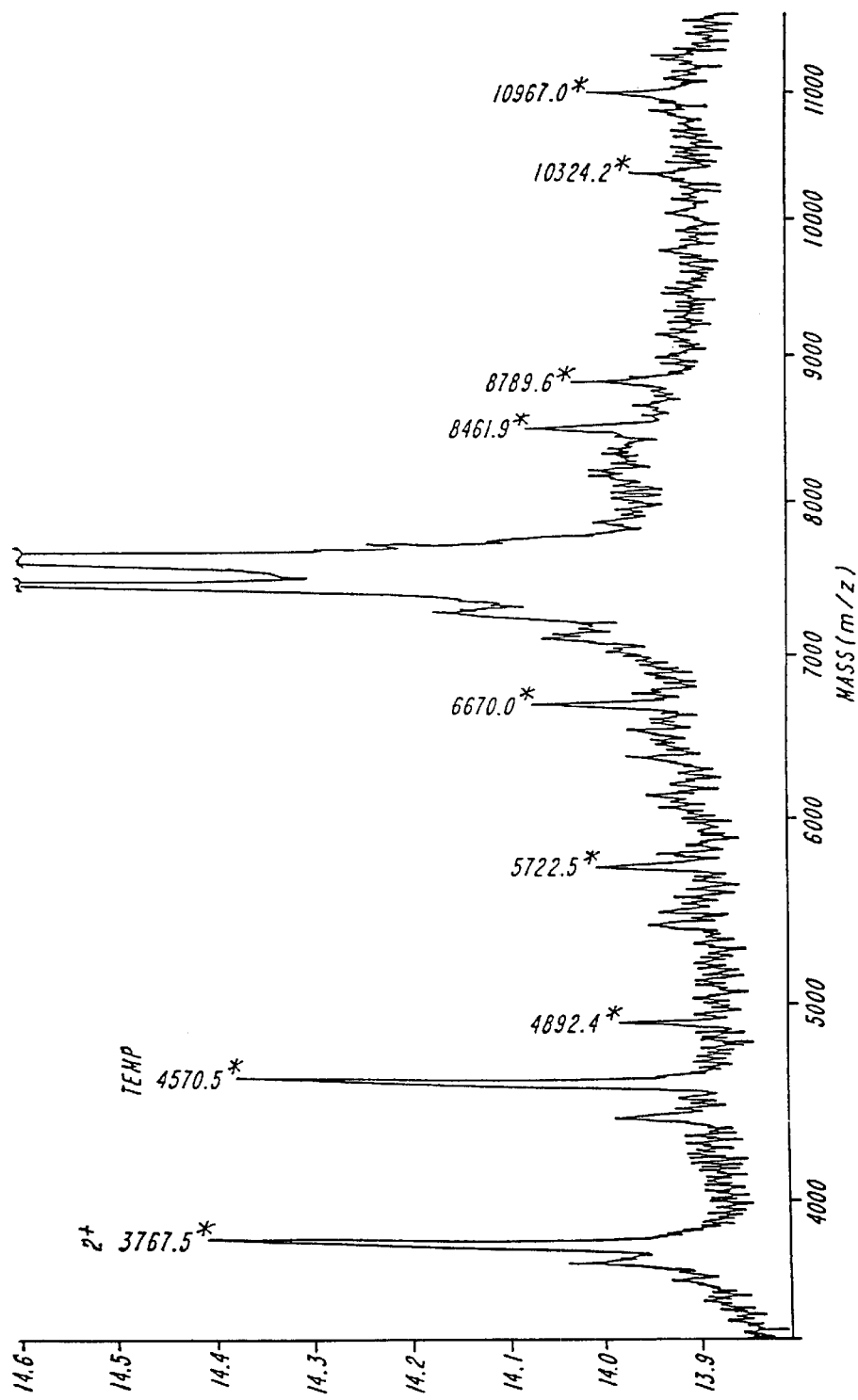
Figure 47D:
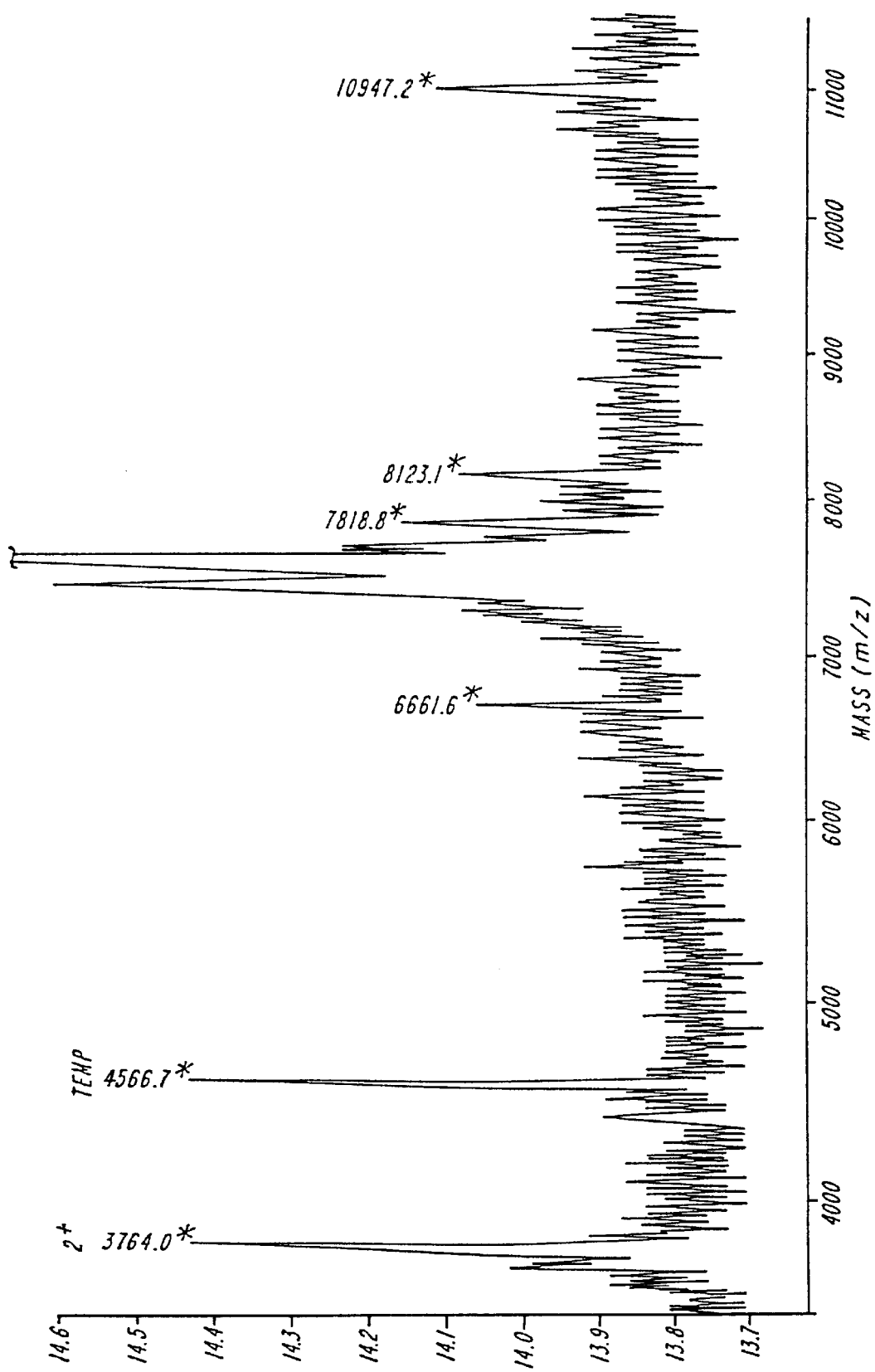
Figures 48A, 48B, 48C, 48D:
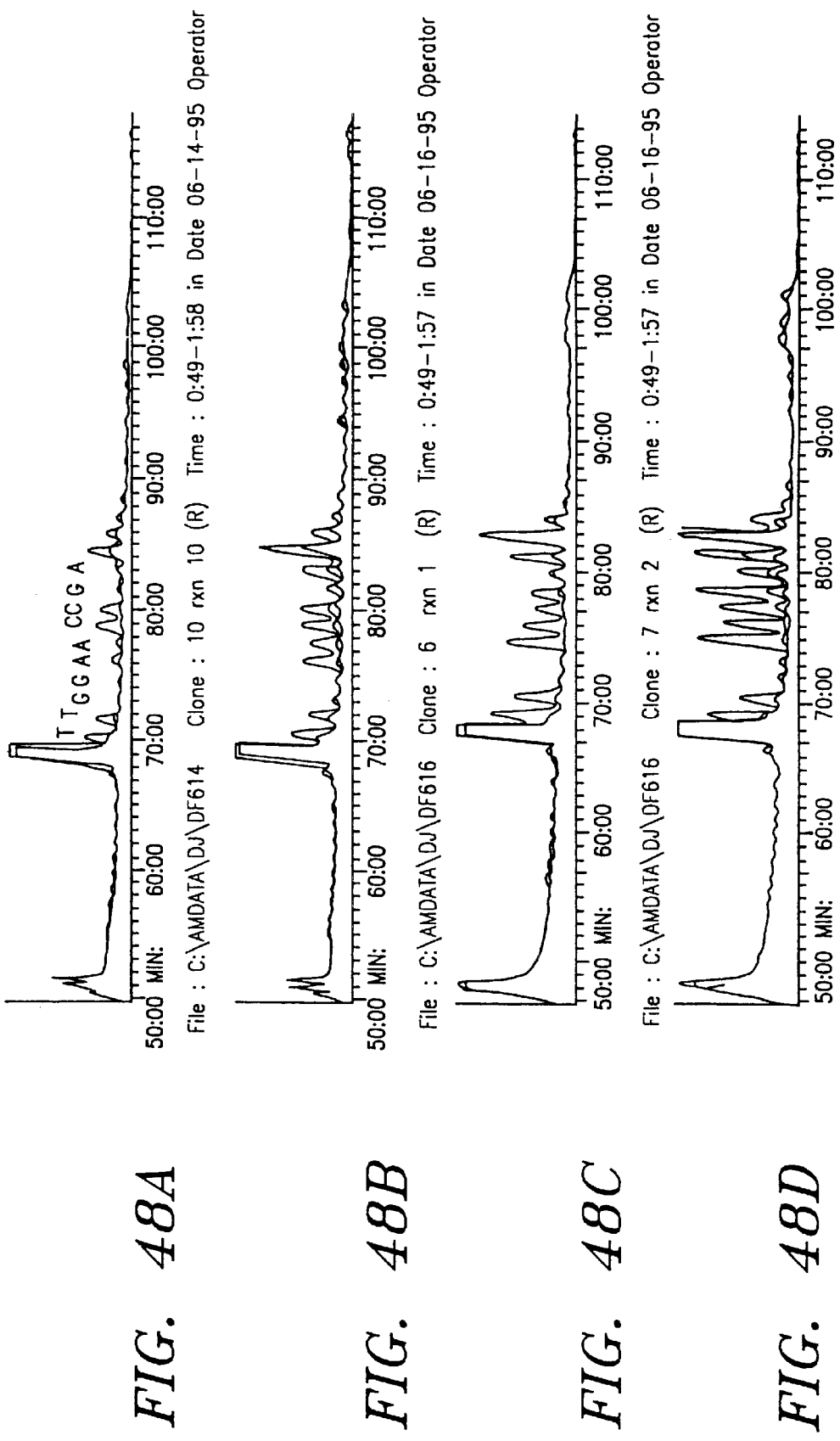

FIG. 46 shows a scheme in which duplex DNA probes with single-stranded overhang capture specific DNA templates and also serve as primers for solid state sequencing.

FIG. 47A–D shows MALDI-TOF mass spectra obtained from a 5' fluorescent labeled 23-mer (SEQ. ID. No. 19) annealed to an 3' biotinylated 18-mer (SEQ. ID. No. 20), leaving a 5-base overhang, which captured a 15-mer template (SEQ. ID. No. 21).

Figure 35A:
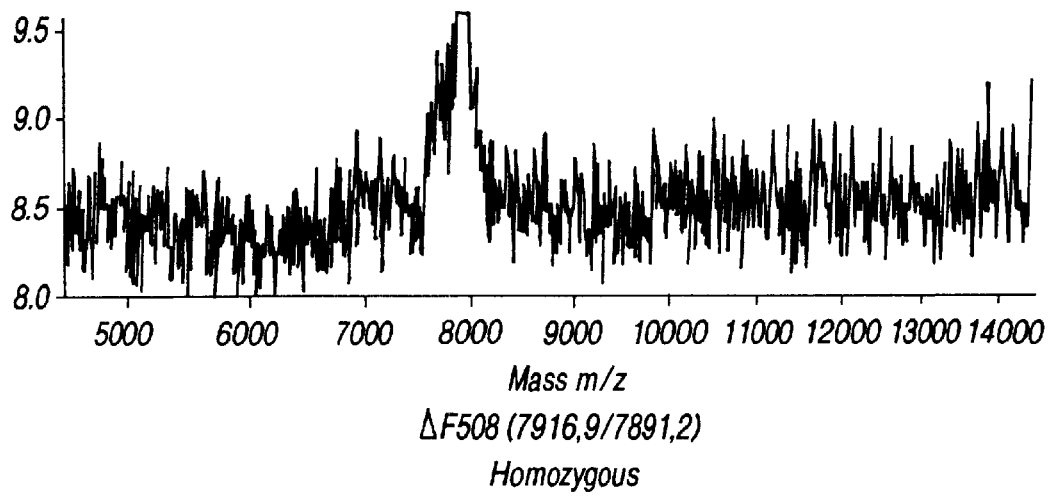
FIG. 35A is a MALDI-TOF-MS spectra recorded directly from precipitated oligo base extended primers for mutation detection using ddTTP.
Figure 35B:
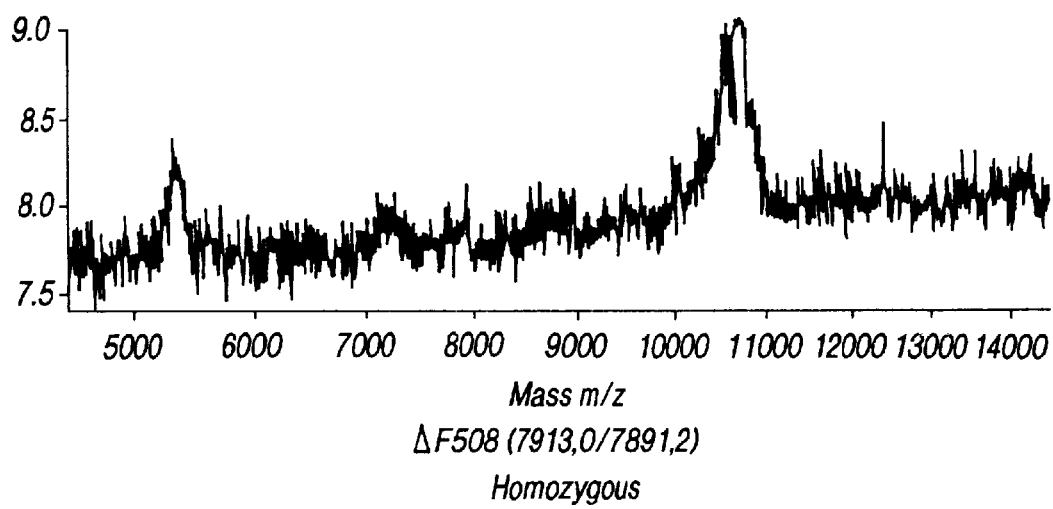
FIG. 35B is a MALDI-TOF-MS spectra recorded directly from precipitated oligo base extended primers for mutation detection using ddCTP. The spectra on the top of each panel (ddTTP or ddCTP, respectively) shows the annealed primer (CF508) without further extension reaction. The template of diagnosis is pointed out below each spectra and the observed/expected molecular mass are written in parenthesis.

FIGS. 48A–D show a stacking fluorogram of the same products obtained from the reaction described in FIG. 35, but run on a conventional DNA sequencer.

DETAILED DESCRIPTION OF THE INVENTION

In general, the instant invention provides mass spectrometric processes for detecting a particular nucleic acid sequence in a biological sample. As used herein, the term "biological sample" refers to any material obtained from any living source (e.g. human, animal, plant, bacteria, fungi, protist, virus). For use in the invention, the biological sample should contain a nucleic acid molecule. Examples of appropriate biological samples for use in the instant invention include: solid materials (e.g. tissue, cell pellets, biopsies) and biological fluids (e.g. urine, blood, saliva, amniotic fluid, mouth wash).

Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994).

To obtain an appropriate quantity of nucleic acid molecules on which to perform mass spectrometry, amplification may be necessary. Examples of appropriate amplification procedures for use in the invention include: cloning (Sambrook et al., *Molecular Cloning: A Laboratory Manual*, Cold Spring Harbor Laboratory Press, 1989), polymerase chain reaction (PCR) (C. R. Newton and A. Graham, PCR, BIOS Publishers, 1994); ligase chain reaction (LCR) (Wiedmann, M., et al., *PCR Methods Appl.* Vol. 3, pp. 57–64 (1994); F. Barnay, *Proc. Natl. Acad. Sci USA* 88: 189–93 (1991)); strand displacement amplification (SDA) (G. Terrance Walker et al., *Nucleic Acids Res.* 22: 2670–77 (1994)); and variations such as RT-PCR (Higuchi, et al., *Bio/Technology* 11:1026–1030 (1993)), allele-specific amplification (ASA) and transcription based processes.

To facilitate mass spectrometric analysis, a nucleic acid molecule containing a nucleic acid sequence to be detected can be immobilized to a solid support. Examples of appropriate solid supports include beads (e.g. silica gel, controlled pore glass, magnetic, Sephadex/Sepharose, cellulose), flat surfaces or chips (e.g. glass fiber filters, glass surfaces, metal surface (steel, gold, silver, aluminum, copper and silicon), capillaries, plastic (e.g. polyethylene, polypropylene, polyamide, polyvinylidenedifluoride membranes or microtiter plates)); or pins or combs made from similar materials comprising beads or flat surfaces or beads placed into pits in flat surfaces such as wafers (e.g. silicon wafers).

Figure 1A:
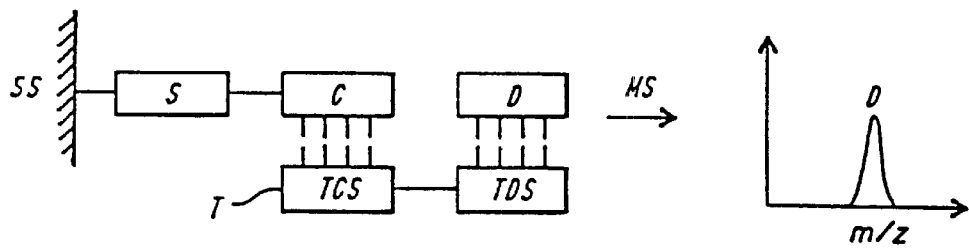
FIG. 1A is a diagram showing a process for performing mass spectrometric analysis on one target detection site (TDS) contained within a target nucleic acid molecule (T), which has been obtained from a biological sample. A specific capture sequence (C) is attached to a solid support (SS) via a spacer (S). The capture sequence is chosen to specifically hybridize with a complementary sequence on the target nucleic acid molecule (T), known as the target capture site (TCS). The spacer (S) facilitates unhindered hybridization. A detector nucleic acid sequence (D), which is complementary to the TDS is then contacted with the TDS. Hybridization between D and the TDS can be detected by mass spectrometry.

Immobilization can be accomplished, for example, based on hybridization between a capture nucleic acid sequence, which has already been immobilized to the support and a complementary nucleic acid sequence, which is also contained within the nucleic acid molecule containing the nucleic acid sequence to be detected (FIG. 1A). So that hybridization between the complementary nucleic acid molecules is not hindered by the support, the capture nucleic acid can include a spacer region of at least about five nucleotides in length between the solid support and the capture nucleic acid sequence. The duplex formed will be cleaved under the influence of the laser pulse and desorption can be initiated. The solid support-bound base sequence can be presented through natural oligoribo- or oligodeoxyribonucleotide as well as analogs (e.g. thio-modified phosphodiester or phosphotriester backbone) or employing oligonucleotide mimetics such as PNA analogs (see e.g. Nielsen et al., *Science*, 254, 1497 (1991)) which render the base sequence less susceptible to enzymatic degradation and hence increases overall stability of the solid support-bound capture base sequence.

Figure 1B:
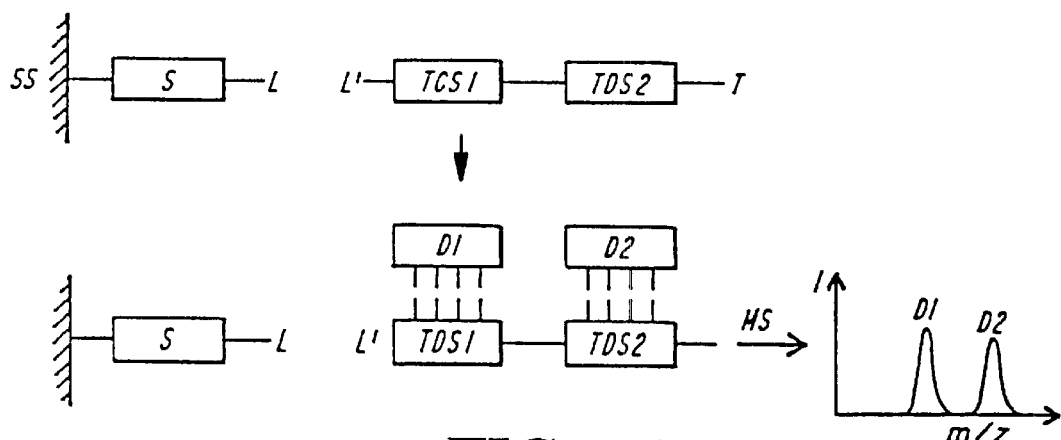
FIG. 1B is a diagram showing a process for performing mass spectrometric analysis on at least one target detection site (here TDS 1 and TDS 2) via direct linkage to a solid support. The target sequence (T) containing the target detection site (TDS 1 and TDS 2) is immobilized to a solid support via the formation of a reversible or irreversible bond formed between an appropriate functionality (L') on the target nucleic acid molecule (T) and an appropriate functionality (L) on the solid support. Detector nucleic acid sequences (here D1 and D2), which are complementary to a target detection site (TDS 1 or TDS 2) are then contacted with the TDS. Hybridization between TDS 1 and D1 and/or TDS 2 and D2 can be detected and distinguished based on molecular weight differences.

Alternatively, a target detection site can be directly linked to a solid support via a reversible or irreversible bond between an appropriate functionality (L') on the target nucleic acid molecule (T) and an appropriate functionality (L) on the capture molecule (FIG. 1B). A reversible linkage can be such that it is cleaved under the conditions of mass spectrometry (i.e., a photocleavable bond such as a charge transfer complex or a labile bond being formed between relatively stable organic radicals). Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L', by specific absorption of laser energy which is in resonance with the L' chromophore.

By way of example, the L–L' chemistry can be of a type of disulfide bond (chemically cleavable, for example, by mercaptoethanol or dithioerythritol), a biotin/streptavidin system, a heterobifunctional derivative of a trityl ether group (Gildea et al., "A Versatile Acid-Labile Linker for Modification of Synthetic Biomolecules," *Tetrahedron Letters* 31: 7095 (1990)) which can be cleaved under mildly acidic conditions as well as under conditions of mass spectrometry, a levulinyl group cleavable under almost neutral conditions with a hydrazinium/acetate buffer, an arginine-arginine or lysine-lysine bond cleavable by an endopeptidase enzyme like trypsin or a pyrophosphate bond cleavable by a pyrophosphatase, or a ribonucleotide bond in between the oligodeoxynucleotide sequence, which can be cleaved, for example, by a ribonuclease or alkali.

The functionalities, L and L', can also form a charge transfer complex and thereby form the temporary L–L' linkage. Since in many cases the "charge-transfer band" can be determined by UV/vis spectrometry (see e.g. *Organic Charge Transfer Complex* by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L–L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g., *Reactive Molecules* by C. Wentrup, John Wiley & Sons, 1984).

Figure 4:
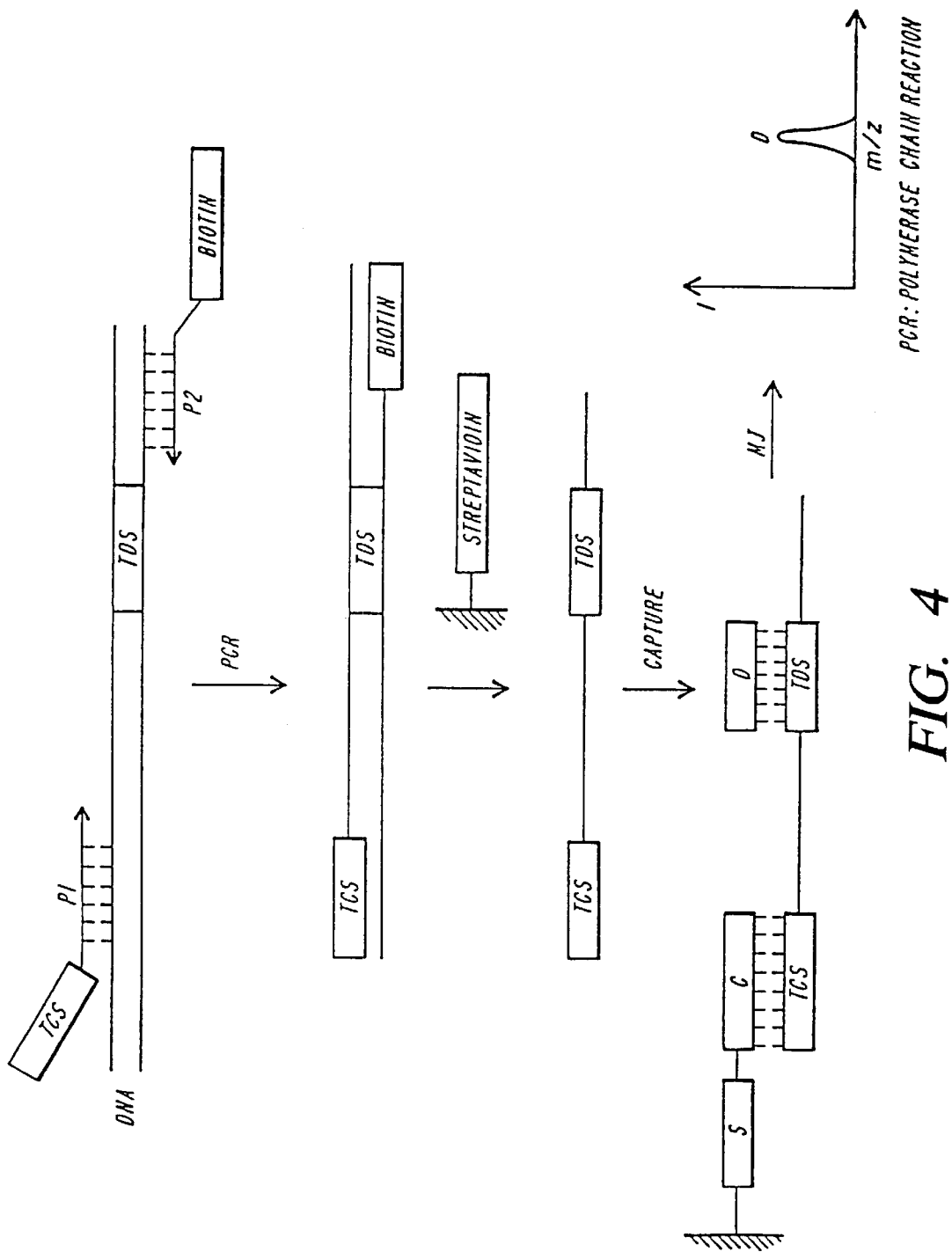
FIG. 4 is a diagram showing a format wherein a predesigned target capture site (TCS) is incorporated into the target sequence using PCR amplification. Only one strand is captured, the other is removed (e.g., based on the interaction between biotin and streptavidin coated magnetic beads). If the biotin is attached to primer 1 the other strand can be appropriately marked by a TCS. Detection is as described above through the interaction of a specific detector oligonucleotide D with the corresponding target detection site TDS via mass spectrometry.
Figure 5:
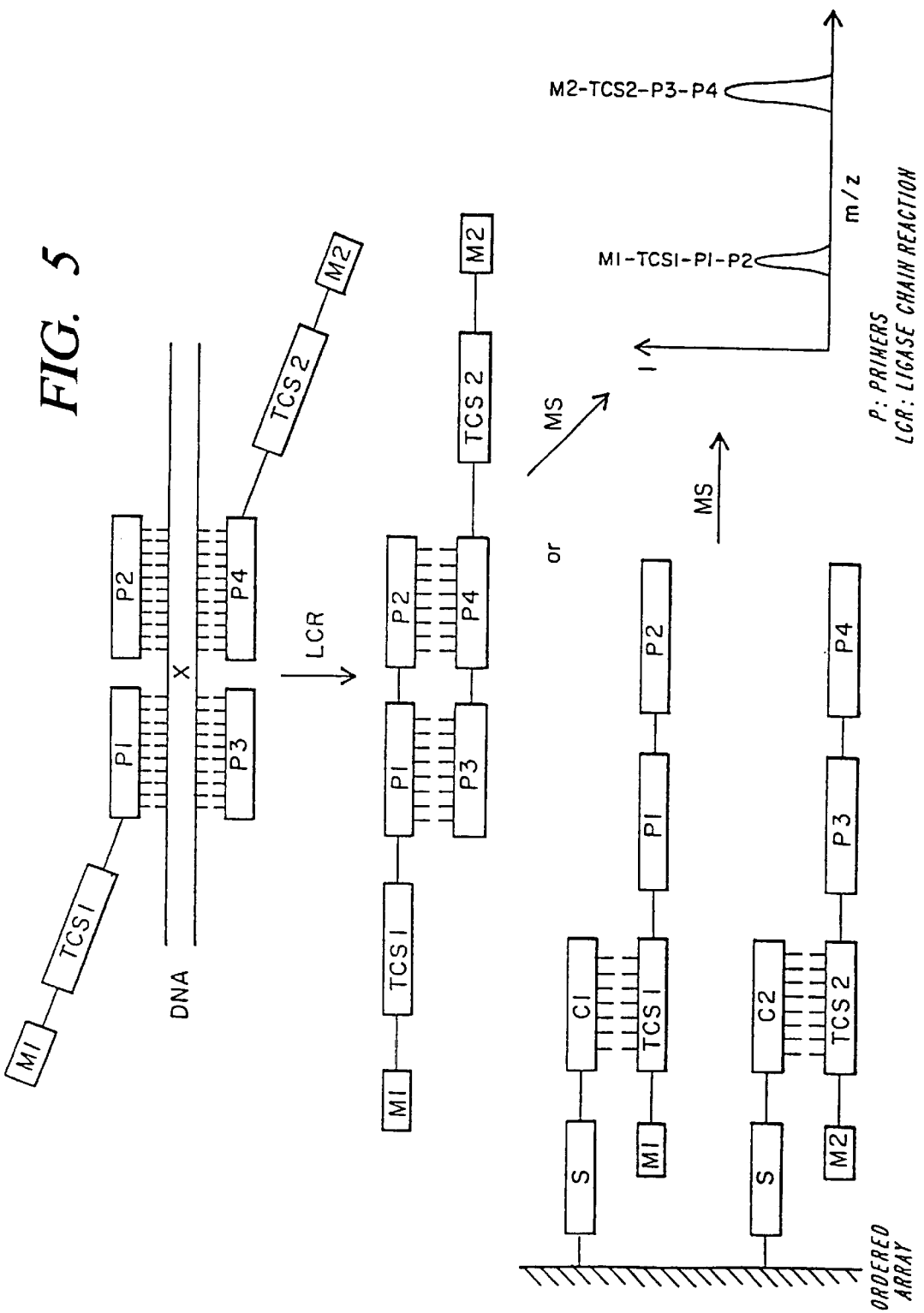
FIG. 5 is a diagram showing how amplification (here ligase chain reaction (LCR)) products can be prepared and detected by mass spectrometry. Mass differentiation can be achieved by the mass modifying functionalities (M1 and M2).attached to primers (P1 and P4 respectively). Detection by mass spectrometry can be accomplished directly (i.e.) without employing immobilization and target capturing sites (TCS)). Multiple LCR reaction can be performed in parallel by providing an ordered array of capturing sequences (C). This format allows separation of the ligation products and spot by spot identification via mass spectrometry or multiplexing if mass differentiation is sufficient.
Figure 7A:
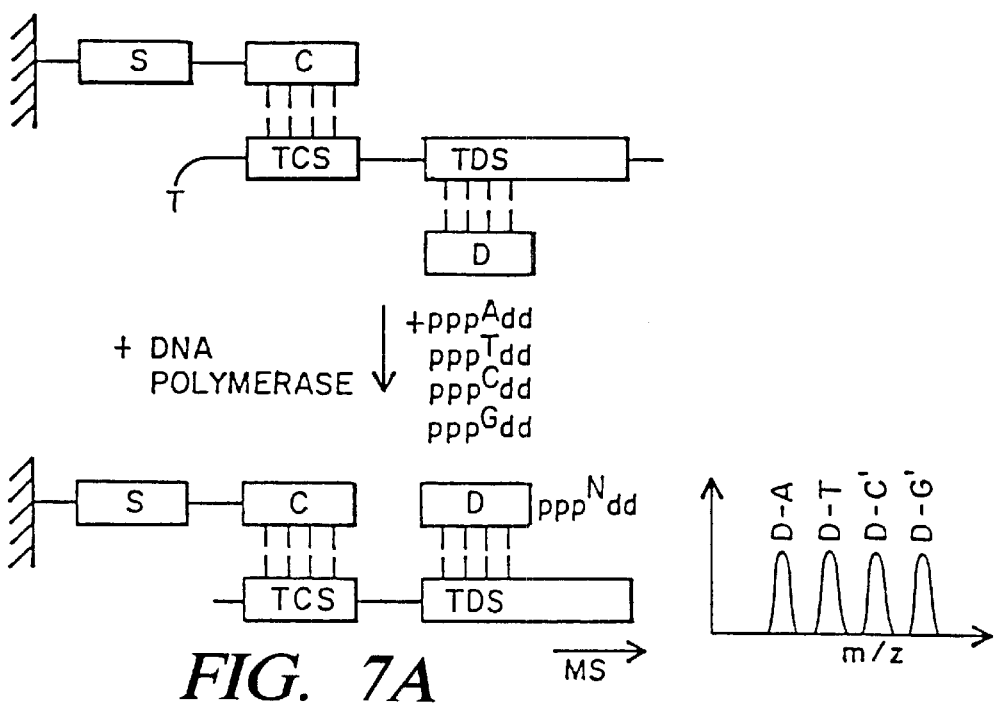
FIG. 7A is a diagram showing a process for performing mass spectrometric analysis on one target detection site (TDS) contained within a target nucleic acid molecule (T), which has been obtained from a biological sample. A specific capture sequence (C) is attached to a solid support (SS) via a spacer (S). The capture sequence is chosen to specifically hybridize with a complementary sequence on T known as the target capture site (TCS). A nucleic acid molecule that is complementary to a portion of the TDS is hybridized to the TDS 5' of the site of a mutation (X) within the TDS. The addition of a complete set of dideoxynucleosides or 3'-deoxynucleoside triphosphates (e.g. pppAdd, pppTdd, pppCdd and pppGdd) and a DNA dependent DNA polymerase allows for the addition only of the one dideoxynucleoside or 3'-deoxynucleoside triphosphate that is complementary to X.
Figure 7B:
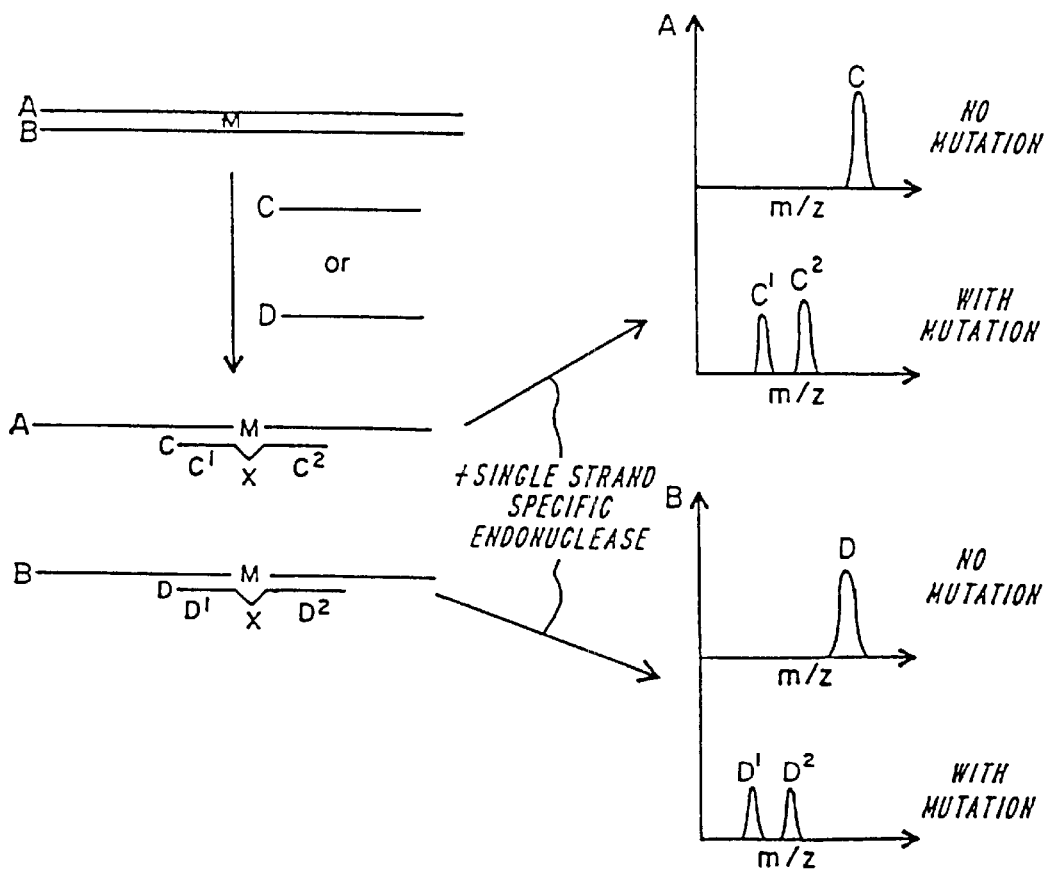
FIG. 7B is a diagram showing a process for performing mass spectrometric analysis to determine the presence of a mutation at a potential mutation site (M) within a nucleic acid molecule. This format allows for simultaneous analysis of both alleles (A) and (B) of a double stranded target nucleic acid molecule, so that a diagnosis of homozygous normal, homozygous mutant or heterozygous can be provided. Allele A and B are each hybridized with complementary oligonucleotides ((C) and (D) respectively), that hybridize to A and B within a region that includes M. Each heteroduplex is then contacted with a single strand specific endonuclease, so that a mismatch at M, indicating the presence of a mutation, results in the cleavage of (C) and/or (D), which can then be detected by mass spectrometry.

An anchoring function L' can also be incorporated into a target capturing sequence (TCS) by using appropriate primers during an amplification procedure, such as PCR (FIG. 4), LCR (FIG. 5) or transcription amplification (FIG. 6A).

Prior to mass spectrometric analysis, it may be useful to "condition" nucleic acid molecules, for example to decrease the laser energy required for volatization and/or to minimize fragmentation. Conditioning is preferably performed while a target detection site is immobilized. An example of conditioning is modification of the phosphodiester backbone of the nucleic acid molecule (e.g. cation exchange), which can be useful for eliminating peak broadening due to a heterogeneity in the cations bound per nucleotide unit. Contacting a nucleic acid molecule with an alkylating agent such as alkyliodide, iodoacetamide, β-iodoethanol, 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides which reduce sensitivity for depurination (fragmentation during MS) such as N7- or N9-deazapurine nucleotides, or RNA building blocks or using oligonucleotide triesters or incorporating phosphorothioate functions which are alkylated or employing oligonucleotide mimetics such as PNA.

Figure 2:
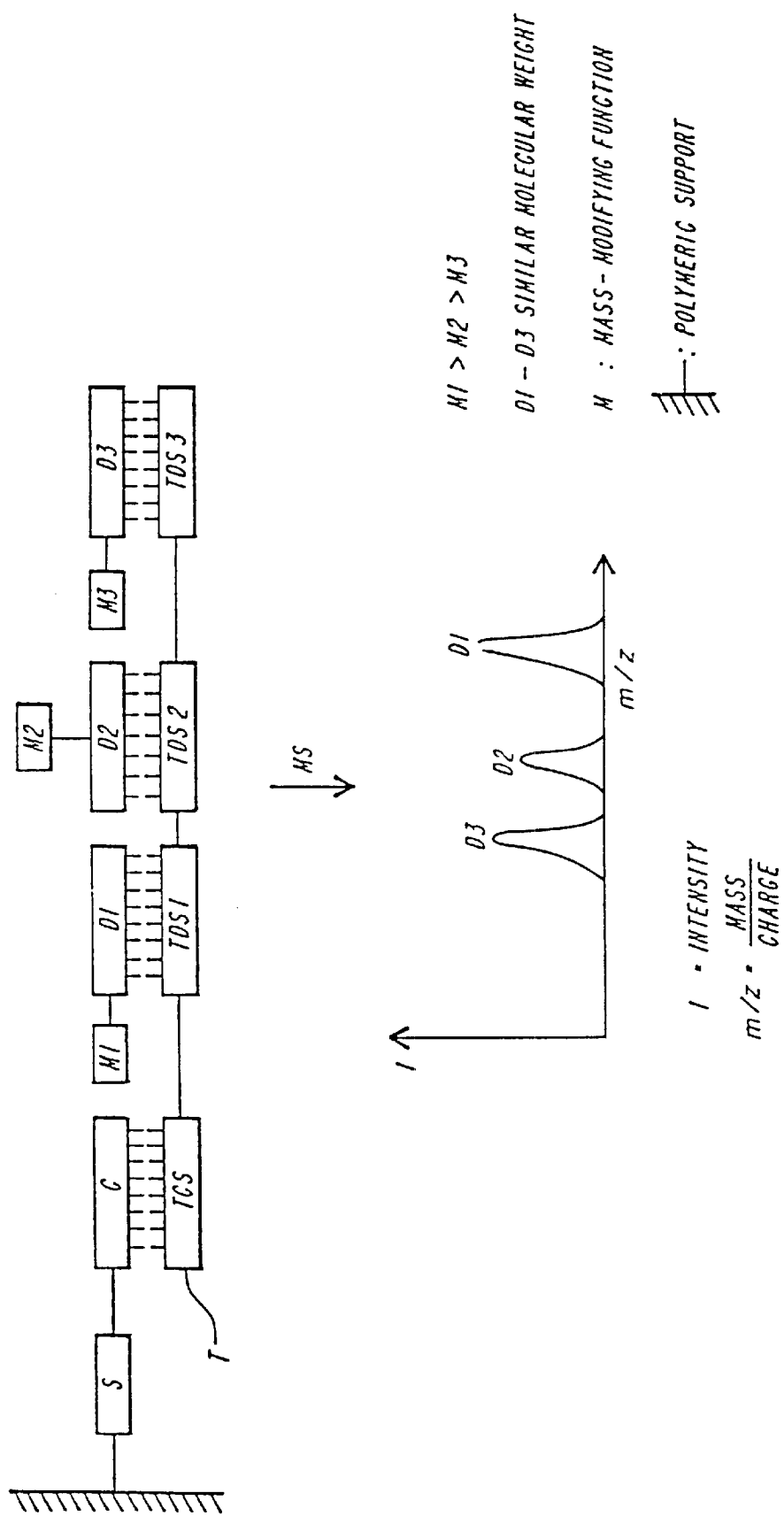
FIG. 2 is a diagram showing a process in which several mutations are simultaneously detected on one target sequence by employing corresponding detector oligonucleotides. The molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1–M3 into the detector oligonucleotide.

For certain applications, it may be useful to simultaneously detect more than one (mutated) loci on a particular captured nucleic acid fragment (on one spot of an array) or it may be useful to perform parallel processing by using oligonucleotide or oligonucleotide mimetic arrays on various solid supports. "Multiplexing" can be achieved by several different methodologies. For example, several mutations can be simultaneously detected on one target sequence by employing corresponding detector (probe) molecules (e.g. oligonucleotides or oligonucleotide mimetics). However, the molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1–M3 into the detector oligonucleotide. (FIG. 2)

Mass modifying moieties can be attached, for instance, to either the 5'-end of the oligonucleotide ($M^1$), to the nucleobase (or bases) ($M^2$, $M^7$), to the phosphate backbone ($M^3$), and to the 2'-position of the nucleoside (nucleosides) ($M^4$, $M^6$) or/and to the terminal 3'-position ($M^5$). Examples of mass modifying moieties include, for example, a halogen, an azido, or of the type, XR, wherein X is a linking group and R is a mass-modifying functionality. The mass-modifying functionality can thus be used to introduce defined mass increments into the oligonucleotide molecule.

Here the mass-modifying moiety, M, can be attached either to the nucleobase, $M^2$ (in case of the $c^7$-deazanucleosides also to C-7, $M^7$), to the triphosphate group at the alpha phosphate, $M^3$, or to the 2'-position of the sugar ring of the nucleoside triphosphate, $M^4$ and $M^6$. Furthermore, the mass-modifying functionality can be added so as to affect chain termination, such as by attaching it to the 3'-position of the sugar ring in the nucleoside triphosphate, $M^5$. For those skilled in the art, it is clear that many combinations can serve the purpose of the invention equally well. In the same way, those skilled in the art will recognize that chain-elongating nucleoside triphosphates can also be mass-modified in a similar fashion with numerous variations and combinations in functionality and attachment positions.

Without limiting the scope of the invention, the mass-modification, M, can be introduced for X in XR as well as using oligo-/-polyethylene glycol derivatives for R. The mass-modifying increment in this case is 44, i.e. five different mass-modified species can be generated by just changing m from 0 to 4 thus adding mass units of 45 (m=0), 89 (m=1), 133 (m=2), 177 (m=3) and 221 (m=4) to the nucleic acid molecule (e.g. detector oligonucleotide (D) or the nucleoside triphosphates (FIGS. 3 and 6(C), respectively). The oligo/polyethylene glycols can also be monoalkylated by a lower alkyl such as methyl, ethyl, propyl, isopropyl, t-butyl and the like. A selection of linking functionalities, X, are also illustrated. Other chemistries can be used in the mass-modified compounds, as for example, those described recently in *Oligonucleotides and Analogues, A Practical Approach* (F. Eckstein, editor, IRL Press, Oxford, 1991).

In yet another embodiment, various mass-modifying functionalities, R, other than oligo/polyethylene glycols, can be selected and attached via appropriate linking chemistries, X. A simple mass-modification can be achieved by substituting H for halogens like F, Cl, Br and/or I, or pseudohalogens such as SCN, NCS, or by using different alkyl, aryl or aralkyl moieties such as methyl, ethyl, propyl, isopropyl, t-butyl, hexyl, phenyl, substituted phenyl, benzyl, or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another mass-modification can be obtained by attaching homo- or heteropeptides through the nucleic acid molecule (e.g. detector (D)) or nucleoside triphosphates. One example useful in generating mass-modified species with a mass increment of 57 is the attachment of oligoglycines, e.g. mass-modifications of 74 (r=1, m=0), 131 (r=1, m=2), 188 (r=1, m=3), 245 (r=1, m=4) are achieved. Simple oligoamides also can be used, e.g., mass-modifications of 74 (r=1, m=0), 88 (r=2, m=0), 102 (r=3, m=0), 116 (r=4, m=0), etc. are obtainable. For those skilled in the art, it will be obvious that there are numerous possibilities in addition to those mentioned above.

As used herein, the superscript 0-i designates i+1 mass differentiated nucleotides, primers or tags. In some instances, the superscript 0 can designate an unmodified species of a particular reactant, and the superscript i can designate the i-th mass-modified species of that reactant. If, for example, more than one species of nucleic acids are to be concurrently detected, then i+1 different mass-modified detector oligonucleotides ($D^0$, $D^1$, . . . $D^i$) can be used to distinguish each species of mass modified detector oligonucleotides (D) from the others by mass spectrometry.

Different mass-modified detector oligonucleotides can be used to simultaneously detect all possible variants/mutants simultaneously (FIG. 6B). Alternatively, all four base permutations at the site of a mutation can be detected by designing and positioning a detector oligonucleotide, so that it serves as a primer for a DNA/RNA polymerase (FIG. 6C). For example, mass modifications also can be incorporated during the amplification process.

Figure 3:
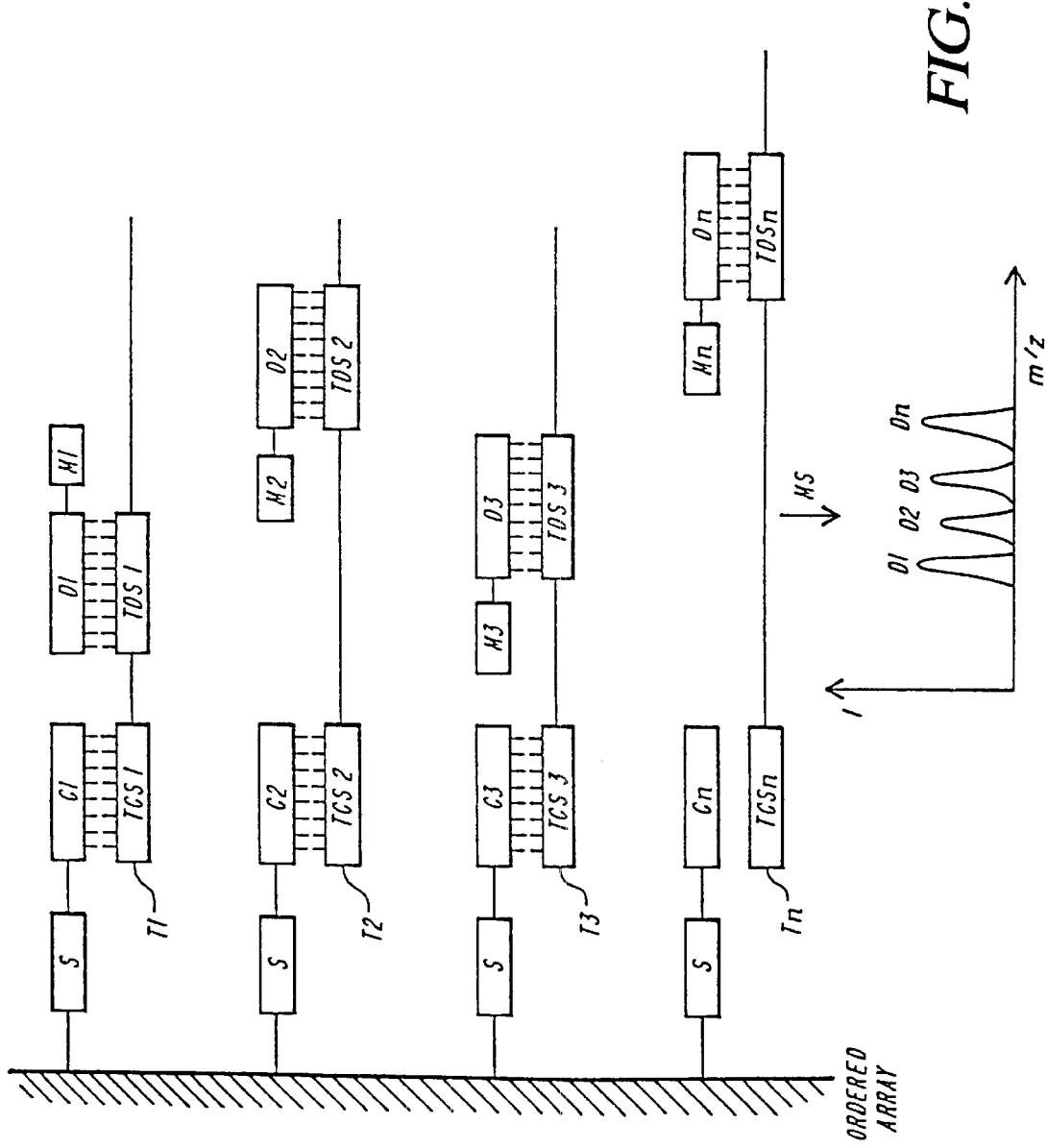
FIG. 3 is a diagram showing still another multiplex detection format. In this embodiment, differentiation is accomplished by employing different specific capture sequences which are position-specifically immobilized on a flat surface (e.g., a 'chip array'). If different target sequences T1–Tn are present, their capture sites TCS1–TCSn will interact with complementary immobilized capture sequences C1–Cn. Detection is achieved by employing appropriately mass differentiated detector oligonucleotides D1–Dn, which are mass differentiated either by their sequences or by mass modifying functionalities M1–Mn.

FIG. 3 shows a different multiplex detection format, in which differentiation is accomplished by employing different specific capture sequences which are position-specifically immobilized on a flat surface (e.g. a 'chip array'). If different target sequences T1–Tn are present, their target capture sites TCS1–TCSn will specifically interact with complementary immobilized capture sequences C1–Cn. Detection is achieved by employing appropriately mass differentiated detector oligonucleotides D1–Dn, which are mass differentiated either by their sequences or by mass modifying functionalities M1–Mn.

Preferred mass spectrometer formats for use in the invention are matrix assisted laser desorption ionization (MALDI), electrospray (ES), ion cyclotron resonance (ICR) and Fourier Transform. For ES, the samples, dissolved in water or in a volatile buffer, are injected either continuously or discontinuously into an atmospheric pressure ionization interface (API) and then mass analyzed by a quadrupole. The generation of multiple ion peaks which can be obtained using ES mass spectrometry can increase the accuracy of the mass determination. Even more detailed information on the specific structure can be obtained using an MS/MS quadrupole configuration.

n MALDI mass spectrometry, various mass analyzers can be used, e.g., magnetic sector/magnetic deflection instruments in single or triple quadrupole mode (MS/MS), Fourier transform and time-of-flight (TOF) configurations as is known in the art of mass spectrometry. For the desorption/ionization process, numerous matrix/laser combinations can be used. Ion-trap and reflectron configurations can also be employed.

The mass spectrometric processes described above can be used, for example, to diagnose any of the more than 3000 genetic diseases currently known (e.g. hemophilias, thalassemias, Duchenne Muscular Dystrophy (DMD), Huntington's Disease (HD), Alzheimer's Disease and Cystic Fibrosis (CF)) or to be identified.

The following Example 3 provides a mass spectrometer method for detecting a mutation (ΔF508) of the cystic fibrosis transmembrane conductance regulator gene (CFTR), which differs by only three base pairs (900 daltons) from the wild type of CFTR gene. As described further in Example 3, the detection is based on a single-tube, competitive oligonucleotide single base extension (COSBE) reaction using a pair of primers with the 3'-terminal base complementary to either the normal or mutant allele. Upon hybridization and addition of a polymerase and the nucleoside triphosphate one base downstream, only those primers properly annealed (i.e., no 3'-terminal mismatch) are extended; products are resolved by molecular weight shifts as determined by matrix assisted laser desorption ionization time-of-flight mass spectrometry. For the cystic fibrosis ΔF508 polymorphism, 28-mer 'normal' (N) and 30-mer 'mutant' (M) primers generate 29- and 31-mers for N and M homozygotes, respectively, and both for heterozygotes. Since primer and product molecular weights are relatively low (<10 kDa) and the mass difference between these are at least that of a single ~300 Da nucleotide unit, low resolution instrumentation is suitable for such measurements.

In addition to mutated genes, which result in genetic disease, certain birth defects are the result of chromosomal abnormalities such as Trisomy 21 (Down's syndrome), Trisomy 13 (Platau Syndrome), Trisomy 18 (Edward's Syndrome), Monosomy X (Turner's Syndrome) and other sex chromosome aneuploidies such as Klienfelter's Syndrome (XXY).

Further, there is growing evidence that certain DNA sequences may predispose an individual to any of a number of diseases such as diabetes, arteriosclerosis, obesity, various autoimmune diseases and cancer (e.g. colorectal, breast, ovarian, lung); chromosomal abnormality (either prenatally or postnatally); or a predisposition to a disease or condition (e.g. obesity, atherosclerosis, cancer). Also, the detection of "DNA fingerprints", e.g. polymorphisms, such as "microsatellite sequences", are useful for determining identity or heredity (e.g. paternity or maternity).

The following Example 4 provides a mass spectrometer method for identifying any of the three different isoforms of human apolipoprotein E, which are coded by the E2, E3 and E4 alleles. Here the molecular weights of DNA fragments obtained after restriction with appropriate restriction endonucleases can be used to detect the presence of a mutation.

Depending on the biological sample, the diagnosis for a genetic disease, chromosomal aneuploidy or genetic predisposition can be preformed either pre-or post- natally.

Viruses, bacteria, fungi and other organisms contain distinct nucleic acid sequences, which are different from the sequences contained in the host cell. Detecting or quantitating nucleic acid sequences that are specific to the infectious organism is important for diagnosing or monitoring infection. Examples of disease causing viruses that infect humans and animals and which may be detected by the disclosed processes include: Retroviridae (e.g., human immunodeficiency viruses, such as HIV-1 (also referred to as HTLV-III, LAV or HTLV-III/LAV, see Ratner, L. et al., *Nature* 313: 227–284 (1985); and Wain Hobson, S., et al, *Cell* 40: 9–17 (1985)); HIV-2 (see Guyader et al., *Nature* 328: 662–669 (1987); European Patent Publication No. 0 269 520; Chakraborti et al., *Nature* 328: 543–547 (1987); and European Patent Application No. 0 655 501); and other isolates, such as HIV-LP (International Publication No. WO 94/00562 entitled "A Novel Human Immunodeficiency Virus"; Picornaviridae (e.g., polio viruses, hepatitis A virus, (Gust, I. D., et al., Intervirology, Vol. 20, pp. 1–7 (1983); entero viruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia,* Mycobacteria sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter sp., Enterococcus sp., *Haemophilus influenzae, Bacillus antracis*, corynebacterium diphtheriae, corynebacterium sp., *Erysipelothrix rhusiopathiae, Clostridium perfringers, Clostridium tetani, Enterobacter aerogenes, Klebsiella pneumoniae, Pasturella multocida*, Bacteroides sp., *Fusobacterium nucleatum, Streptobacillus moniliformis, Treponema pallidium, Treponema pertenue*, Leptospira, and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii.*

The following Example 5 provides a nested PCR and mass spectrometer based method that was used to detect hepatitis B virus (HBV) DNA in blood samples. Similarly, other blood-borne viruses (e.g., HIV-1, HIV-2, hepatitis C virus (HCV), hepatitis A virus (HAV) and other hepatitis viruses (e.g., non-A-non-B hepatitis, hepatitis G, hepatitis E), cytomegalovirus, and herpes simplex virus (HSV)) can be detected each alone or in combination based on the methods described herein.

Since the sequence of about 16 nucleotides is specific on statistical grounds (even for a genome as large as the human genome), relatively short nucleic acid sequences can be used to detect normal and defective genes in higher organisms and to detect infectious microorganisms (e.g. bacteria, fungi, protists and yeast) and viruses. DNA sequences can even serve as a fingerprint for detection of different individuals within the same species. (Thompson, J. S. and M. W. Thompson, eds., *Genetics in Medicine*, W. B. Saunders Co., Philadelphia, Pa. (1986).

Figure 1C:
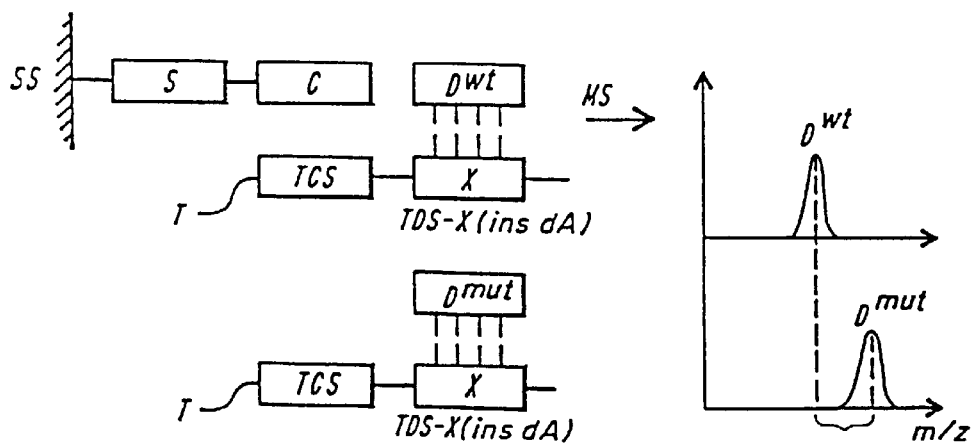
FIG. 1C is a diagram showing a process for detecting a wildtype ($D^{wt}$) and/or a mutant ($D^{mut}$) sequence in a target (T) nucleic acid molecule. As in FIG. 1A, a specific capture sequence (C) is attached to a solid support (SS) via a spacer (S). In addition the capture sequence is chosen to specifically interact with a complementary sequence on the target sequence (T), the target capture site (TCS) to be detected through hybridization. However, the target detection site (TDS) includes mutation, X, which changes the molecular weight; mutated target detection sites can be distinguished from wildtype by mass spectrometry. Preferably, the detector nucleic acid molecule (D) is designed so that the mutation is in the middle of the molecule and therefore would not lead to a stable hybrid if the wildtype detector oligonucleotide ($D^{wt}$) is contacted with the target detector sequence, e.g. as a control. The mutation can also be detected if the mutated detector oligonucleotide ($D^{mut}$) with the matching base as the mutated position is used for hybridization. If a nucleic acid molecule obtained from a biological sample is heterozygous for the particular sequence (i.e. contain both $D^{wt}$ and $D^{mut}$) both $D^{wt}$ and $D^{mut}$ will be bound to the appropriate strand and the mass difference allows both $D^{wt}$ and $D^{mut}$ to be detected simultaneously.

One process for detecting a wildtype ($D^{wt}$) and/or a mutant ($D^{mut}$) sequence in a target (T) nucleic acid molecule is shown in FIG. 1C. A specific capture sequence (C) is attached to a solid support (ss) via a spacer (S). In addition, the capture sequence is chosen to specifically interact with a complementary sequence on the target sequence (T), the target capture site (TCS) to be detected through hybridization. However, if the target detection site (TDS) includes a mutation, X, which increases or decreases the molecular weight, mutated TDS can be distinguished from wildtype by mass spectrometry. For example, in the case of an adenine base (dA) insertion, the difference in molecular weights between $D^{wt}$ and $D^{mut}$ would be about 314 daltons.

Preferably, the detector nucleic acid (D) is designed such that the mutation would be in the middle of the molecule and the flanking regions are short enough so that a stable hybrid would not be formed if the wildtype detector oligonucleotide ($D^{wt}$) is contacted with the mutated target detector sequence as a control. The mutation can also be detected if the mutated detector oligonucleotide ($D^{mut}$) with the matching base at the mutated position is used for hybridization. If a nucleic acid obtained from a biological sample is heterozygous for the particular sequence (i.e. contain both $D^{wt}$ and $D^{mut}$), both $D^{wt}$ and $D^{mut}$ will be bound to the appropriate strand and the mass difference allows by $D^{wt}$ and $D^{mut}$ to be detected simultaneously.

Figure 8:
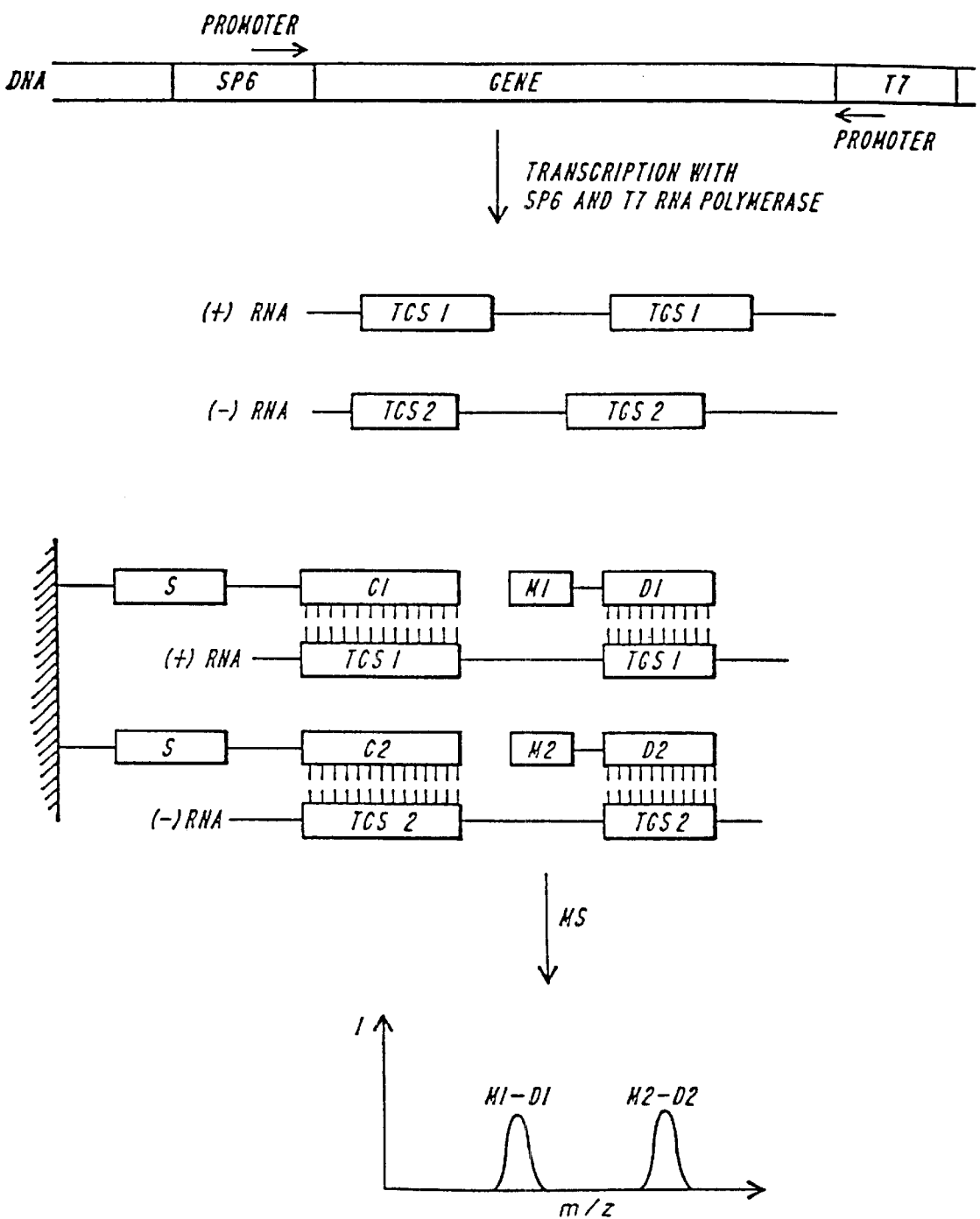
FIG. 8 is a diagram showing how both strands of a target DNA can be prepared for detection using transcription vectors having two different promoters at opposite locations (e.g. the SP 6 and T7 promoter). This format is particularly useful for detecting heterozygous target detection sites (TDS). Employing the SP 6 or the T7 RNA polymerase both strands could be transcribed separately or simultaneously. Both RNAs can be specifically captured and simultaneously detected using appropriately mass-differentiated detector oligonucleotides. This can be accomplished either directly in solution or by parallel processing of many target sequences on an ordered array of specifically immobilized capturing sequences.
Figure 9:
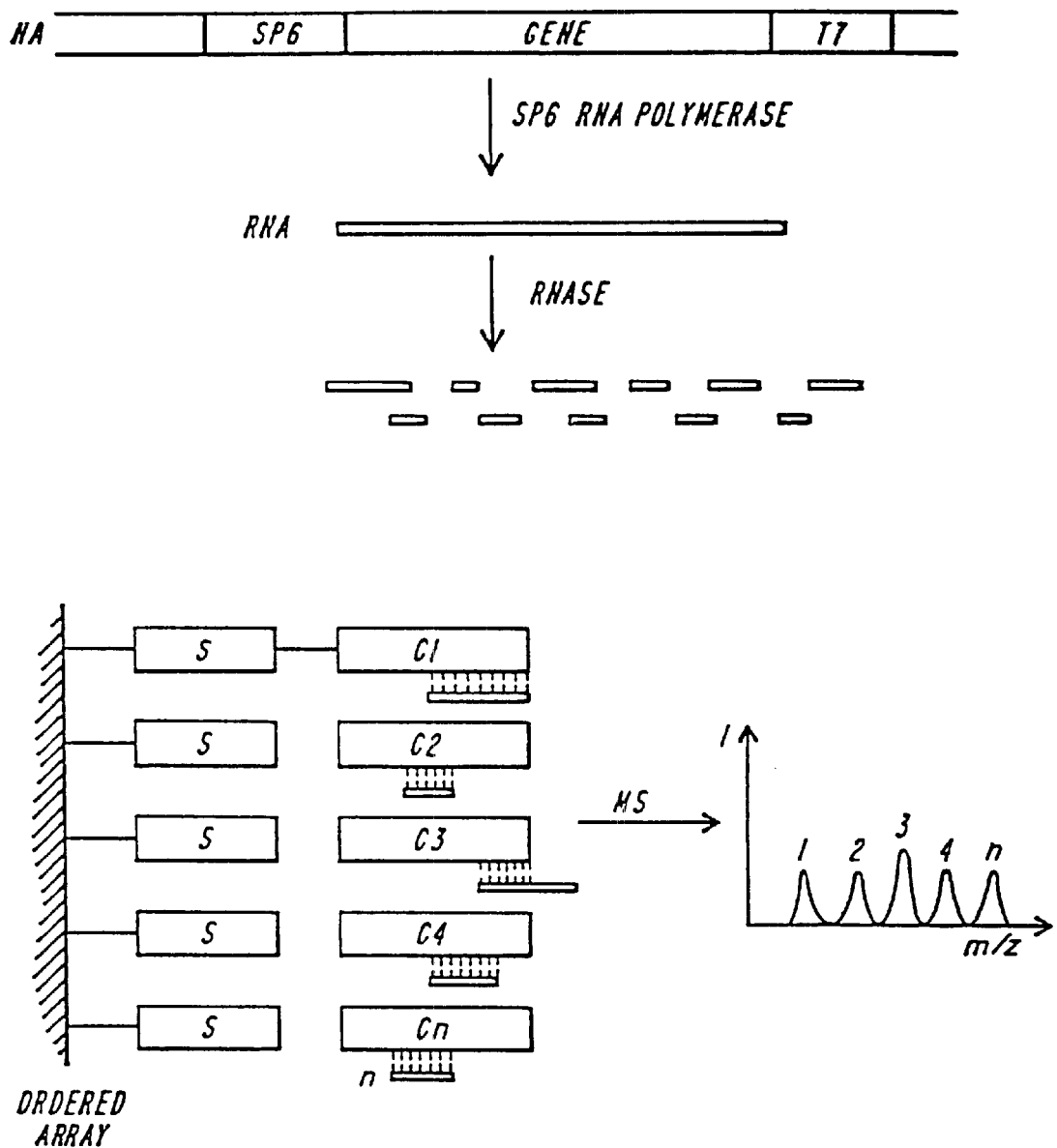
FIG. 9 is a diagram showing how RNA prepared as described in FIGS. 6, 7 and 8 can be specifically digested using one or more ribonucleases and the fragments captured on a solid support carrying the corresponding complementary sequences. Hybridization events and the actual molecular weights of the captured target sequences provide information on whether and where mutations in the gene are present. The array can be analyzed spot by spot using mass spectrometry. DNA can be similarly digested using a cocktail of nucleases including restriction endonucleases. Mutations can be detected by different molecular weights of specific, individual fragments compared to the molecular weights of the wildtype fragments.
Figures 1, 10A:
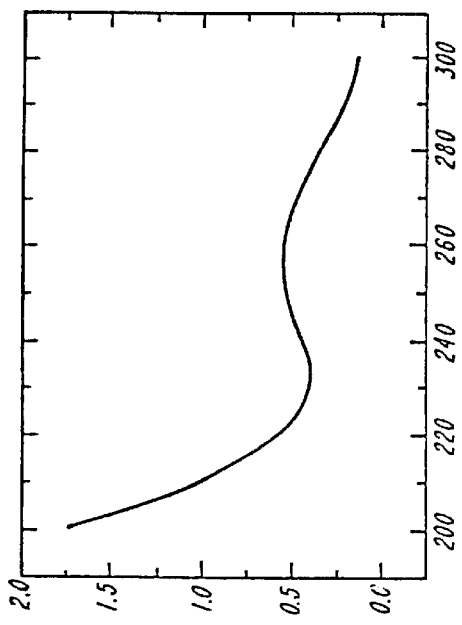
Figures 2, 10A:
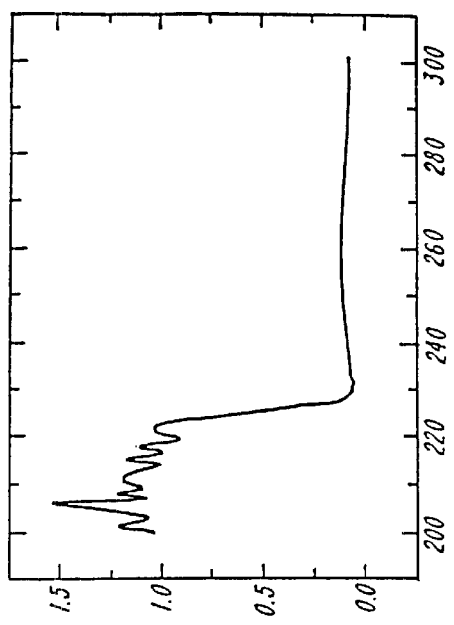
FIG. 10A shows a spectra resulting from the experiment described in the following Example 1.
Figures 3, 10A:
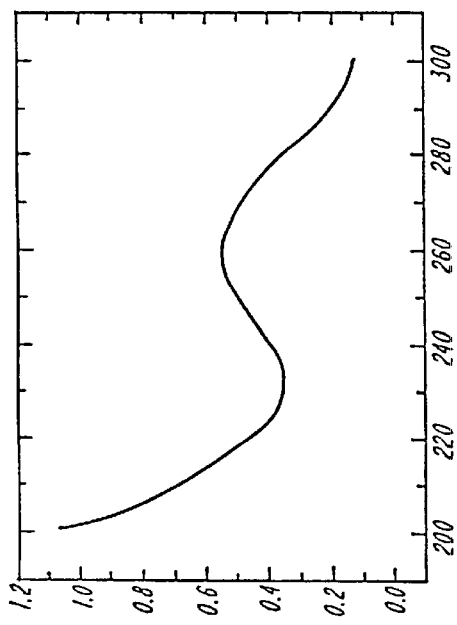
Figures 4, 10A:
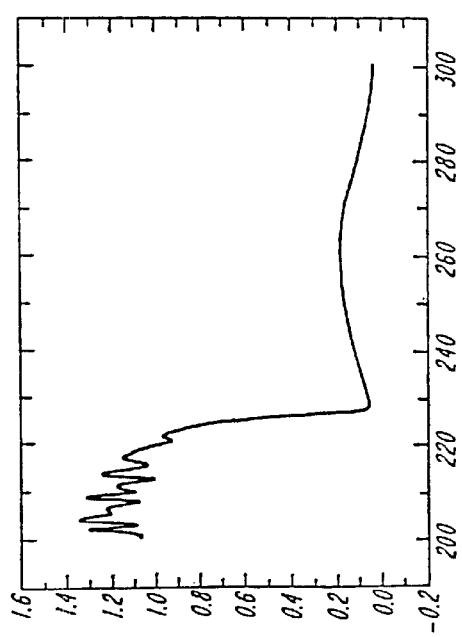
Figure 10B:
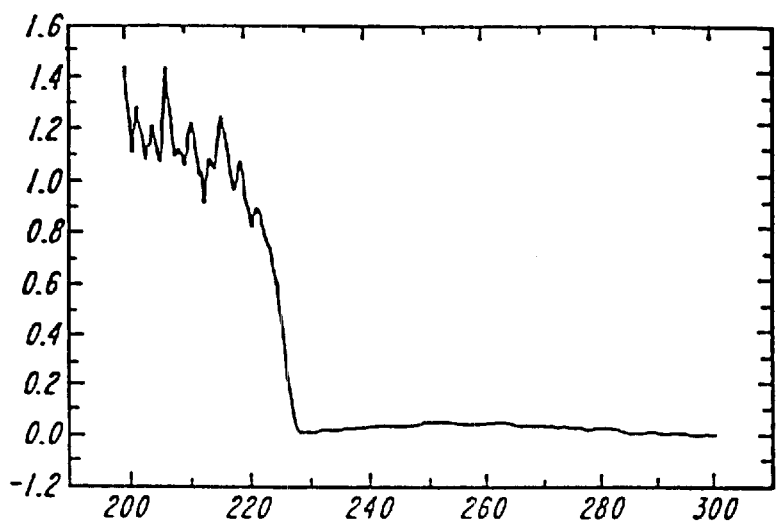
FIG. 10B shows a spectra resulting from the experiment described in the following Example 1 after three washing/centrifugation steps.

The process of this invention makes use of the known sequence information of the target sequence and known mutation sites, although new mutations can also be detected. For example, as shown in FIG. 8, transcription of a nucleic acid molecule obtained from a biological sample can be specifically digested using one or more nucleases and the fragments captured on a solid support carrying the corresponding complementary nucleic acid sequences. Detection of hybridization and the molecular weights of the captured target sequences provide information on whether and where in a gene a mutation is present. Alternatively, DNA can be cleaved by one or more specific endonucleases to form a mixture of fragments. Comparison of the molecular weights between wildtype and mutant fragment mixtures results in mutation detection.

The present invention is further illustrated by the following examples which should not be construed as limiting in any way. The contents of all cited references (including literature references, issued patents, published patent applications (including international patent application Publication Number WO 94/16101 and U.S. Pat. No. 5,605,798, entitled DNA Sequencing by Mass Spectrometry by H. Köster; and international patent application Publication Number WO 94/21822 and U.S. Pat. No. 5,622,824, entitled "DNA Sequencing by Mass Spectrometry Via Exonuclease Degradation" by H. Köster), and co-pending patent applications, (including U.S. patent application Ser. No. 08/406,199, now U.S. Pat. No. 5,605,798 entitled DNA Diagnostics Based on Mass Spectrometry by H. Köster), as cited throughout this application are hereby expressly incorporated by reference.

EXAMPLE 1

MALDI-TOF Desorption of Oligonucleotides Directly on Solid Supports 1 g CPC (Controlled Pore Glass) was functionalized with 3-(triethoxysilyl)- epoxypropan to form OH-groups on the polymer surface. A standard oligonucleotide synthesis with 13 mg of the OH-CPG on a DNA synthesizer (Milligen, Model 7500) employing β-cyanoethyl-phosphoamidites (Sinha et al., Nucleic Acids Res. 12: 4539 (1984)) and TAC N-protecting groups (Köster et al., Tetrahedron 37: 362 (1981)) was performed to synthesize a 3'-$T_5$-50-mer oligonucleotide sequence in which nucleotides are complementary to a "hypothetical" 50-mer sequence. $T_5$ serves as a spacer. Deprotection with saturated ammonia in methanol at room temperature for 2 hours furnished according to the determination of the DMT group CPG which contained about 10 μmol 55-mer/g CPG. This 55-mer served as a template for hybridizations with a 26-mer (with 5'-DMT group) and a 40-mer (without DMT group). The reaction volume is 100 μl and contains about 1 nmol CPG bound 55-mer as template, an equimolar amount of oligonucleotide in solution (26-mer or 40-mer) in 20 mM Tris-HCl, pH 7.5, 10 mM $MgCl_2$ and 25 mM NaCl. The mixture was heated for 10' at 65° C. and cooled at 37° C. during 30' (annealing). The oligonucleotide which has not been hybridized to the polymer-bound template were removed by centrifugation and three subsequent washing/centrifugation steps with 100 μl each of ice-cold 50 mM ammonium citrate. The beads were air-dried and mixed with matrix solution (3-hydroxypicolinic acid/10 mM ammonium citrate in acetonitrile/water, 1:1), and analyzed by MALDI-TOF mass spectrometry. The results are presented in FIGS. 10A–C and 11.

EXAMPLE 2

Electrospray (ES) Desorption and Differentiation of an 18-mer and 19-mer

DNA fragments at a concentration of 50 pmole/μl in 2-propanol/10 mM ammonium carbonate (1/9, v/v) were analyzed simultaneously by an electrospray mass spectrometer.

Figure 12A:
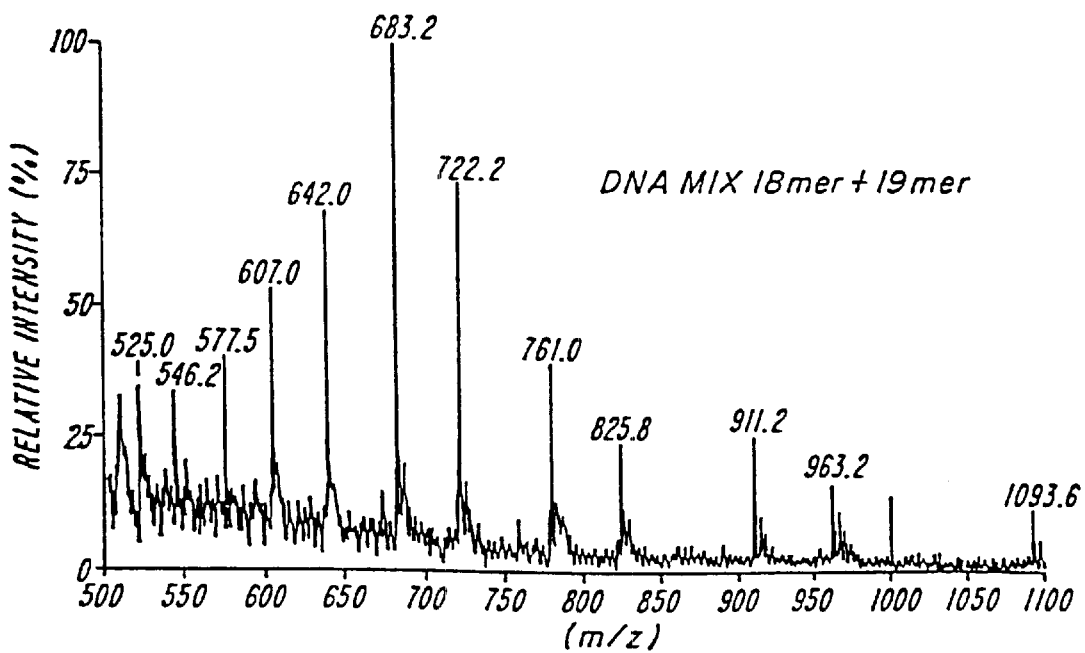
FIGS. 12A–C show spectra resulting from the experiment described in the following Example 2 showing the successful desorption and differentiation of an 18-mer and 19-mer by electrospray mass spectrometry: the mixture (12A), peaks resulting from the 18-mer, emphasized (12B) and peaks resulting from the 19-mer, emphasized (12C).
Figure 10C:
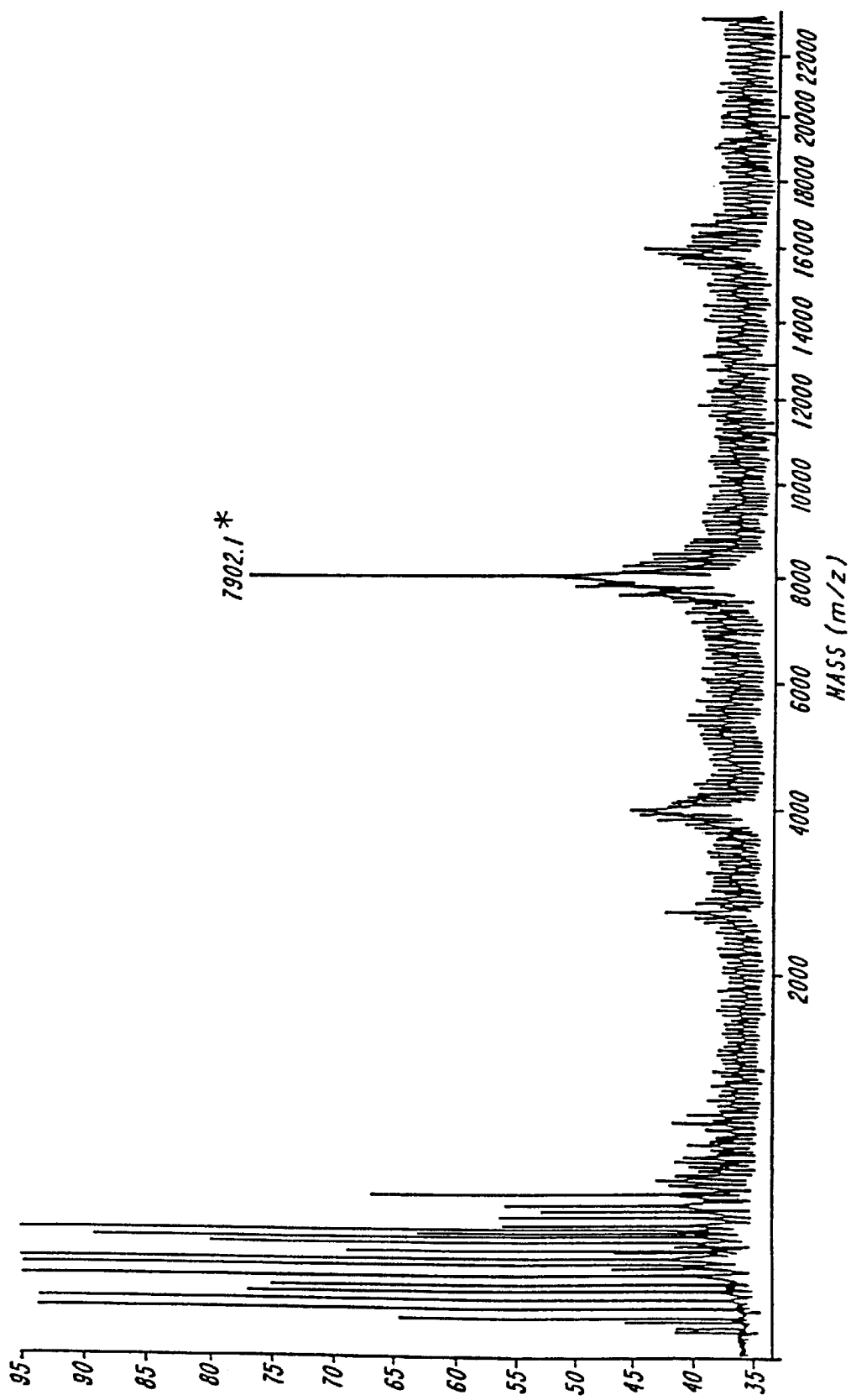
FIG. 10C shows a spectra resulting from the experiment described in the following Example 1 showing the successful desorption of the hybridized 26-mer off of beads.
Figure 11:
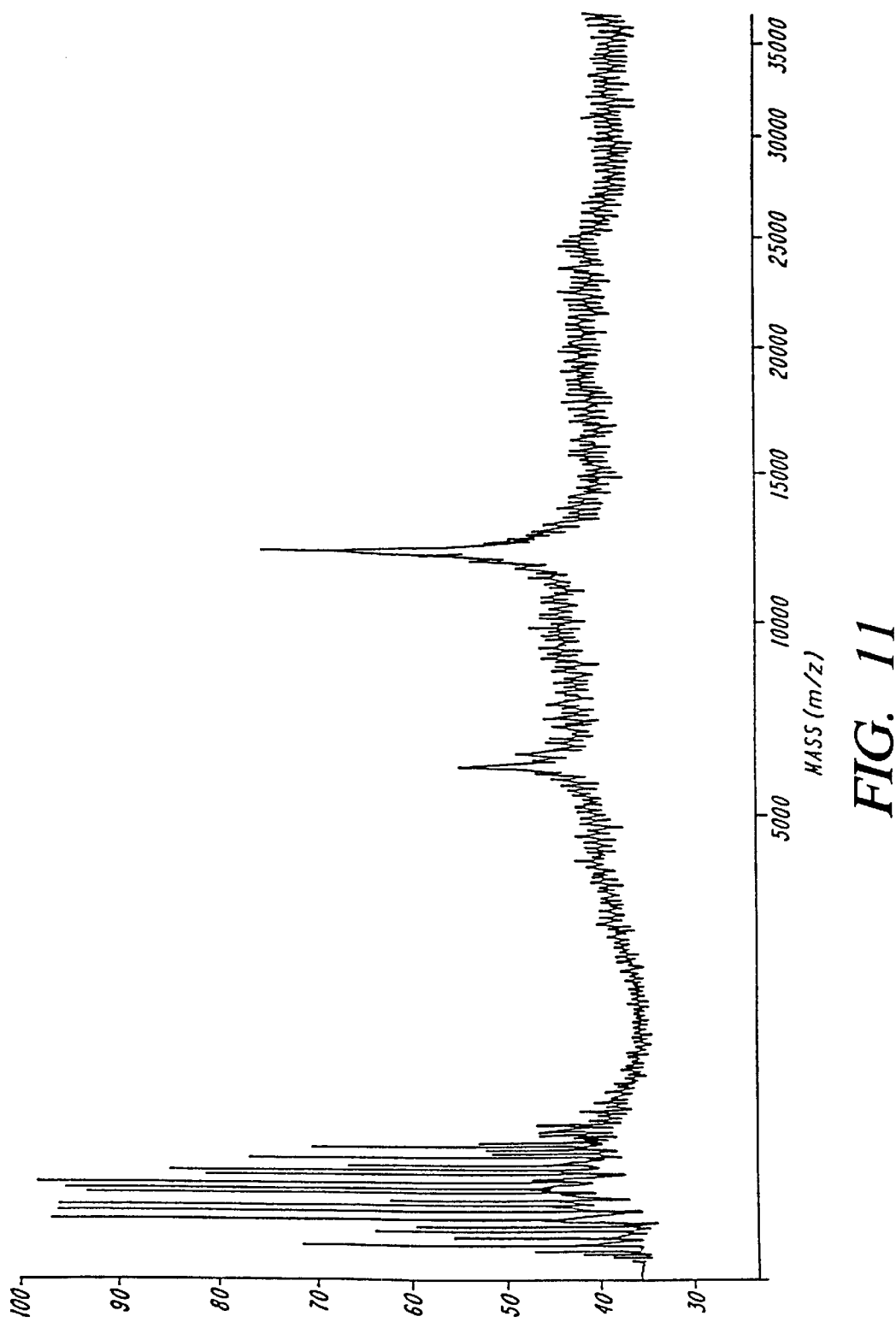
FIG. 11 shows a spectra resulting from the experiment described in the following Example 1 showing the successful desorption of the hybridized 40-mer. The efficiency of detection suggests that fragments much longer 40-mers can also be desorbed.
Figure 12B:
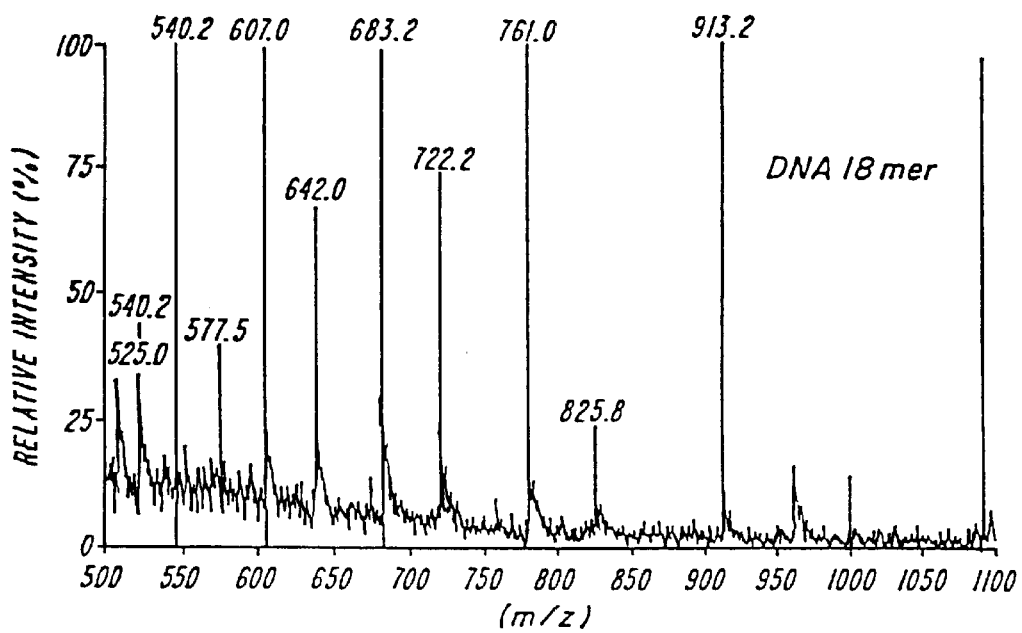
Figure 12C:
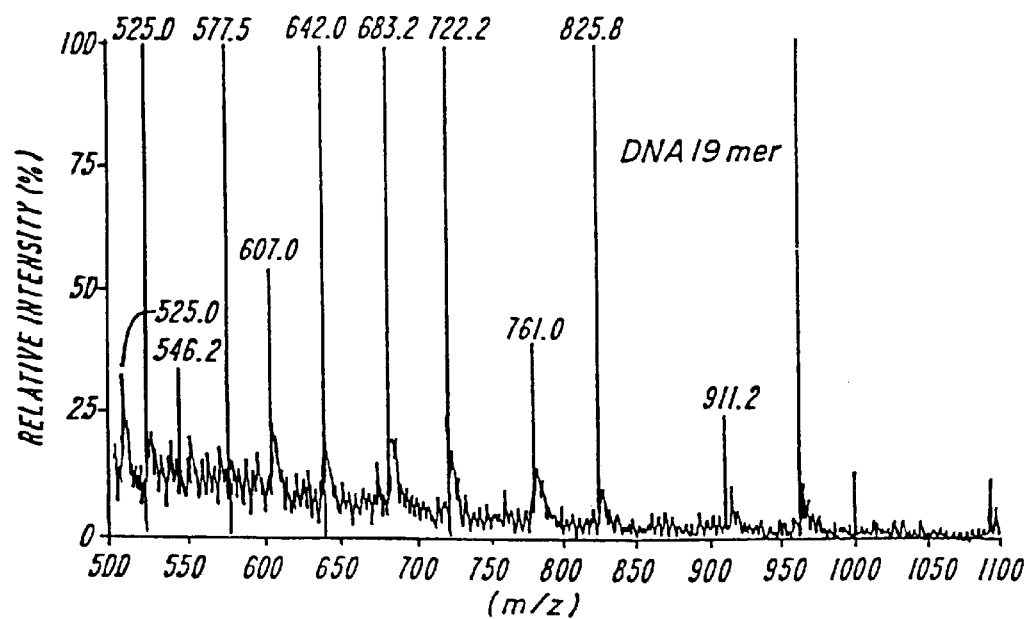

The successful desorption and differentiation of an 18-mer and 19-mer by electrospray mass spectrometry is shown in FIGS. 12A–C.

EXAMPLE 3

Detection of The Cystic Fibrosis Mutation, ΔF508, by Single Step Dideoxy Extension and Analysis by MALDI-TOF Mass Spectrometry

Material and Methods

PCR Amplification and Strand Immobilization. Amplification was carried out with exon 10 specific primers using standard PCR conditions (30 cycles: 1'@95° C., 1'@55° C., 2'@72° C.); the reverse primer was 5' labelled with biotin and column purified (Oligopurification Cartridge, Cruachem). After amplification the PCR products were purified by column separation (Qiagen Quickspin) and immobilized on streptavidin coated magnetic beads (DynaBeads, Dynal, Norway) according to their standard protocol; DNA was denatured using 0.1M NaOH and washed with 0.1M NaOH, 1× B+W buffer and TE buffer to remove the non-biotinylated sense strand.

COSBE Conditions.

The beads containing ligated antisense strand were resuspended in 18 μl of Reaction mix (2 μl 10× Taq buffer, 1 μL (1 unit) Taq Polymerase, 2 μL of 2 mM dGTP, and 13 μL $H_2O$) and incubated at 80° C. for 5' before the addition of Reaction mix 2 (100 ng each of COSBE primers). The temperature was reduced to 60° C. and the mixtures incubated for 5' annealing/extension period; the beads were then washed in 25 mM triethylammonium acetate (TEAA) followed by 50 mM ammonium citrate.

Primer Sequences.

All primers were synthesized on a Perseptive Biosystems Expedite 8900 DNA Synthesizer using conventional phosphoramidite chemistry (Sinha et al. (1984) Nucleic Acids Res. 12: 4539. COSBE primers (both containing an intentional mismatch one base before the 3'-terminus) were those used in a previous ARMS study (Ferrie et al., (1992) Am J Hum Genet 51: 251–262) with the exception that two bases were removed from the 5'-end of the normal:

Ex 10 PCR (Forward): 5'-BIO-GCA AGT GAA TCC TGA GCG TG-3' (SEQ.ID.No. 1)

Ex 10 PCR (Reverse): 5'-GTG TGA AGG GTT CAT ATG C-3' (SEQ.ID.No. 2)

COSBE ΔF508-N 5'-ATC TAT ATT CAT CAT AGG AAA CAC CAC A-3' (28-mer) (SEQ.ID.No. 3)

COSBE ΔF508-M 5'-GTA TCT ATA TTC ATC ATA GGA AAC ACC ATT-3' (30-mer) (SEQ.ID.No. 4).

Mass Spectrometry.

After washing, beads were resuspended in 1 μl 18 Mohm/cm $H_2O$. 300 nL each of matrix (Wu et al. (1993) Rapid Commun Mass Spectrom 7: 142–146) solution (0.7 M 3-hydroxypicolinic acid, 0.7 M dibasic ammonium citrate in 1:1 $H_2O:CH_3CN$) and resuspended beads (Tang et al. (1995) Rapid Commun Mass Spectrom 8: 727–730) were mixed on a sample target and allowed to air dry. Up to 20 samples were spotted on a probe target disk for introduction into the source region of an unmodified Thermo Bioanalysis (formerly Finnigan) Visions 2000 MALDI-TOF operated in reflectron mode with 5 and 20 kV on the target and conversion dynode, respectively. Theoretical average molecular weights ($M_r$(calc)) were calculated from atomic compositions. Vendor-provided software was used to determine peak centroids using external calibration; 1.08 Da has been subtracted from these to correct for the charge-carrying proton mass to yield the test Mr(exp) values.

Scheme.

Upon annealing to the bound template, the N and M primers (8508.6 and 9148.0 Da, respectively) are presented with dGTP; only primers with proper Watson-Crick base paring at the variable (V) position are extended by the polymerase. Thus if V pairs with 3'-terminal base of N, N is extended to a 8837.9 Da product (N+1). Likewise, if V is properly matched to the M terminus, M is extended to a 9477.3 Da M+1 product.

Results

FIGS. 14–18 show the representative mass spectra of COSBE reaction products. Better results were obtained when PCR products were purified before the biotinylated anti-sense strand was bound

EXAMPLE 4

Differentiation of Human Apolipoprotein E Isoforms by Mass Spectrometry

Apolipoprotein E (Apo E), a protein component of lipoproteins, plays an essential role in lipid metabolism. For example, it is involved with cholesterol transport, metabolism of lipoprotein particles, immunoregulation and activation of a number of lipolytic enzymes.

There are common isoforms of human Apo E (coded by E2, E3, and E4 alleles). The most common is the E3 allele. The E2 allele has been shown to decrease the cholesterol level in plasma and therefore may have a protective effect against the development of atherosclerosis. Finally, the E4 isoform has been correlated with increased levels of cholesterol, conferring predisposition to atherosclerosis. Therefore, the identity of the apo E allele of a particular individual is an important determinant of risk for the development of cardiovascular disease.

Figure 19:
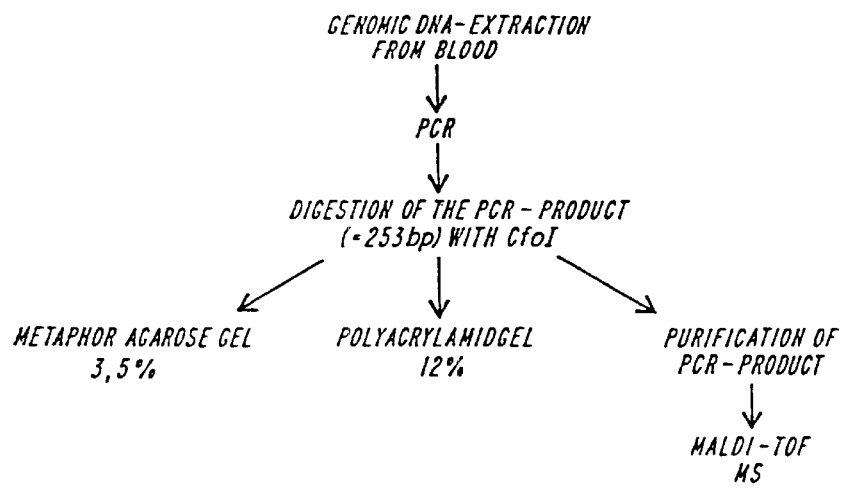
FIG. 19 is a graphic representation of various processes for performing apolipoprotein E genotyping.
Figure 13:
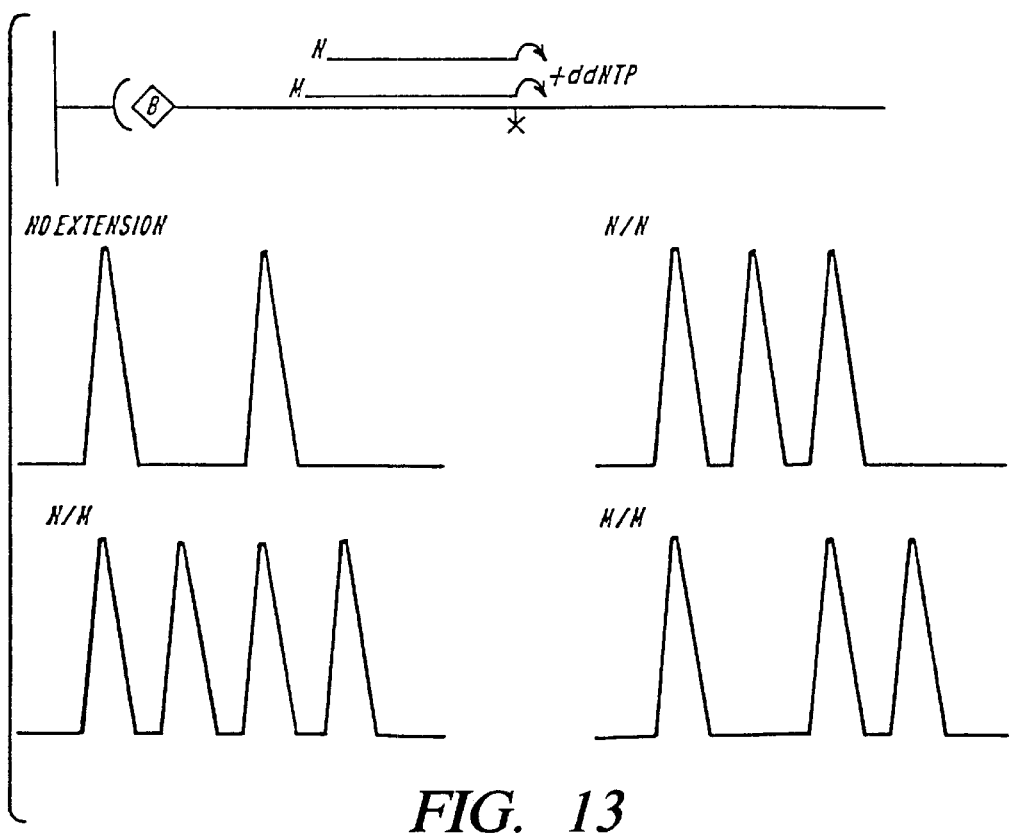
FIG. 13 is a graphic representation of the process for detecting the Cystic Fibrosis mutation ΔF508 as described in Example 3; N indicates normal and M indicats the mutation detection primer or extended primer.
Figure 14:
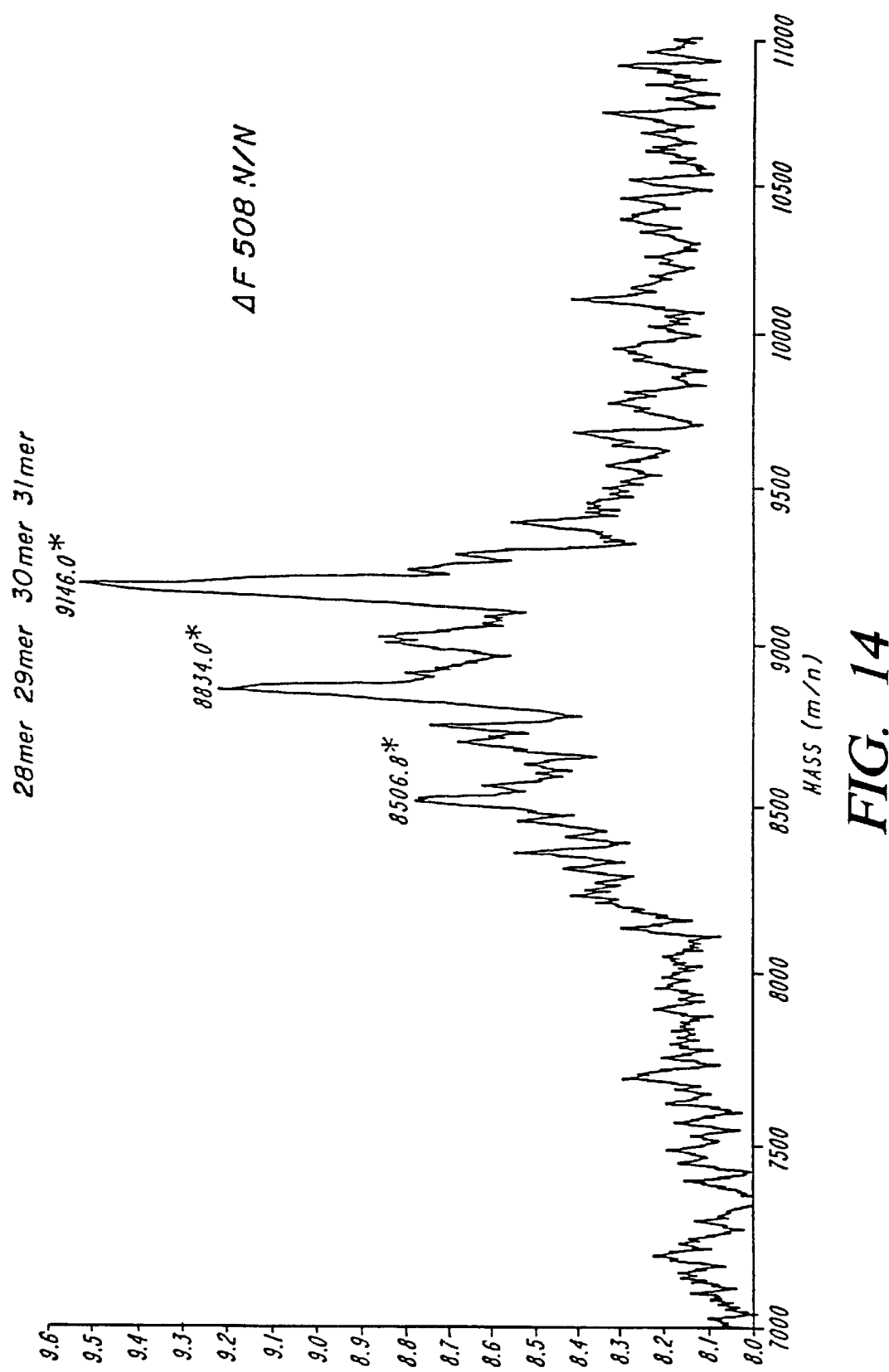
FIG. 14 is a mass spectrum of the DNA extension product of a ΔF508 homozygous normal.
Figure 15:
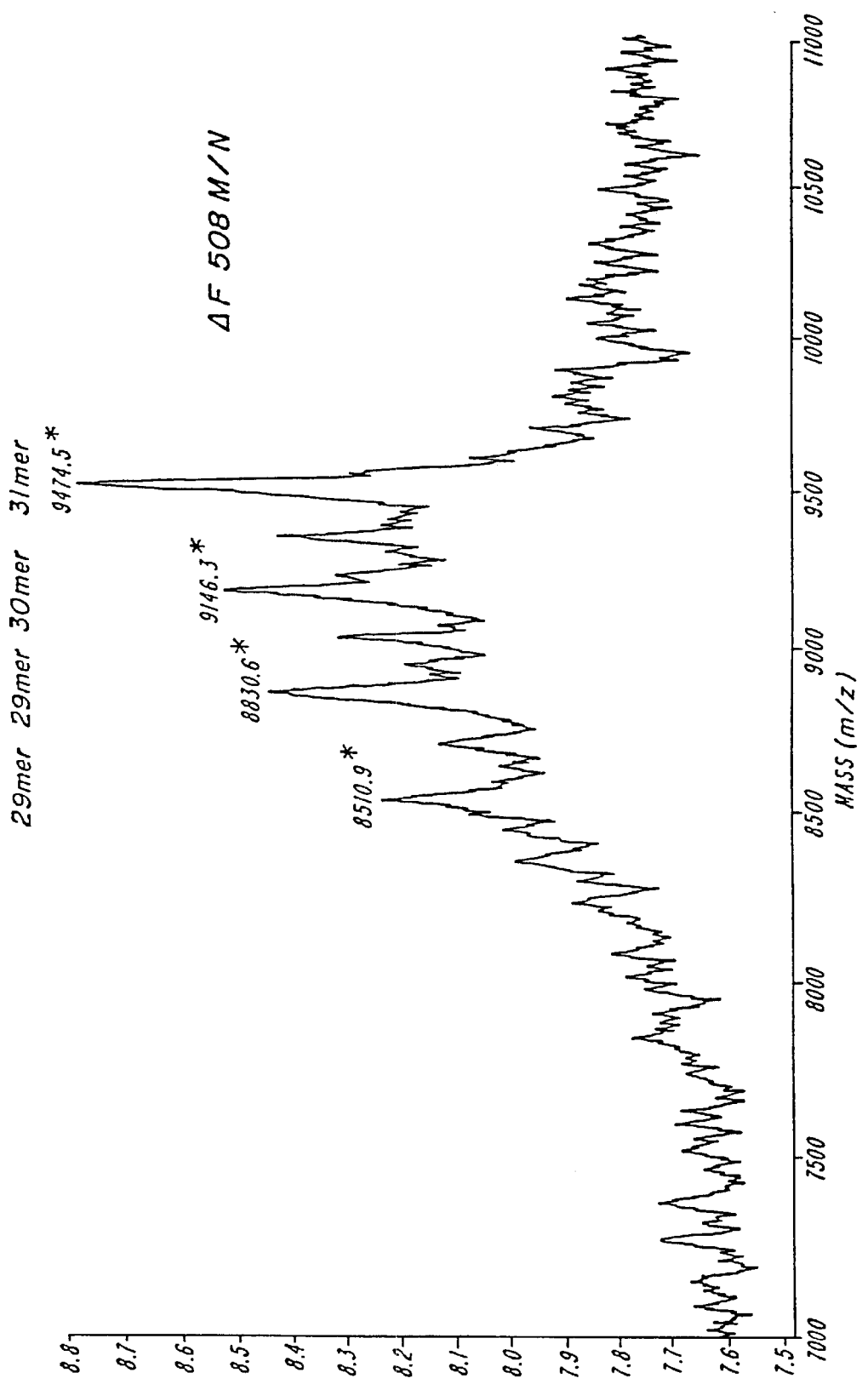
FIG. 15 is a mass spectrum of the DNA extension product of a ΔF508 heterozygous mutant.
Figure 16:
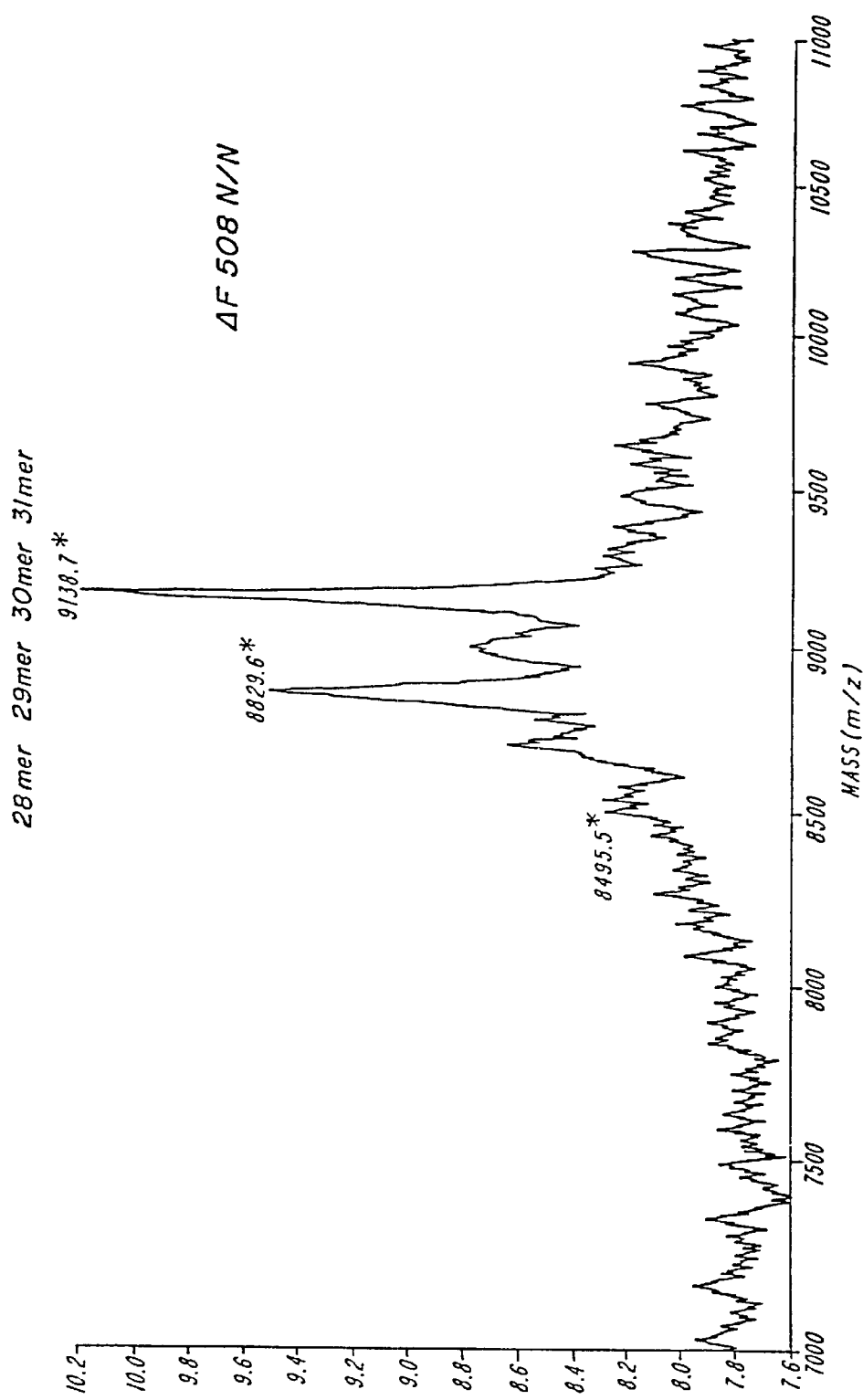
FIG. 16 is a mass spectrum of the DNA extension product of a ΔF508 homozygous normal.
Figure 17:
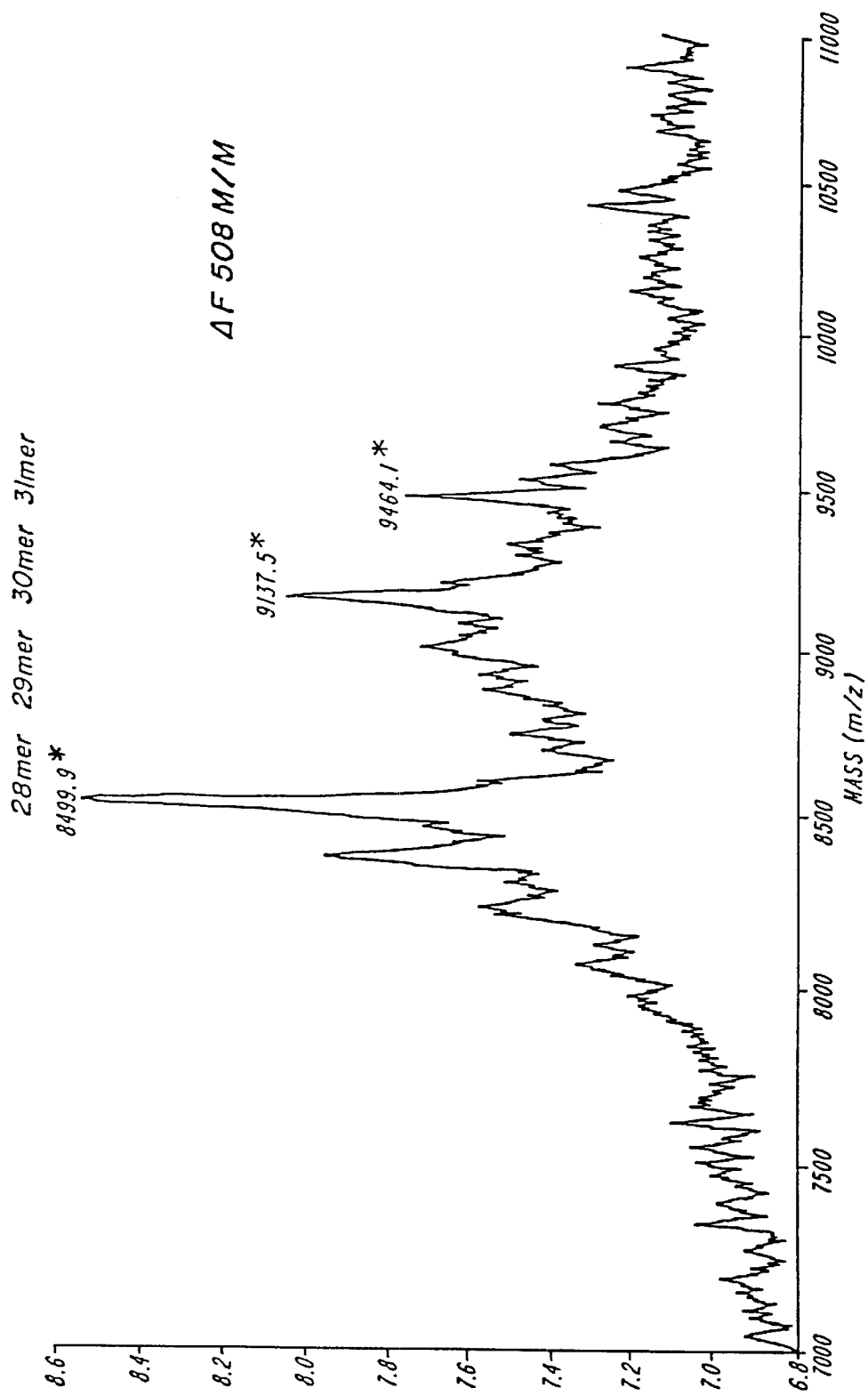
FIG. 17 is a mass spectrum of the DNA extension product of a ΔF508 homozygous mutant.
Figure 18:
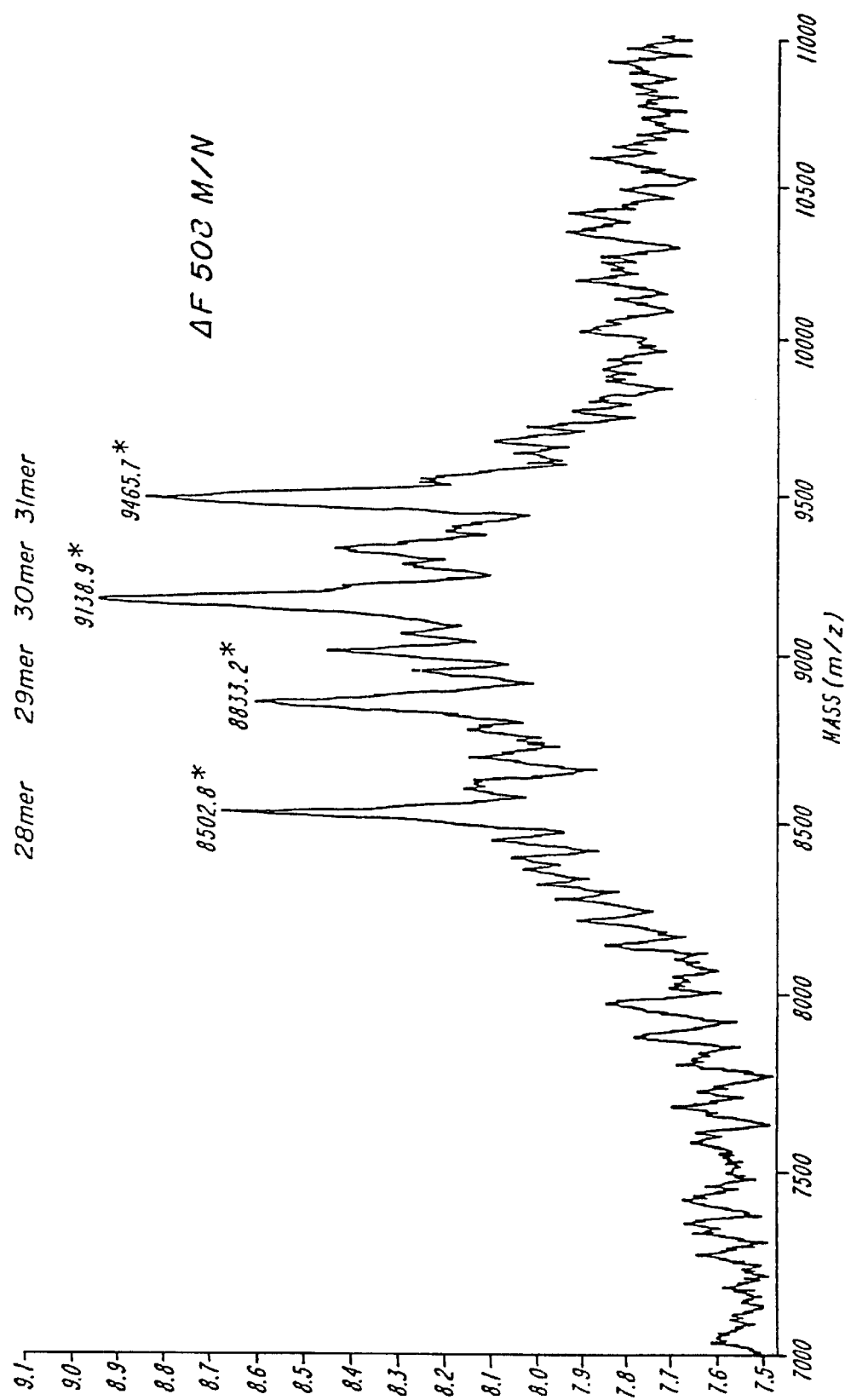
FIG. 18 is mass spectrum of the DNA extension product of a ΔF508 heterozygous mutant.
Figure 20A:
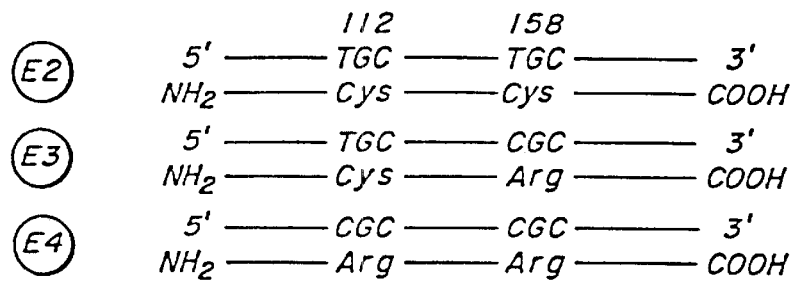
FIGS. 20A–B show the nucleic acid sequence of normal apolipoprotein E (encoded by the E3 allele) and other isotypes encoded by the E2 and E4 alleles.
Figure 20B:
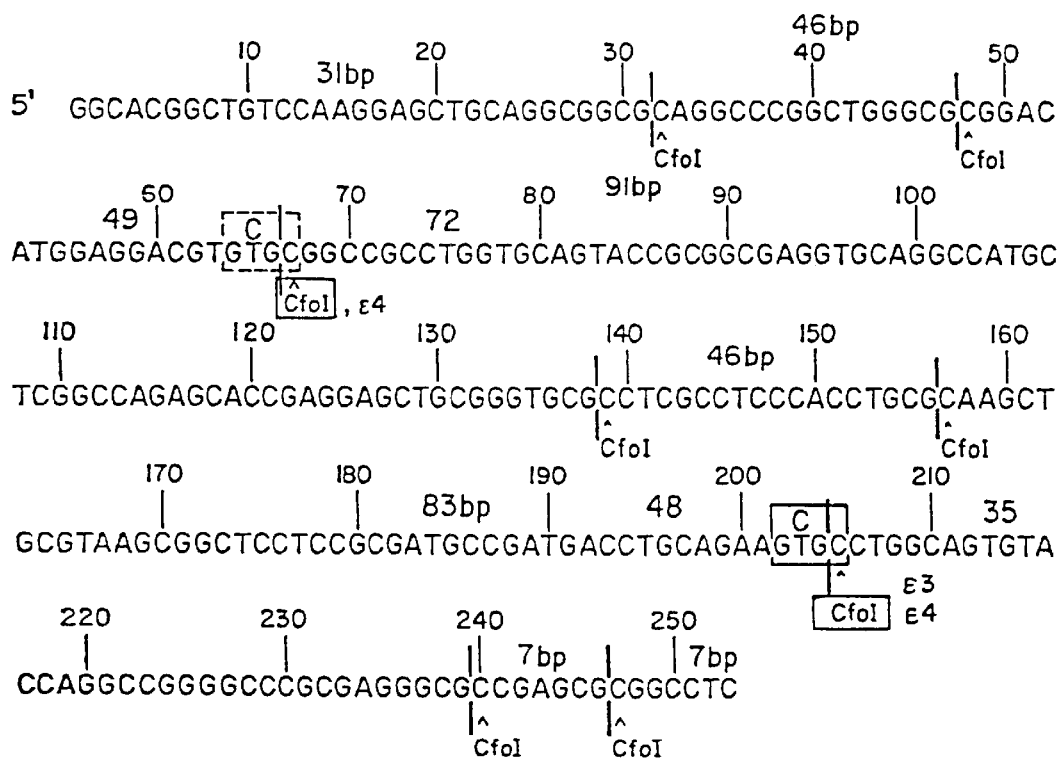

As shown in FIG. 19, a sample of DNA encoding apolipoprotein E can be obtained from a subject, amplified (e.g. via PCR); and the PCR product can be digested using an appropriate enzyme (e.g. Cfol). The restriction digest obtained can then be analyzed by a variety of means. As shown in FIGS. 20A–B, the three isotypes of apolipoprotein E (E2, E3 and E4 have different nucleic acid sequences and therefore also have distinguishable molecular weight values.

Figure 21A:
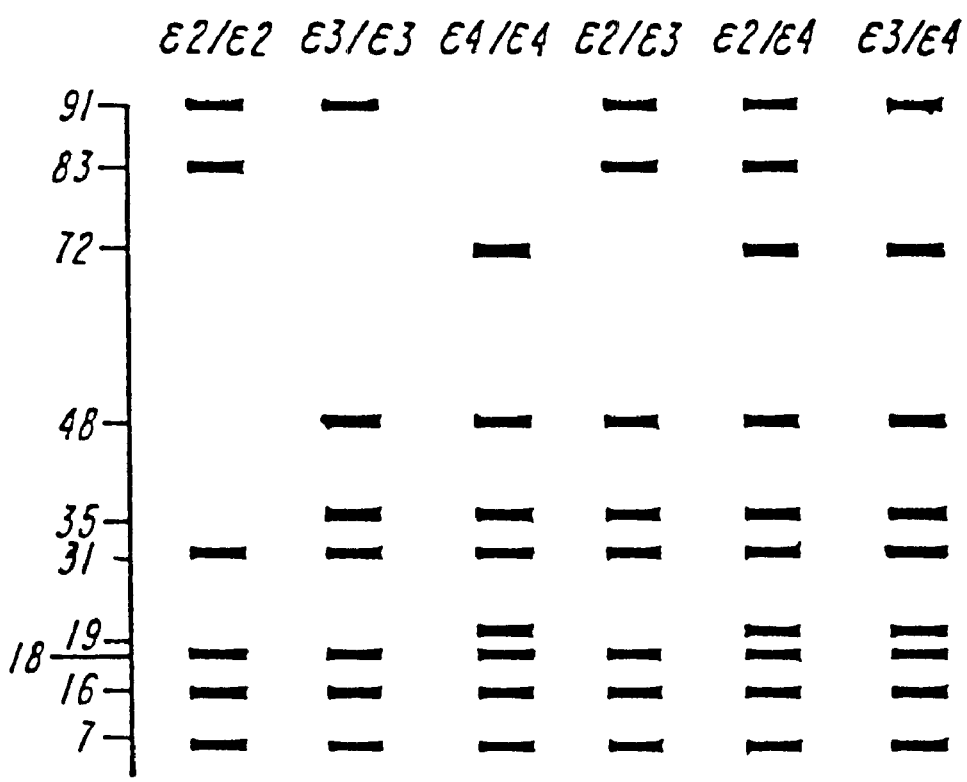
FIG. 21A shows the composite restriction pattern for various genotypes of apolipoprotein E.
Figure 21B:
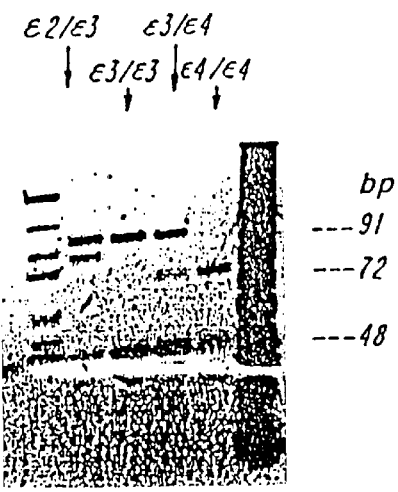
FIG. 21B shows the restriction pattern obtained in a 3.5% MetPhor Agarose Gel for various genotypes of apolipoprotein E.
Figure 21C:
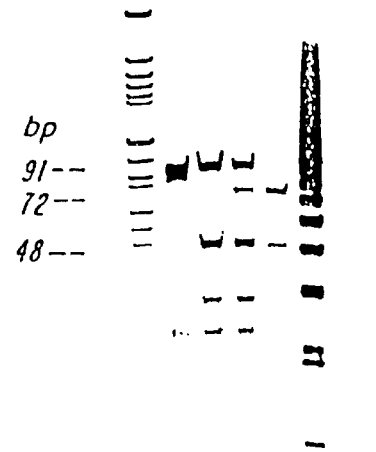
FIG. 21C shows the restriction pattern obtained in a 12% polyacrylamide gel for various genotypes of apolipoprotein E.
Figures 22A, 22B:
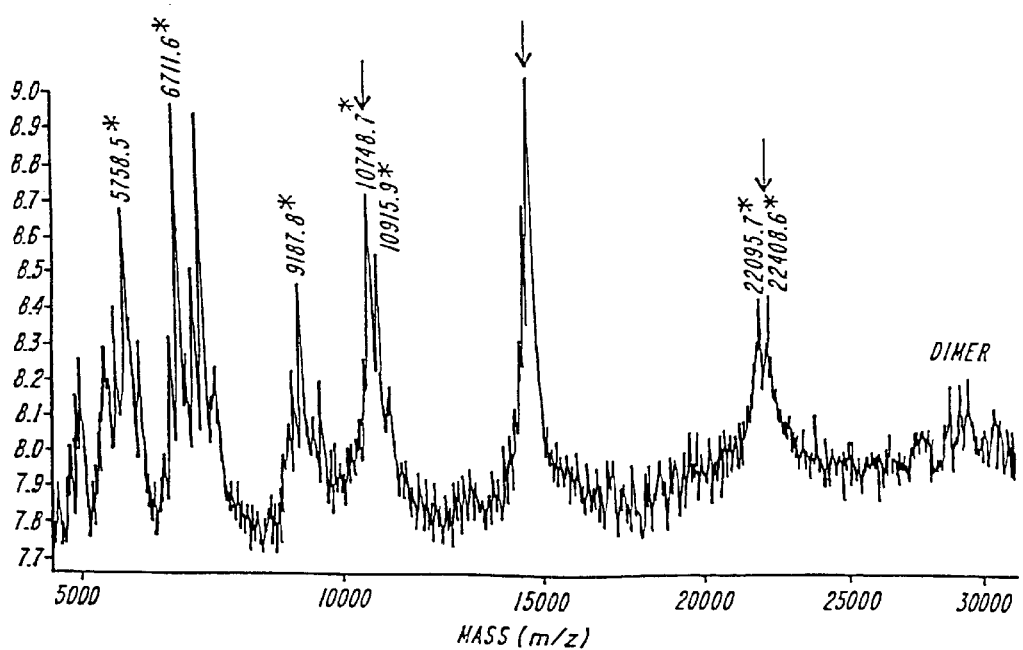
FIG. 22A is a chart showing the molecular weights of the 91, 83, 72, 48 and 35 base pair fragments obtained by restriction enzyme cleavage of the E2, E3, and E4 alleles of apolipoprotein E.
FIG. 22B is the mass spectra of the restriction product of a homozygous E4 apolipoprotein E genotype.
Figure 23A:
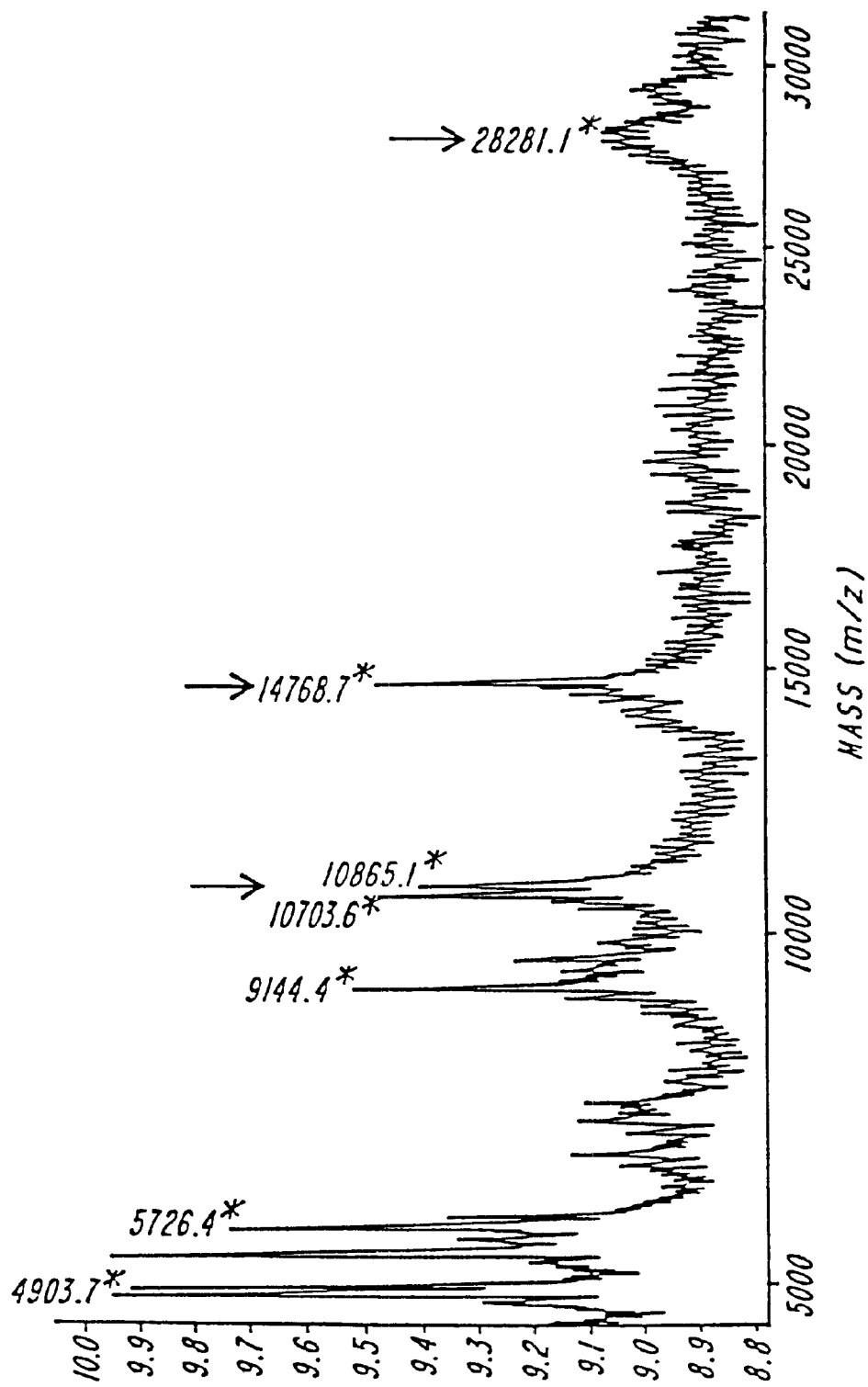
FIG. 23A is the mass spectra of the restriction product of a homozygous E3 apolipoprotein E genotype.
Figure 23B:
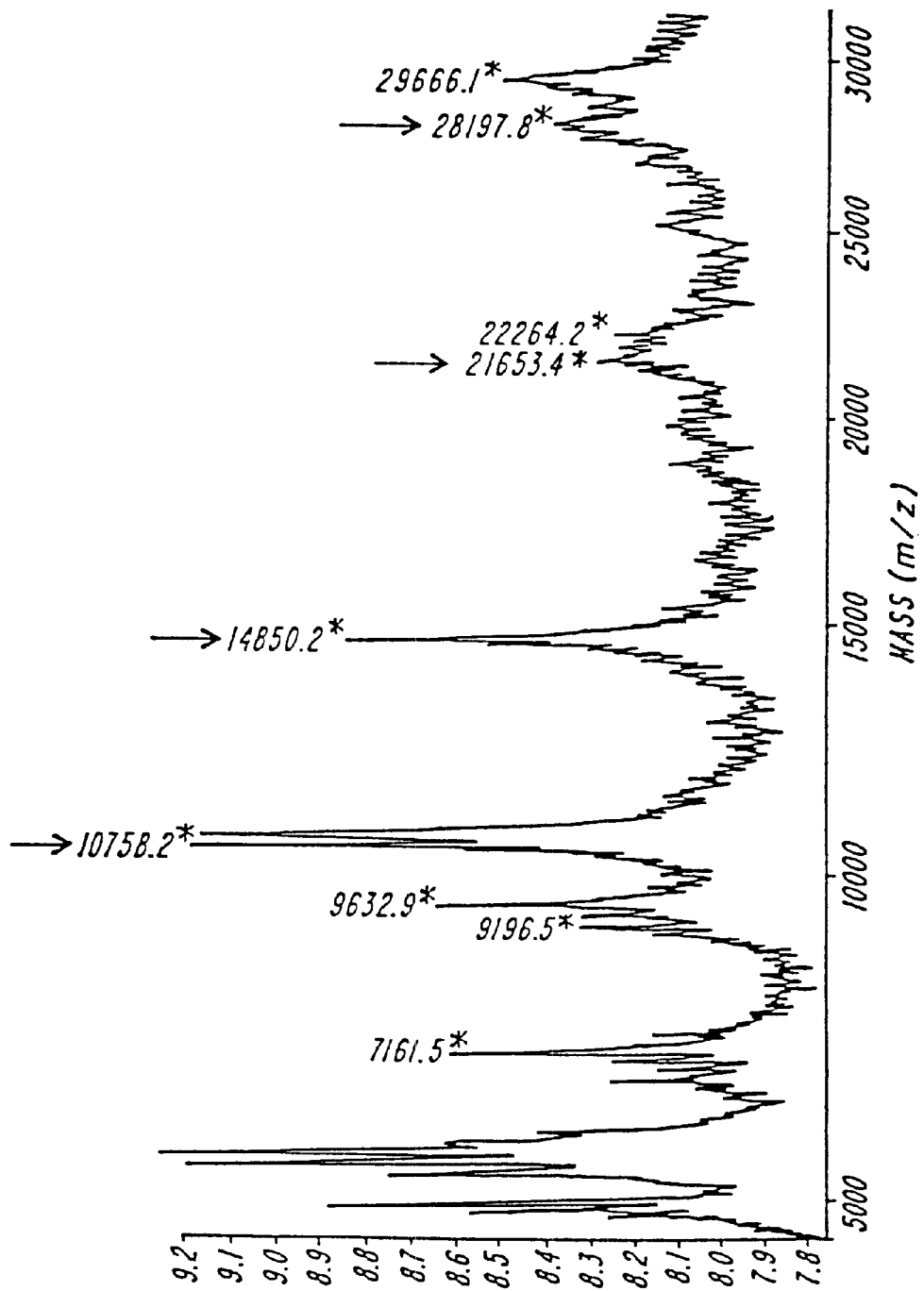
FIG. 23B is the mass spectra of the restriction product of a E3/E4 apolipoprotein E genotype.

As shown in FIGS. 21A–C, different Apolipoprotein E genotypes exhibit different restriction patterns in a 3.5% MetPhor Agarose Gel or 12% polyacrylamide gel. As shown in FIGS. 22A–B and 23A–B, the various apolipoprotein E genotypes can also be accurately and rapidly determined by mass spectrometry.

EXAMPLE 5

Detection of Hepatitis B Virus in Serum Samples

Materials and Methods

Sample Preparation

Phenol/chloroform extraction of viral DNA and the final ethanol precipitation was done according to standard protocols.

First PCR:

Each reaction was performed with 5 $\mu$l of the DNA preparation from serum. 15 pmol of each primer and 2 units Taq DNA polymerase (Perkin Elmer, Weiterstadt, Germany) were used. The final concentration of each dNTP was 200 $\mu$M, and the final volume of the reaction was 50 $\mu$l. 10× PCR buffer (Perkin Elmer, Weiterstadt, Germany) contained 100 mM Tris-HCl, pH 8.3, 500 mM KCl, 15 mM $MgCl_2$, and 0.01% gelatine (w/v).

Primer Sequences:

Primer 1: 5'-GCTTTGGGGCATGGACATTGACCCGTATAA-3' (SEQ ID NO 5)

Primer 2: 5'-CTGACTACTAATTCCCTGGATGCTGGGTCT-3' (SEQ ID NO 6)

Nested PCR:

Each reaction was performed either with 1 $\mu$l of the first reaction or with a 1:10 dilution of the first PCR as template, respectively. 100 pmol of each primer, 2.5 u Pfu(exo-) DNA polymerase (Stratagene, Heidelberg, Germany), a final concentration of 200 $\mu$M of each dNTPs and 5 $\mu$l 10× Pfu buffer (200 mM Tris-HCl, pH 8.75, 100 mM KCl, 100 mM $(NH_4)_2SO_4$, 20 mM $MgSO_4$, 1% Triton X-100, and 1 mg/ml BSA, (Stratagene, Heidelberg, Germany) were used in a final volume of 50 $\mu$l. The reactions were performed in a thermocycler (OmniGene, MWG-Biotech, Ebersberg, Germany) using the following program: 92° C. for 1 minute, 60° C. for 1 minute and 72° C. for 1 minute with 20 cycles. The sequences of the HBV oligodeoxynucleotides (purchased HPLC-purified at MWG-Biotech, Ebersberg, Germany) are provided below.

HBV 13: 5'-TTGCCTGAGTGCAGTATGGT-3' (SEQ.ID.No. 7)

HBV 15bio: Biotin-5'-AGCTCTATATCGGGAAGCCCT-3' (SEQ.ID.No. 8)

Purification of PCR Products:

For the recording of each spectrum, one PCR, 50 $\mu$l, (performed as described above) was used. Purification was done according to the following procedure: Ultrafiltration was done using Ultrafree-MC filtration units (Millipore, Eschborn, Germany) according to the protocol of the provider with centrifugation at 8000 rpm for 20 minutes. 25 $\mu$l (10 $\mu$g/$\mu$l) streptavidin Dynabeads (Dynal, Hamburg, Germany) were prepared according to the instructions of the manufacturer and resuspended in 25 $\mu$l of B/W buffer (10 mM Tris-HCl, pH7.5, 1 mM EDTA, 2 M NaCl). This suspension was added to the PCR samples still in the filtration unit and the mixture was incubated with gentle shaking for 15 minutes at ambient temperature. The suspension was transferred in a 1.5 ml Eppendorf tube and the supernatant was removed with the aid of a Magnetic Particle Collector, MPC, (Dynal, Hamburg, Germany). The beads were washed twice with 50 $\mu$l of 0.7 M ammonium citrate solution, pH 8.0 (the supernatant was removed each time using the MPC). Cleavage from the beads can be accomplished by using formamide at 90° C. The supernatant was dried in a speedvac for about an hour and resuspended in 4 $\mu$l of ultrapure water (MilliQ UF plus Millipore, Eschborn, Germany). The preparation was used for MALDI-TOF MS analysis.

MALDI-TOR MS:

Half a microliter of the sample was pipetted onto the sample holder, then immediately mixed with 0.5 $\mu$l matrix solution (0.7 M 3-hydroxypicolinic acid, 50% acetonitrile, 70 mM ammonium citrate). This mixture was dried at ambient temperature and introduced into the mass spectrometer. All spectra were taken in positive ion mode using a Finnigan MAT Vision 2000 (Finnigan MAT, Bremen, Germany), equipped with a reflectron 5 keV ion source, 20 keV postacceleration) and a 337 nm nitrogen laser. Calibration was done with a mixture of a 40-mer and a 100-mer. Each sample was measured with different laser energies. In the negative samples, the PCR product was detected neither with less nor with higher laser energies. In the positive samples the PCR product was detected at different places of the sample spot and also with varying laser energies.

Results

A nested PCR system was used for the detection of HBV DNA in blood samples employing oligonucleotides complementary to the c region of the HBV genome (primer 1: beginning at map position 1763, primer 2 beginning at map position 2032 of the complementary strand) encoding the HBV core antigen (HBV cAg). DNA was isolated from patients serum according to standard protocols. A first PCR was performed with the DNA from these preparations using a first set of primers. If HBV DNA was present in the sample, a DNA fragment of 269 bp was generated.

In the second reaction, primers which were complementary to a region within the PCR fragment generated in the first PCR were used. If HBV-related PCR products were present in the first PCR, a DNA fragment of 67 bp was generated (see FIG. 25A) in this nested PCR. The usage of a nested PCR system for detection provides a high sensitivity and also serves as a specificity control for the external PCR (Rolfs, A. et al., *PCR: Clinical Diagnostics and Research*, Springer, Heidelberg, 1992). A further advantage is that the amount of fragments generated in the second PCR is high enough to ensure an unproblematic detection although purification losses cannot be avoided.

The samples were purified using ultrafiltration to remove the primers prior to immobilization on streptavidin Dyna-Beads. This purification was done because the shorter primer fragments were immobilized in higher yield on the beads due to steric reasons. The immobilization was done directly on the ultrafiltration membrane to avoid substance losses due to unspecific absorption on the membrane. Following immobilization, the beads were washed with ammonium citrate to perform cation exchange (Pieles, U. et al., (1992) *Nucleic Acids Res* 21: 3191–3196). The immobilized DNA was cleaved from the beads using 25% ammonia which allows cleavage of DNA from the beads in a very short time, but does not result in an introduction of sodium cations.

The nested PCRs and the MALDI TOF analysis were performed without knowing the results of serological analysis. Due to the unknown virus titer, each sample of the first PCR was used undiluted as template and in a 1:10 dilution, respectively.

Sample 1 was collected from a patient with chronic active HBV infection, was positive in HBs and HBe-antigen tests, but negative in a dot blot analysis. Sample 2 was a serum sample from a patient with an active HBV infection and a massive viremia who was HBV positive in a dot blot analysis. Sample 3 was a denatured serum sample, therefore no serological analysis could be performed but an increased level of transaminases indicating liver disease was detected. In autoradiograph analysis (FIG. 24), the first PCR of this sample was negative. Nevertheless, there was some evidence of HBV infection. This sample is of interest for MALDI-TOF analysis, because it demonstrates that even low-level amounts of PCR products can be detected after the purification procedure. Sample 4 was from a patient who was cured of HBV infection. Samples 5 and 6 were collected from patients with a chronic active HBV infection.

Figure 24:
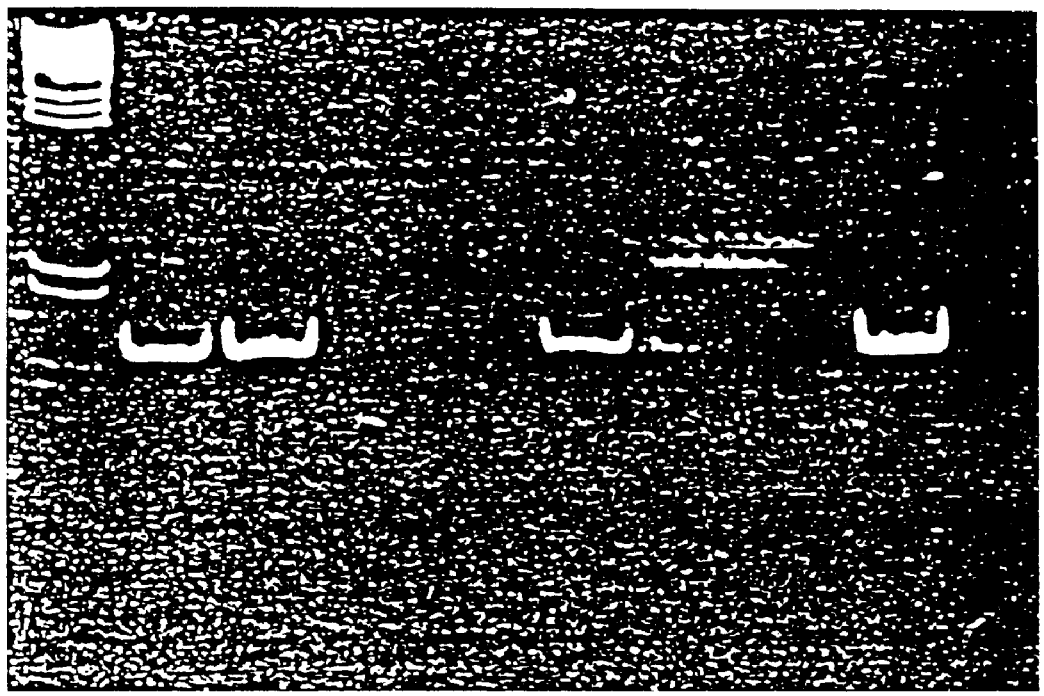
FIG. 24 is an autoradiograph of a 7.5% polyacrylamide gel in which 10% (5 µl) of each PCR was loaded. Sample M: pBR322 AluI digested; sample 1: HBV positive in serological analysis; sample 2: also HBV positive; sample 3: without serological analysis but with an increased level of transaminases, indicating liver disease; sample 4: HBV negative; sample 5: HBV positive by serological analysis; sample 6: HBV negative (−) negative control; (+) positive control). Staining was done with ethidium bromide.

FIG. 24 shows the results of a PAGE analysis of the nested PCR reaction. A PCR product is clearly revealed in samples 1, 2, 5 and 6. In sample 4 no PCR product was generated; it is indeed HBV negative, according to the serological analysis. Amplification artifacts are visible in lanes 2, 5 and 6, if non-diluted template was used. These artifacts were not generated if the template was used in a 1:10dilution. In sample 3, PCR product was only detectable if the template was not diluted. The results of PAGE analysis are in agreement with the data obtained by serological analysis except for sample 3 as discussed above.

Figure 25A:
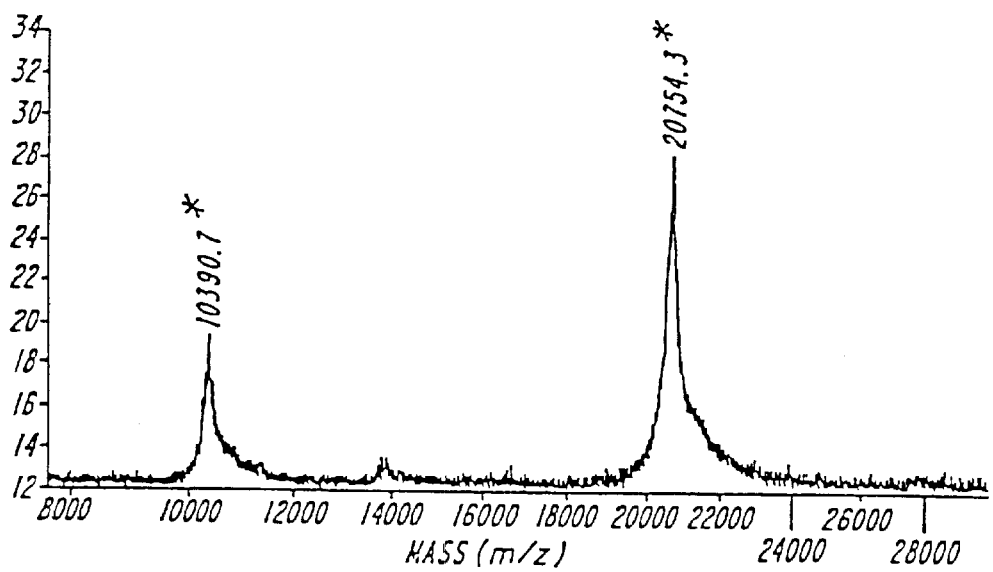
FIG. 25A is a mass spectrum of sample 1, which is HBV positive. The signal at 20754 Da represent HBV related PCR product (67 nucleotides, calculated mass: 20735 Da). The mass signal at 10390 Da represents $[M+2H]^{2+}$ signal (calculated: 10378 Da).

FIG. 25A shows a mass spectrum of a nested PCR product from sample number 1 generated and purified as described above. The signal at 20754 Da represents the single stranded PCR product (calculated: 20735 Da, as the average mass of both strands of the PCR product cleaved from the beads). The mass difference of calculated and obtained mass is 19 Da (0.09%). As shown in FIG. 25A, sample number 1 generated a high amount of PCR product, resulting in an unambiguous detection.

Figure 25B:
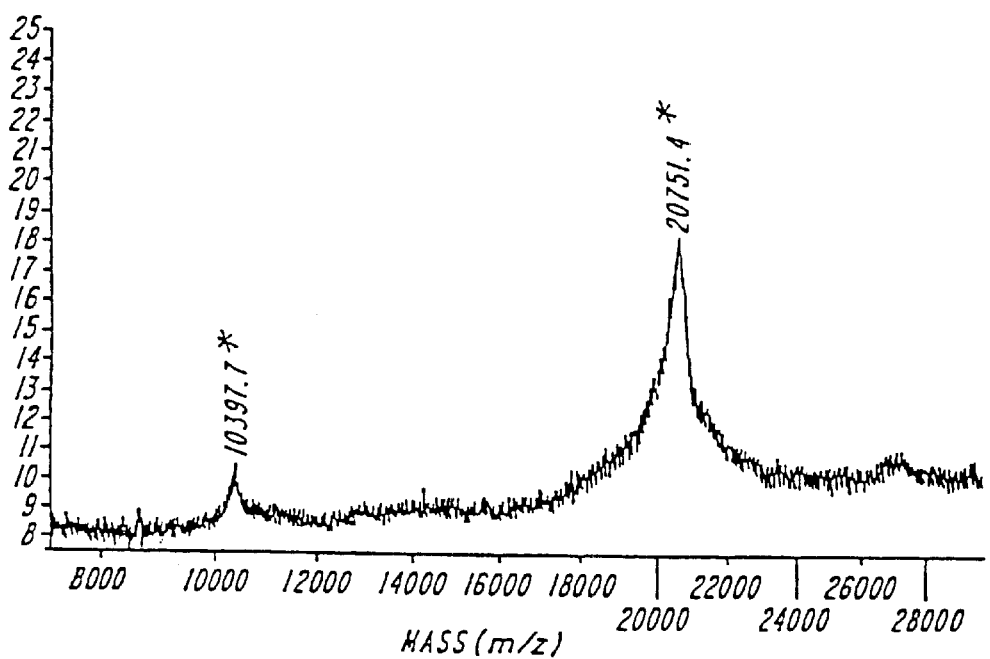
FIG. 25B is a mass spectrum of sample 3, which is HBV negative corresponding to PCR, serological and dot blot based assays. The PCR product is generated only in trace amounts. Nevertheless, it is unambiguously detected at 20751 Da (calculated: 20735 Da). The mass signal at 10397 Da represents the $[M+2H]^{2+}$ molecule ion (calculated: 10376 Da).
Figure 25C:
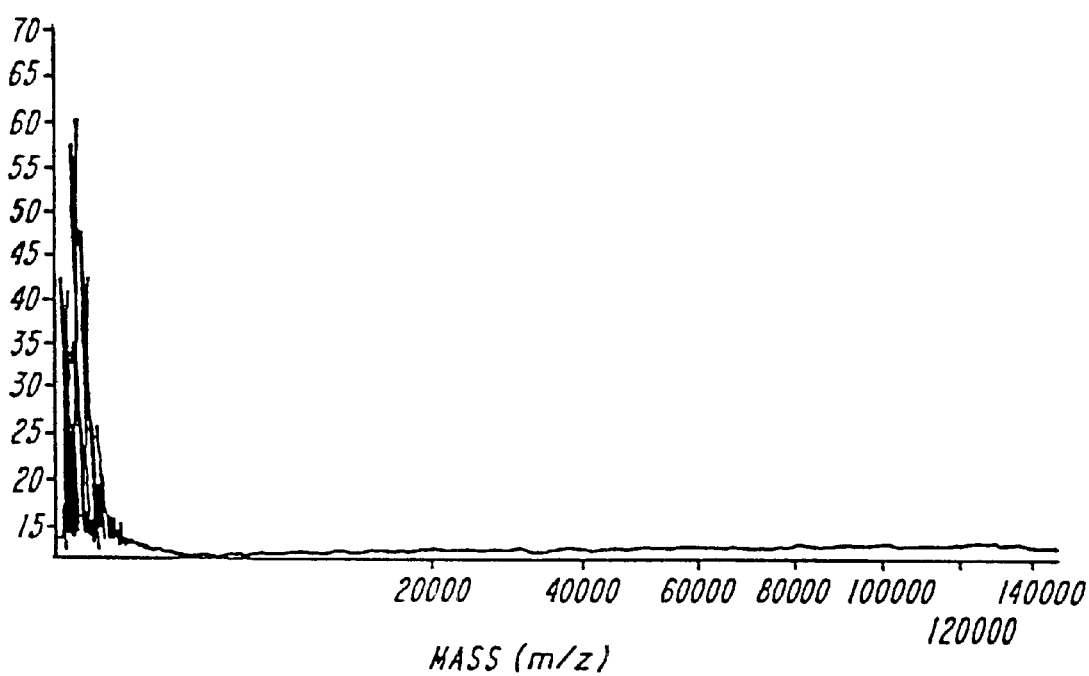
FIG. 25C is a mass spectrum of sample 4, which is HBV negative, but CMV positive. As expected, no HBV specific signals could be obtained.

FIG. 25B shows a spectrum obtained from sample number 3. As depicted in FIG. 24, the amount of PCR product generated in this section is significantly lower than that from sample number 1. Nevertheless, the PCR product is clearly revealed with a mass of 20751 Da (calculated 20735). The mass difference is 16 Da (0.08%). The spectrum depicted in FIG. 25C was obtained from sample number 4 which is HBV negative (as is also shown in FIG. 24). As expected no signals corresponding to the PCR product could be detected. All samples shown in FIGS. 25A–C were analyzed with MALDI-TOF MS, whereby PCR product was detected in all HBV positive samples, but not in the HBV negative samples. These results were reproduced in several independent experiments.

EXAMPLE 6

Analysis of Ligase Chain Reaction Products Via MALDI-TOF Mass Spectrometry

Materials and Methods
Oligodeoxynucleotides

Except for the biotinylated oligonucleotide, all other oligonucleotides were synthesized in a 0.2 µmol scale on a MilliGen 7500 DNA Synthesizer (Millipore, Bedford, Mass., USA) using the β-cyanoethylphosphoamidite method (Sinha, N. D. et al., (1984) *Nucleic Acids Res*. 12: 4539–4577). The oligodeoxynucleotides were RP-HPLC-purified and deprotected according to standard protocols. The biotinylated oligodeoxynucleotide was purchased (HPLC-purified) from Biometra, Gottingen, Germany). Sequences and calculated masses of the oligonucleotides used:

Oligodeoxynucleotide A: 5'-p-TTGTGCCACGCGGTTGGGAATGTA-3' (7521 Da) (SEQ.ID.No. 9)

Oligodeoxynucleotide B: 5'-p-AGCAACGACTGTTTGCCCGCCAGTTG-3' (7948 Da) (SEQ.ID.No 10)

Oligodeoxynucleotide C: 5'-bio-TACATTCCCAACCGCGTGGCACAAC-3' (7960 Da) (SEQ.ID.No. 11)

Oligodeoxynucleotide D: 5'-p-AACTGGCGGGCAAACAGTCGTTGCT-3' (7708 Da) (SEQ.ID.No. 12)

5'-Phosphorylation of Oligonucleotides A and D

This was performed with polynucleotide Kinase (Boehringer, Mannheim, Germany) according to published procedures; the 5'-phosphorylated oligonucleotides were used unpurified for LCR.

Ligase Chain Reaction

The LCR was performed with Pfu DNA ligase and a ligase chain reaction kit (Stratagene, Heidelberg, Germany) containing two different pBluescript KII phagemids, one carrying the wildtype form of the *E.coli* lacI gene and the other one a mutant of the gene with a single point mutation of bp 191 of the lacI gene. The following LCR conditions were used for each reaction: 100pg template DNA (0.74 fmol) with 500 pg sonified salmon sperm DNA as carrier, 25 ng (3.3 pmol) of each 5'-phosphorylated oligonucleotide, 20 ng (2.5 pmol) of each non-phosphorylated oligonucleotide, and 4 u Pfu DNA ligase in a final volume of 20 µl buffered by Pfu DNA ligase reaction buffer (Stratagene, Heidelberg, Germany). In a model experiment, a chemically synthesized ss 50-mer was used (1 fmol) as template, and in this case oligo C was also biotinylated. All reactions were performed in a thermocycler (OmniGene, MWG-Biotech, Ebersberg, Germany) with the following program: 4 minutes 92° C., 2 minutes 60° C. and 25 cycles of 20 seconds 92° C., 40 seconds 60° C. Except for HPLC analysis, the biotinylated ligation educt C was used. In a control experiment the biotinylated and non-biotinylated oligonucleotides revealed the same gel electrophoretic results. The reactions were analyzed on 7.5% polyacrylamide gels. Ligation product 1 (oligo A and B) calculated mass: 15450 Da; ligation product 2 (oligo C and D) calculated mass: 15387 Da.

SMART-HPLC

Ion exchange HPLC (IE HPLC) was performed on the SMART-system (Pharmacia, Freibrug, Germany) using a Pharmacia Mono Q, PC 1.6/5 column. Eluents were buffer A (25 mM Tris-HCl, 1 mM EDTA and 0.3 M NaCl at pH 8.0) and buffer B (same as A, but 1 M NaCl). Starting with 100% A for 5 minutes at a flow rate of 50 µl/min a gradient was applied from 0 to 70% B in 30 minutes, then increased to 100% B in 2 minutes and held at 100% B for 5 minutes. Two pooled LCR volumes (40 µl) performed with either wildtype or mutant template were injected.

Sample Preparation for MALDI-TOF-MS Preparation of immobilized DNA: For the recording of each spectrum two LCRs (performed as described above) were pooled and diluted 1:1 with 2× B/W buffer (10 mM Tris-HCl, pH 7.5, 1 mM EDTA, 2 M NaCl). To the samples 5 µl streptavidin DynaBeads (Dynal, Hamburg, Germany) were added and the mixture was allowed to bind with gentle shaking for 15 minutes at ambient temperature. The supernatant was removed using a Magnetic Particle Collector, MPC (Dynal, Hamburg, Germany) and the beads were washed twice with 50 µl of 0.7 M ammonium citrate solution (pH 8.0) (the supernatant was removed each time using the MPC). The beads were resuspended in 1 µl of ultrapure water (MilliQ, Millipore, Bedford, Mass., USA). This suspension was directly used for MALDI-TOF-MS analysis as described below.

Combination of ultrafiltration and streptavidin Dyna-Beads: For the recording of spectrum two LCRs (performed as described above) were pooled, diluted 1:1 with 2× B/W buffer and concentrated with a 5000 NMWL Ultrafree-MC filter unit (Millipore, Eschborn, Germany) according to the instructions of the manufacturer. After concentration, the samples were washed with 300 µl 1× B/W buffer and 5 µl streptavidin DynaBeads were added. The beads were washed once on the Ultrafree-MC filtration unit with 300 µl of 1× B/W buffer and processed as described above. The beads were resuspended in 30 to 50 µl of 1× B/W buffer and transferred in a 1.5 ml Eppendorf tube. The supernatant was removed and the beads were washed twice with 50 µl of 0.7 M ammonium citrate (pH 8.0). Finally, the beads were washed once with 30 µl of acetone and resuspended in 1 µl of ultrapure water. The ligation mixture, after immobilization on the beads, was used for MALDI-TOF-MS analysis as described below.

MALDI-TOF-MS

A suspension of streptavidin-coated magnetic beads with the immobilized DNA was pipetted onto the sample holder, then immediately mixed with 0.5 µl matrix solution (0.7 M 3-hydroxypicolinic acid in 50% acetonitrile, 70 mM ammonium citrate). This mixture was dried at ambient temperature and introduced into the mass spectrometer. All spectra were taken in positive ion mode using a Finnigan MAT Vision 2000 (Finnigan MAT, Bremen, Germany), equipped with a reflectron (5 keV ion source, 20 keV postacceleration) and a nitrogen laser (337 nm). For the analysis of Pfu DNA ligase, 0.5 µl of the solution was mixed on the sample holder with 1 µl of matrix solution and prepared as described above. For the analysis of unpurified LCRs, 1 µl of an LCR was mixed with 1 µl matrix solution.

Results and Discussion

Figure 26:
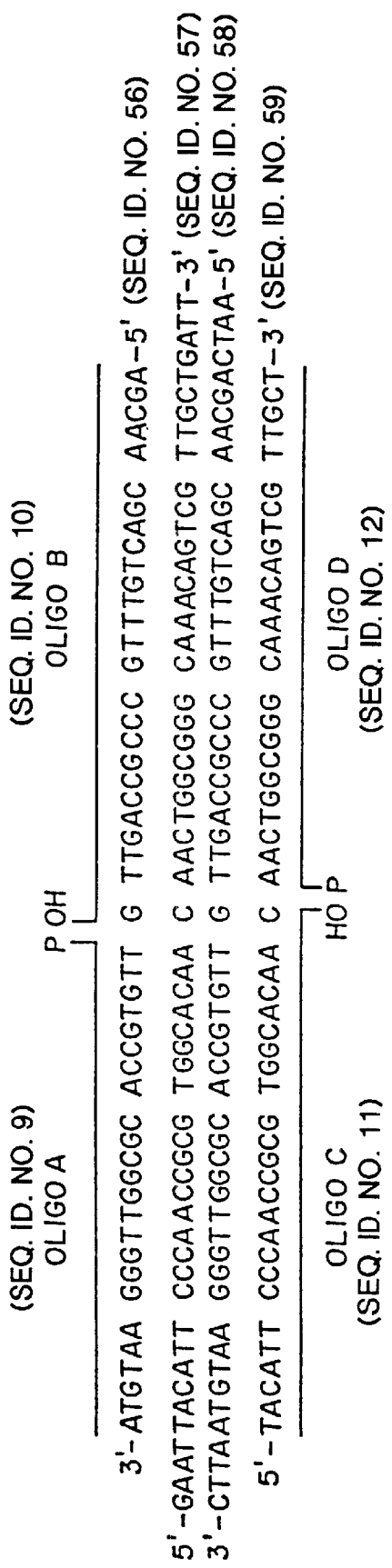
FIG. 26 shows a part of the *E.coli* lacI gene with binding sites of the complementary oligonucleotides used in the ligase chain reaction (LCR). Here the wildtype sequence is displayed. The mutant contains a point mutation at bp 191 which is also the site of ligation (bold). The mutation is a C to T transition (G to A, respectively). This leads to a T-G mismatch with oligo A (and A-C mismatch with oligo B, respectively).

The *E. coli* lacI gene served as a simple model system to investigate the suitability of MALDI-TOF-MS as a detection method for products generated in ligase chain reactions. This template system consists of an *E.coli* lacI wildtype gene in a pBluescript KII phagemid and an *E. coli* lacI gene carrying a single point mutation at bp 191 (C to T transition) in the same phagemid. Four different oligonucleotides were used, which were ligated only if the *E. coli* lacI wildtype gene was present (FIG. 26).

Figure 27:
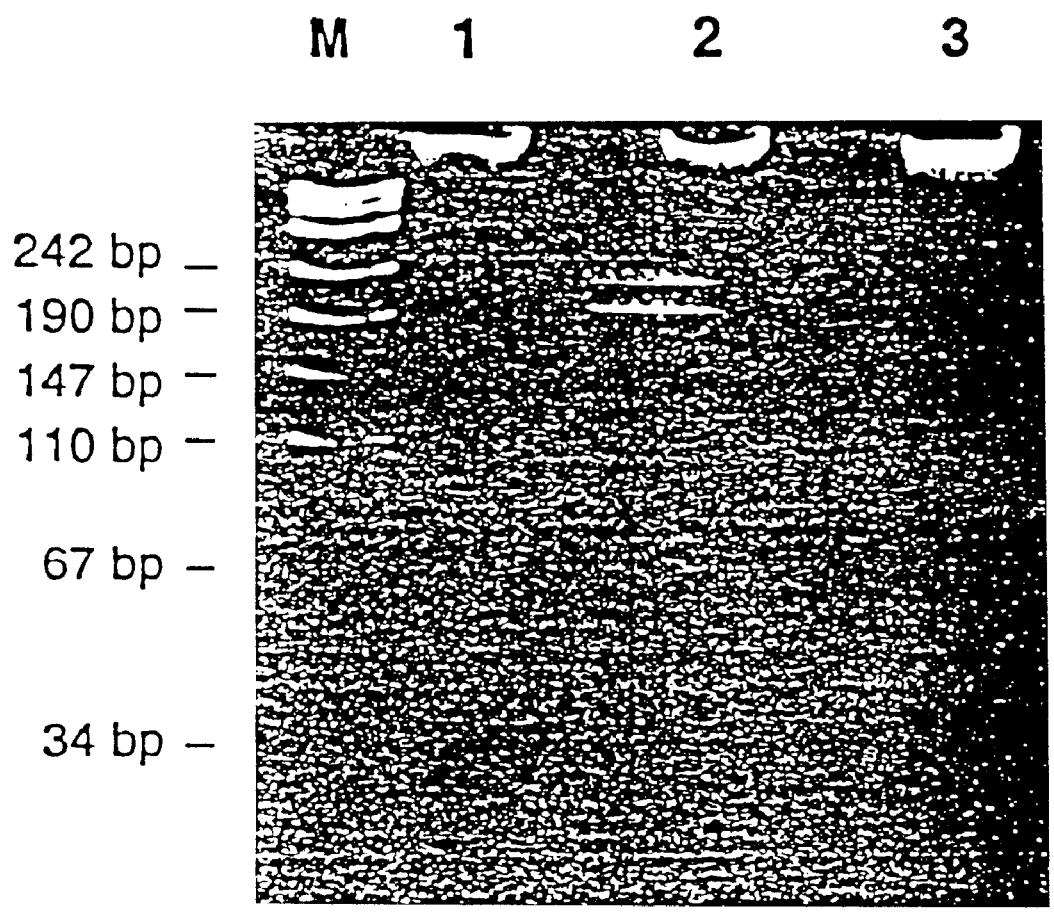
FIG. 27 is a 7.5% polyacrylamide gel stained with ethidium bromide. M: chain length standard (pUC19 DNA, MspI digested). Lane 1: LCR with wildtype template. Lane 2: LCR with mutant template. Lane 3: (control) LCR without template. The ligation product (50 bp) was only generated in the positive reactive containing wildtype template.
Figure 28:
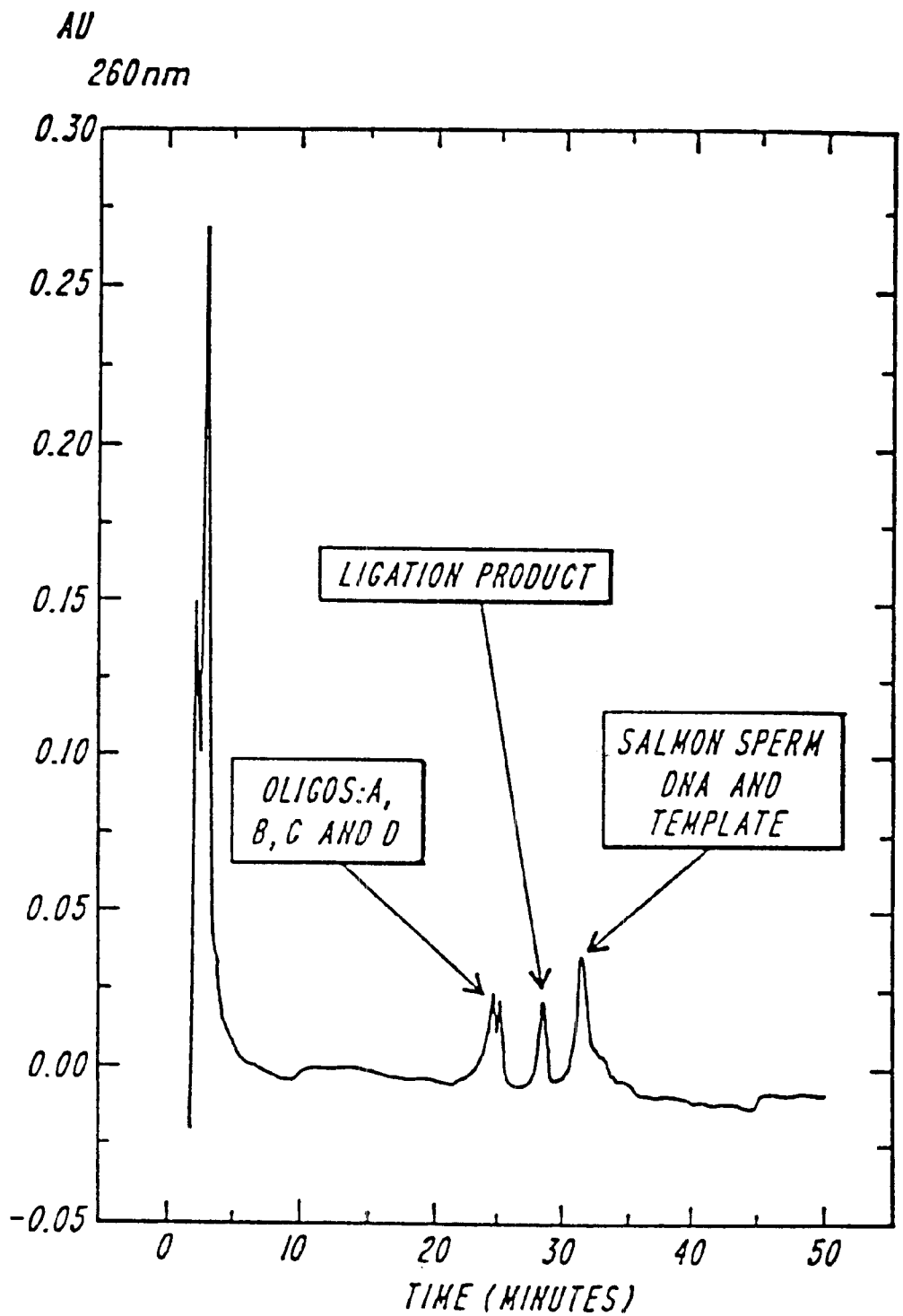
FIG. 28 is an HPLC chromatogram of two pooled positive LCRs.
Figure 29:
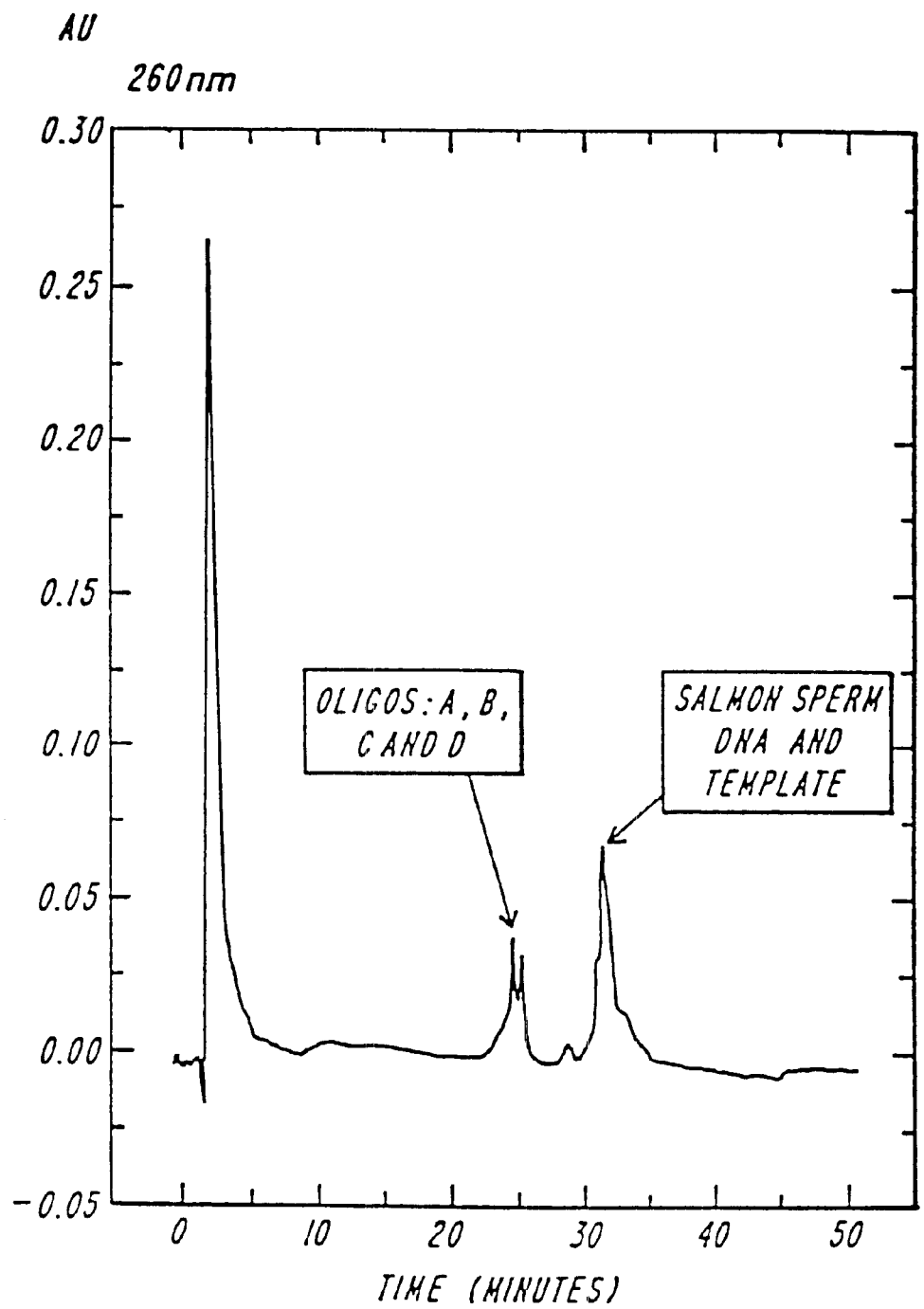
FIG. 29 shows an HPLC chromatogram under the same conditions but using the mutant template. The small signal of the ligation product is due to either template-free, ligation of the educts or to a ligation at a (G-T, A-C) mismatch. The 'false positive' signal is significantly lower than the signal of ligation product with wildtype template depicted in FIG. 28. The analysis of ligation educts leads to 'double-peaks' because two of the oligonucleotides are 5'-phosphorylated.

LCR conditions were optimized using Pfu DNA ligase to obtain at least 1 pmol ligation product in each positive reaction. The ligation reactions were analyzed by polyacrylamide gel electrophoresis (PAGE) and HPLC on the SMART system (FIGS. 27, 28 and 29). FIG. 27 shows a PAGE of a positive LCR with wildtype template (lane 1), a negative LCR with mutant template (1 and 2) and a negative control which contains enzyme, oligonucleotides and no template. The gel electrophoresis clearly shows that the ligation product (50 bp) was produced only in the reaction with wildtype template whereas neither the template carrying the point mutation nor the control reaction with salmon sperm DNA generated amplification products. In FIG. 28, HPLC was used to analyze two pooled LCRs with wildtype template performed under the same conditions. The ligation product was clearly revealed. FIG. 29 shows the results of a HPLC in which two pooled negative LCRs with mutant template were analyzed. These chromatograms confirm the data shown in FIG. 27 and the results taken together clearly demonstrate, that the system generates ligation products in a significant amount only if the wildtype template is provided.

Appropriate control runs were performed to determine retention times of the different compounds involved in the LCR experiments. These include the four oligonucleotides (A, B, C, and D), a synthetic ds 50-mer (with the same sequence as the ligation product), the wildtype template DNA, sonicated salmon sperm DNA and the Pfu DNA ligase in ligation buffer.

Figure 30A:
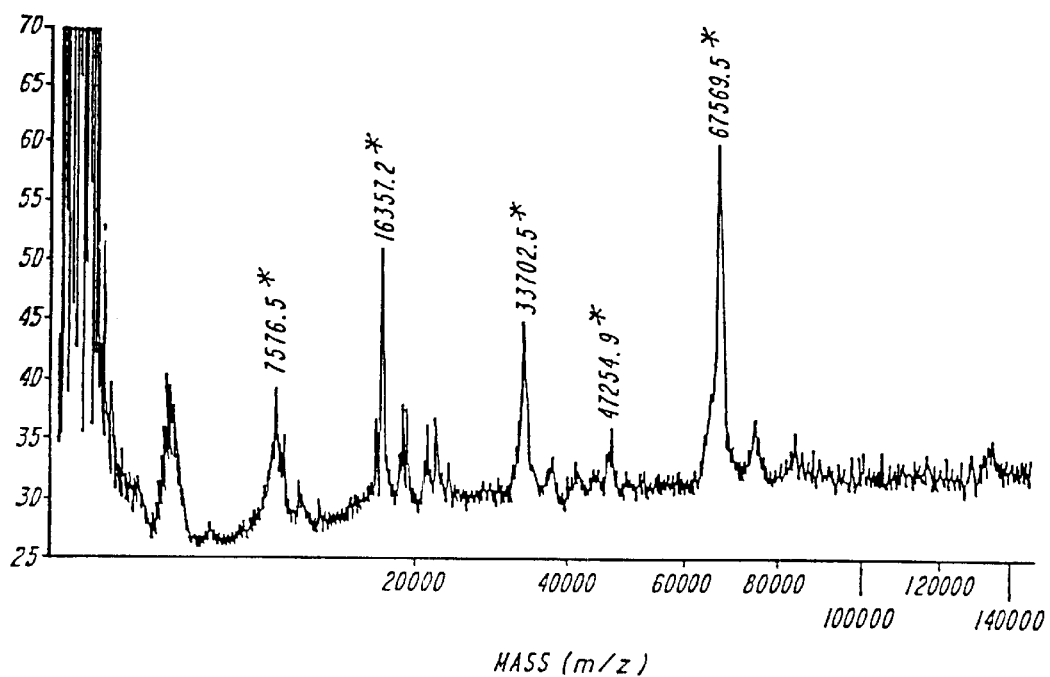
FIG. 30A shows the complex signal pattern obtained by MALDI-TOF-MS analysis of Pfu DNA-ligase solution.
Figure 30B:
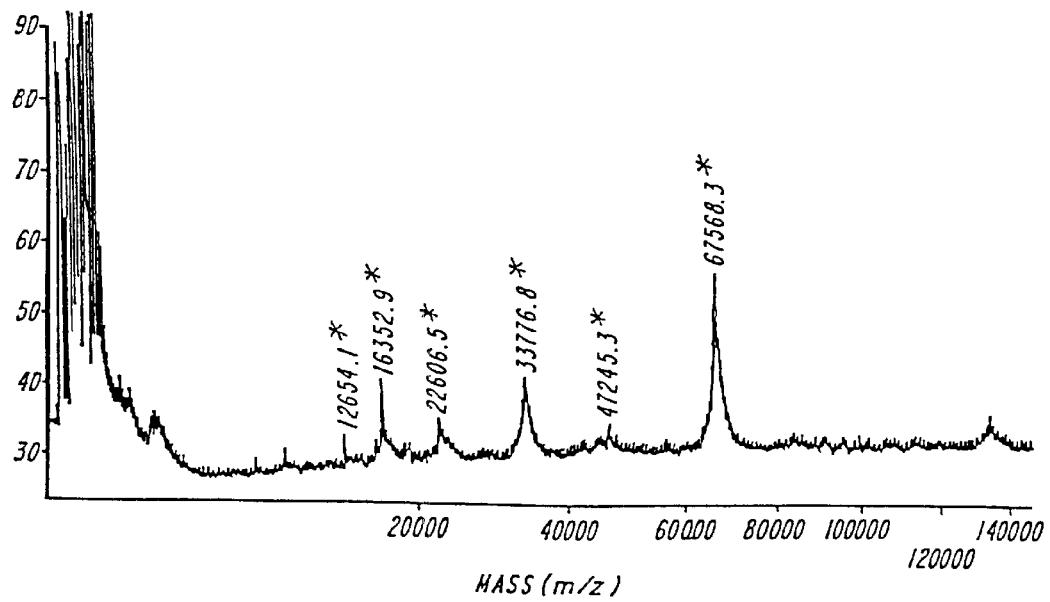
FIG. 30B shows a MALDI-TOF-spectrum of an unpurified LCR. The mass signal 67569 Da probably represents the Pfu DNA ligase.

In order to test which purification procedure should be used before a LCR reaction can be analyzed by MALDI-TOF-MS, aliquots of an unpurified LCR (FIG. 30A) and aliquots of the enzyme stock solution (FIG. 30B) were analyzed with MALDI-TOF-MS. It turned out that appropriate sample preparation is absolutely necessary since all signals in the unpurified LCR correspond to signals obtained in the MALDI-TOF-MS analysis of the Pfu DNA ligase. The calculated mass values of oligo A and the ligation product are 7521 Da and 15450 Da, respectively. The data in FIGS. 30A–B show that the enzyme solution leads to mass signals which do interfere with the expected signals of the ligation educts and products and therefore makes an unambiguous signal assignment impossible. Furthermore, the spectra showed signals that the detergent Tween 20 that is in the enzyme storage buffer influences the crystallization behavior of the analyte/matrix mixture in an unfavorable way.

In one purification format streptavidin-coated magnetic beads were used. As was shown in a recent paper, the direct desorption of DNA immobilized by Watson-Crick base pairing to a complementary DNA fragment covalently bound to the beads is possible and the non-biotinylated strand will be desorbed exclusively (Tang, K. et al., *Nucleic Acids Res.* 23: 3126–3131 (1995)). This approach in using immobilized ds DNA ensures that only the non-biotinylated strand will be desorbed. If non-immobilized ds DNA is analyzed both strands are desorbed (Tang, K. et al., *Rapid Comm. Mass Spectrom.* 7: 183–186 (1994)) leading to broad signals depending on the mass difference of the two strands. Therefore, employing this system for LCR, only the non-ligated oligonucleotide A, with a calculated mass of 7521

Da, and the ligation product from oligo A and oligo B (calculated mass: 15450 Da) will be desorbed if oligo C is biotinylated at the 5' end and immobilized on steptavidin-coated beads. This results in a simple and unambiguous identification of the LCR educts and products.

Figure 31A:
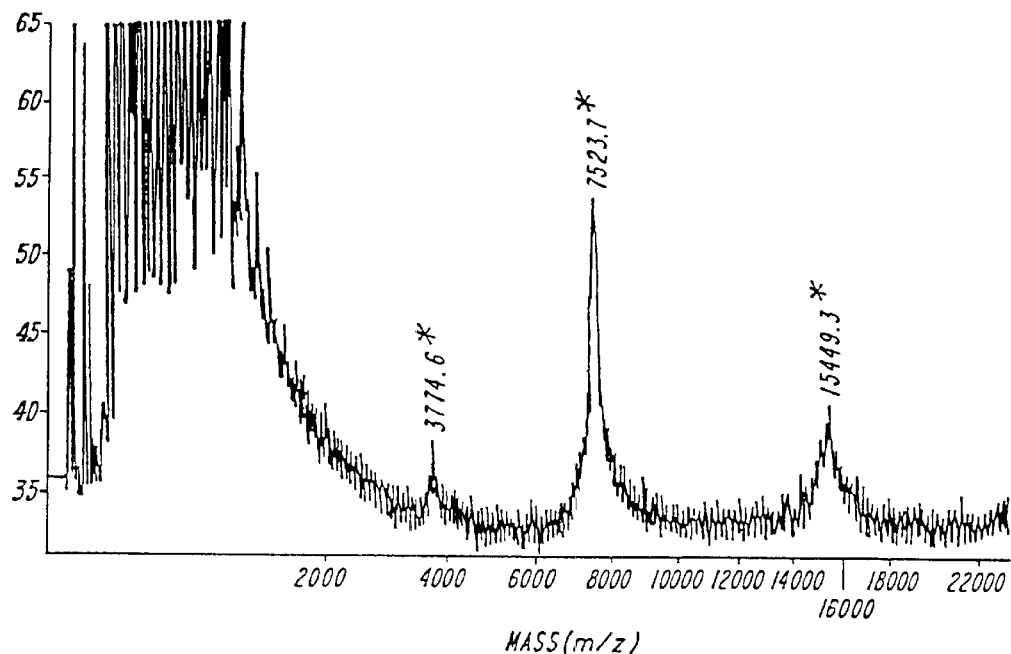
FIG. 31A shows a MALDI-TOF spectrum of two pooled positive LCRs. The signal at 7523 Da represents unligated oligo A (calculated: 7521 Da) whereas the signal at 15449 Da represents the ligation product (calculated: 15450 Da). The signal at 3774 Da is the $[M+2H]^{2+}$ signal of oligo A. The signals in the mass range lower than 2000 Da are due to the matrix ions. The spectrum corresponds to lane 1 in FIG. 27 and to the chromatogram in FIG. 28.
Figure 31B:
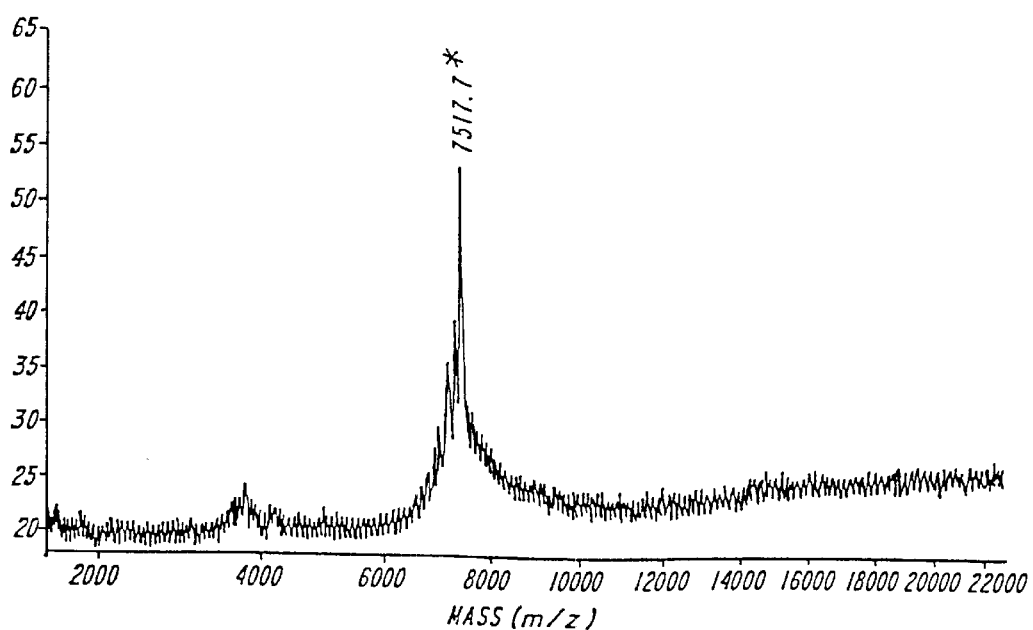
FIG. 31B shows a spectrum of two pooled negative LCRs (mutant template). The signal at 7517 Da represents oligo A (calculated: 7521 Da).
Figure 32:
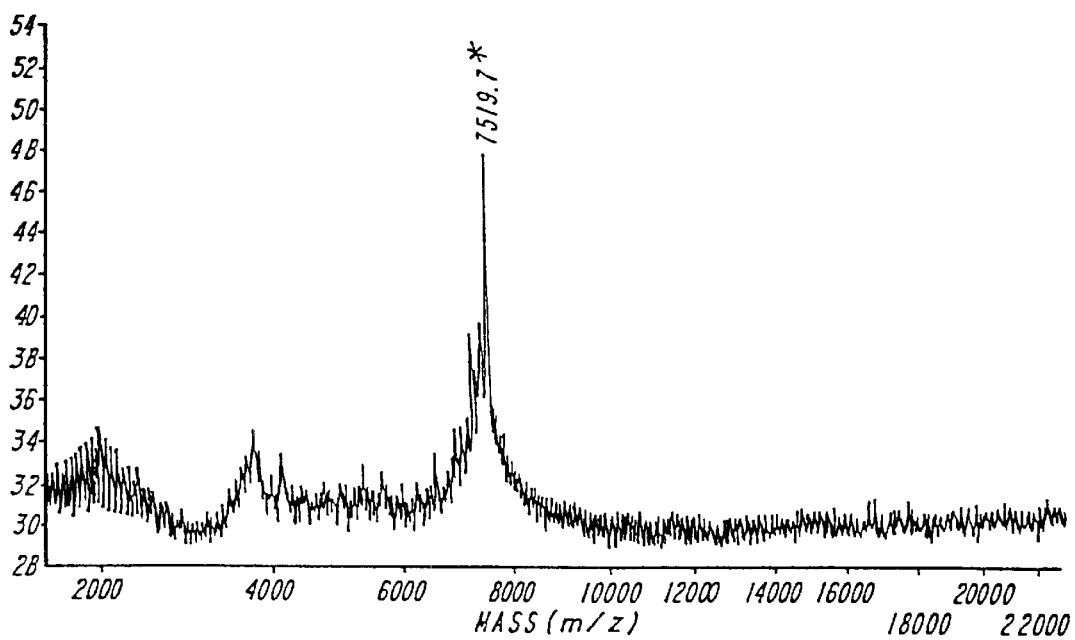
FIG. 32 shows a spectrum obtained from two pooled LCRs in which only salmon sperm DNA was used as a negative control: only oligo A could be detected, as expected.

FIG. 31A shows a MALDI-TOF mass spectrum obtained from two pooled LCRs (performed as described above) purified on streptavidin DynaBeads and desorbed directly from the beads, indicating that the purification method used was efficient (compared with FIGS. 30A–B). A signal which represents the unligated oligo A and a signal which corresponds to the ligation product could be detected. The agreement between the calculated and the experimentally found mass values is remarkable and allows an unambiguous peak assignment and accurate detection of the ligation product. In contrast, no ligation product but only oligo A could be detected in the spectrum obtained from two pooled LCRs with mutated template (FIG. 31B). The specificity and selectivity of the LCR conditions and the sensitivity of the MALDI-TOF detection is further demonstrated when performing the ligation reaction in the absence of a specific template. FIG. 32 shows a spectrum obtained from two pooled LCRs in which only salmon sperm DNA was used as a negative control; only oligo A could be detected, as expected.

While the results shown in FIG. 31A can be correlated to lane 1 of the gel in FIG. 27, the spectrum shown in FIG. 31B is equivalent to lane 2 in FIG. 27, and finally also the spectrum in FIG. 32 corresponds to lane 3 in FIG. 27. The results are in congruence with the HPLC analysis presented in FIGS. 28 and 29. While both gel electrophoresis (FIG. 27) and HPLC (FIGS. 28 and 29) reveal either an excess or almost equal amounts of ligation product over ligation educts, the analysis by MALDI-TOF mass spectrometry produces a smaller signal for the ligation product (FIG. 31A).

The lower intensity of the ligation product signal could be due to different desorption/ionization efficiencies between 24- and a 50-mer. Since the $T_m$ value of a duplex with 50 compared to 24 base pairs is significantly higher, more 24-mer could be desorbed. A reduction in signal intensity can also result from a higher degree of fragmentation in the case of the longer oligonucleotides.

Regardless of the purification with streptavidin DynaBeads, FIG. 32 reveals traces of Tween 20 in the region around 2000 Da. Substances with a viscous consistency negatively influence the process of crystallization and therefore can be detrimental to mass spectrometer analysis. Tween 20 and also glycerol which are part of enzyme storage buffers therefore should be removed entirely prior to mass spectrometer analysis. For this reason an improved purification procedure which includes an additional ultrafiltration step prior to treatment with DynaBeads was investigated. Indeed, this sample purification resulted in a significant improvement of MALDI-TOF mass spectrometric performance.

Figure 33A:
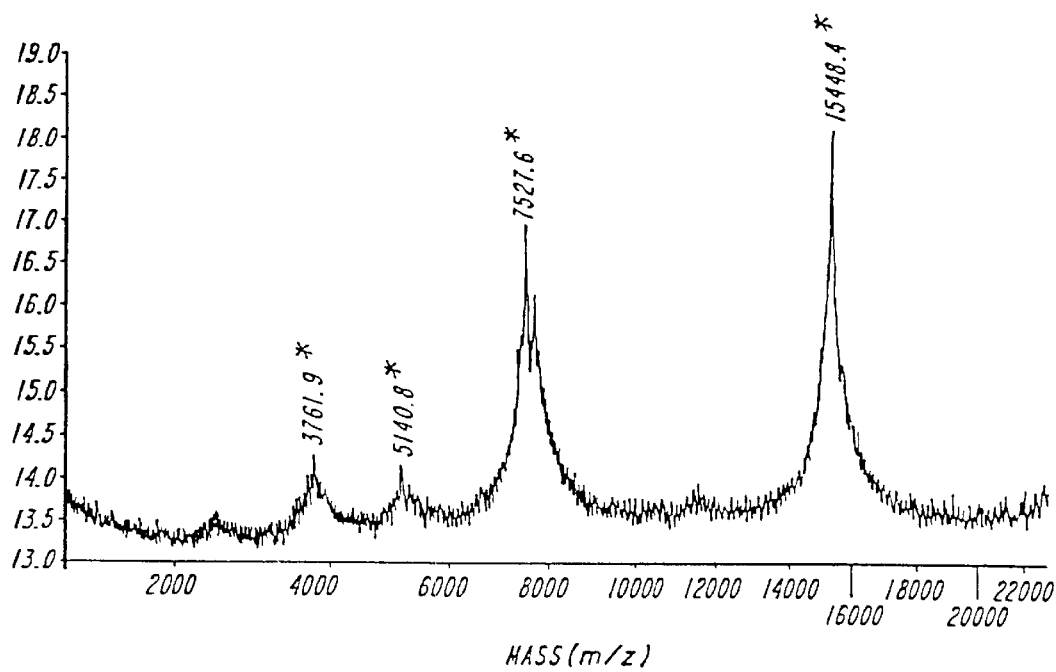
FIG. 33A shows a spectrum of two pooled positive LCRs. The purification was done with a combination of ultrafiltration and streptavidin DynaBeads as described in the text. The signal at 15448 Da represents the ligation product (calculated: 15450 Da). The signal at 7527 represents oligo A (calculated: 7521 Da). The signals at 3761 Da is the $[M+2H]^{2+}$ signal of oligo A, where as the signal at 5140 Da is the $[M+3H]^{2+}$ signal of the ligation product.
Figure 33B:
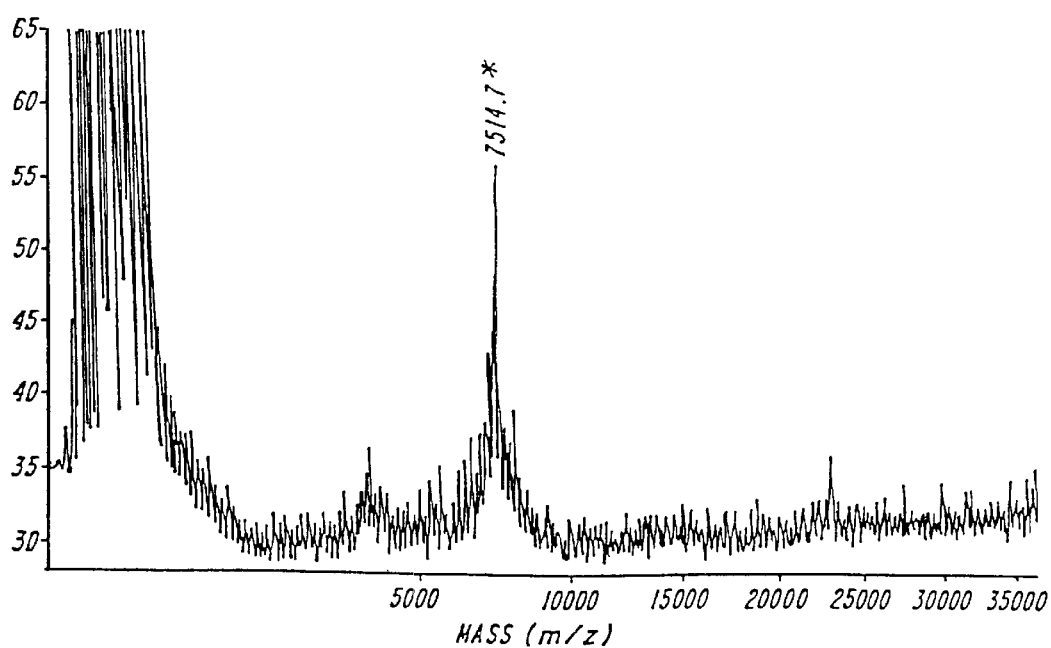
FIG. 33B shows a spectrum of two pooled negative LCRs (without template). The signal at 7514 Da represents oligo A (calculated: 7521 Da).

FIGS. 33A–B show spectra obtained from two pooled positive (33A) and negative (33B) LCRs, respectively. The positive reaction was performed with a chemically synthesized, single strand 50-mer as template with a sequence equivalent to the ligation product of oligo C and D. Oligo C was 5'-biotinylated. Therefore the template was not detected. As expected, only the ligation product of Oligo A and B (calculated mass 15450 Da) could be desorbed from the immobilized and ligated oligo C and D. This newly generated DNA fragment is represented by the mass signal of 15448 Da in FIG. 33A. Compared to FIG. 31A, this spectrum clearly shows that this method of sample preparation produces signals with improved resolution and intensity.

EXAMPLE 7

Mutation Detection by Solid Phase Oligo Base Extension of a Primer and Analysis by MALDI-TOF Mass Spectrometry Summary The solid-phase oligo base extension method detects point mutations and small deletions as well as small insertions in amplified DNA. The method is based on the extension of a detection primer that anneals adjacent to a variable nucleotide position on an affinity-captured amplified template, using a DNA polymerase, a mixture of three dNTPs, and the missing one dideoxy nucleotide. The resulting products are evaluated and resolved by MALDI-TOF mass spectrometry without further labeling procedures. The aim of the following experiment was to determine mutant and wildtype alleles in a fast and reliable manner.

Description of the Experiment

The method used a single detection primer followed by an oligonucleotide extension step to give products, differing in length by some bases specific for mutant or wildtype alleles which can be easily resolved by MALDI-TOF mass spectrometry. The method is described by using as example the exon 10 of the CFTR-gene. Exon 10 of this gene leads, in the homozygous state, to the clinical phenotype of cystic fibrosis.

Materials and Methods

Genomic DNA

Genomic DNA were obtained from healthy individuals, individuals homozygous or heterozygous for the ΔF508 mutation, and one individual heterozygous for the 1506S mutation. The wildtype and mutant alleles were confirmed by standard Sanger sequencing.

PCR amplification of Exon 10 of the CFTR Gene

The primers for PCR amplification were CFEx10-F (5-GCAAGTGAATCCTGAGCGTG-3' (SEQ.ID.No. 13) located in intron 9 and biotinylated) and CFEx 10-R (5'-GTGTGAAGGGCGTG-3', (SEQ.ID.No. 14) located in intron 10). Primers were used at a concentration of 8 pmol. Taq-polymerase including 10× buffer was purchased from Boehringer-Mannheim and dTNPs were obtained from Pharmacia. The total reaction volume was 50 μl. Cycling conditions for PCR were initially 5 min. at 95° C., followed by 1 min. at 94° C., 45 sec at 53° C., and 30 sec at 72° C. for 40 cycles with a final extension time of 5 min at 72° C.

Purification of the PCR Products

Amplification products were purified by using Qiagen's PCR purification kit (No. 28106) according to manufacturer's instructions. The elution of the purified products from the column was done in 50 μl TE-buffer (10 mM Tris, 1 mM EDTA, pH 7.5).

Affinity-capture and Denaturation of the Double Stranded DNA

10 μl aliquots of the purified PCR product were transferred to one well of a streptavidin-coated microtiter plate (No. 1645684 Boehringer-Mannheim or No. 95029262 Labsystems). Subsequently, 10 μl incubation buffer (80 mM sodium phosphate, 400 mM NaCl, 0.4% Tween 20, pH 7.5) and 30 μl water were added. After incubation for 1 hour at room temperature the wells were washed three times with 200 μl washing buffer (40 mM Tris, 1 mM EDTA, 50 mM NaCl, 0.1% Tween 20, pH 8.8). To denaturate the double stranded DNA, the wells were treated with 100 μl of a 50 mM NaOH solution for 3 min. Hence, the wells were washed three times with 200 μl washing buffer.

Oligo Base Extension Reaction

The annealing of 25 pmol detection primer (CF508: 5'CTATATTCATCATAGGAAACACCA-3' (SEQ ID No. 15)) was performed in 50 μl annealing buffer (20 mM Tris, 10 mM KCl, 10 mM $(NH_4)_2SO_4$, 2 mM MgSO, 1% Triton X-100, pH 8.75) at 50° C. for 10 min. The wells were washed three times with 200 μl washing buffer and once in 200 μl TE buffer. The extension reaction was performed by using some components of the DNA sequencing kit from USB (No. 70770) and dNTPs or ddNTPs from Pharmacia. The total reaction volume was 45 μl, consisting of 21 μl sample, 6 μl Sequenase-buffer, 3 μl 10 mM DTT solution, 4.5 μl of 0.5 mM of three dNTPs, 4.5 μl of 2 mM of the missing one ddNTP, 5.5 μl glycerol enzyme dilution buffer, 0.25 μl Sequenase 2.0, and 0.25 μl pyrophosphatase. The reaction was pipetted on ice and then incubated for 15 min. at room temperature and for 5 min. at 37° C. Hence, the wells were washed three times with 200 μl washing buffer and once with 60 μl of a 70 mM $NH_4$-citrate solution.

Denaturation and Precipitation of the Extended Primer

The extended primer was denatured in 50 μl 10% DMSO (dimethylsulfoxide) in water at 80° C. for 10 min. For precipitation, 10 μl $NH_4$-acetate (pH 6.5), 0.5 μl glycogen (10 mg/ml water, Sigma No. G1765), and 100 μl absolute ethanol were added to the supernatant and incubated for 1 hour at room temperature. After centrifugation at 13,000 g for 10 min., the pellet was washed in 70% ethanol and resuspended in 1 μl 18 Mohm/cm $H_2O$ water.

Sample Preparation and Analysis on MALDI-TOF Mass Spectrometry

Sample preparation was performed by mixing 0.3 μl each of matrix solution (0.7 M 3-hydroxypicolinic acid, 0.07 M dibasic ammonium citrate in 1:1 $H_2O:CH_3CN$) and of resuspended DNA/glycogen pellet on a sample target and allowed to air dry. Up to 20 samples were spotted on a probe target disk for introduction into the source region of an unmodified Thermo Bioanalysis (formerly Finnigan) Visions 2000 MALDI-TOF operated in reflectron mode with 5 and 20 kV on the target and conversion dynode, respectively. Theoretical average molecular mass ($M_r$(calc)) were calculated from atomic compositions; reported experimental Mr ($M_r$(exp)) values are those of the singly-protonated form, determined using external calibration.

Results

The aim of the experiment was to develop a fast and reliable method independent of exact stringencies for mutation detection that leads to high quality and high throughput in the diagnosis of genetic diseases. Therefore a special kind of DNA sequencing (oligo base extension of one mutation detection primer) was combined with the evaluation of the resulting mini-sequencing products by matrix-assisted laser desorption ionization (MALDI) mass spectrometry (MS). The time-of-flight (TOF) reflectron arrangement was chosen as a possible mass measurement system. To prove this hypothesis, the examination was performed with exon 10 of the CFTR-gene, in which some mutations could lead to the clinical phenotype of cystic fibrosis, the most common monogenetic disease in the Caucasian population.

The schematic presentations given in FIGS. 34A–B show the expected short sequencing products with the theoretically calculated molecular mass of the wildtype and various mutations of exon 10 of the CFTR-gene. The short sequencing products were produced using either ddTTP (FIG. 34A) or ddCTP (FIG. 34B) to introduce a definitive sequence related stop in the nascent DNA strand. The MALDI-TOF-MS spectra of healthy, mutation heterozygous, and mutation homozygous individuals are presented in FIGS. 35A–B. All samples were confirmed by standard Sanger sequencing which showed no discrepancy in comparison to the mass spec analysis. The accuracy of the experimental measurements of the various molecular masses was within a range of minus 21.8 and plus 87.1 dalton (Da) to the range expected. This is a definitive interpretation of the results allowed in each case. A further advantage of this procedure is the unambiguous detection of the ΔI507 mutation. In the ddTTP reaction, the wildtype allele would be detected, whereas in the ddCTP reaction the three base pair deletion would be disclosed.

The method described is highly suitable for the detection of single point mutations or microlesions of DNA. Careful choice of the mutation detection primers will open the window of multiplexing and lead to a high throughput including high quality in genetic diagnosis without any need for exact stringencies necessary in comparable allele-specific procedures. Because of the uniqueness of the genetic information, the oligo base extension of mutation detection primer is applicable in each disease gene or polymorphic region in the genome like variable number of tandem repeats (VNTR) or other single nucleotide polymorphisms (e.g., apolipoprotein E gene).

EXAMPLE 8

Detection of Polymerase Chain Reaction Products Containing 7-Deazapurine Moieties with Matrix-Assisted Laser Desorption/Ionization Time-of-Flight (MALDI-TOF) Mass Spectrometry Materials and Methods PCR Amplifications The following oligodeoxynucleotide primers were either synthesized according to standard phosphoamidite chemistry (Sinha, N. D. et al., *Tetrahdron Let.* 24: 5843–5846 (1983); Sinha, N. D. et al., *Nucleic Acids Res.* 12: 4539–4557 (1984)) on a Milligen 7500 DNA synthesizer (Millipore, Bedford, Mass., USA) in 200 nmol scales or purchased from MWG-Biotech (Ebersberg, Germany, primer 3) and Biometra (Goettingen, Germany, primers 6–7).

```
primer 1:  5'-GTCACCCTCGACCTGCAG-3'       (SEQ.ID.No. 16);

primer 2:  5'-TTGTAAAACGACGGCCAGT-3'      (SEQ.ID.No. 17);

primer 3:  5'-CTTCCACCGCGATGTTGA-3'       (SEQ.ID.No. 18);

primer 4:  5'-CAGGAAACAGCTATGAC-3'        (SEQ.ID.No. 19);

primer 5:  5'-GTAAAACGACGGCCAGT-3'        (SEQ.ID.No. 20);
```

```
primer 6: 5'-GTCACCCTCGACCTGCAgC-3'  (g: RiboG)  (SEQ.ID.No. 21);

primer 7: 5'-GTTGTAAAACGAGGGCCAgT-3'  (g: RiboG)  (SEQ.ID.No. 22).
```

The 99-mer and 200-mer DNA strands (modified and unmodified) as well as the ribo- and 7-deaza-modified 100-mer were amplified from pRFc1 DNA (10 ng, generously supplied S. Feyerabend, University of Hamburg) in 100 µl reaction volume containing 10 mmol/L KCl, 10 mmol/L $(NH_4)_2SO_4$, 20 mmol/L Tris HCl (pH=8.8), 2 mmol/L $MgSO_4$, (exo(−)Pseudococcus furiosus (Pfu)-Buffer, Pharmacia, Freiburg, Germany), 0.2 mmol/L each dNTP (Pharmacia, Freiburg, Germany), 1 µl of each primer and 1 unit of exo(−)Pfu DNA polymerase (Stratagene, Heidelberg, Germany).

For the 99-mer primers 1 and 2, for the 200-mer primers 1 and 3 and for the 100-mer primers 6 and 7 were used. To obtain 7-deazapurine modified nucleic acids, during PCR-amplification dATP and dGTP were replaced with 7-deaza-dATP and 7-deaza-dGTP. The reaction was performed in a thermal cycler (OmniGene, MWG-Biotech, Ebersberg, Germany) using the cycle: denaturation at 95° C. for 1 min., annealing at 51° C. for 1 min. and extension at 72° C. for 1 min. For all PCRs the number of reaction cycles was 30. The reaction was allowed to extend for additional 10 min. at 72° C. after the last cycle.

The 103-mer DNA strands (modified and unmodified) were amplified from M13mp 18 RFI DNA (100 ng, Pharmacia, Freiburg, Germany) in 100 µl reaction volume using primers 4 and 5; all other concentrations were unchanged. The reaction was performed using the cycle: denaturation at 95° C. for 1 min., annealing at 40° C. for 1 min., and extension at 72° C. for 1 min. After 30 cycles for the unmodified and 40 cycles for the modified 103-mer respectively, the samples were incubated for an additional 10 min. at 72° C.

Synthesis of 5'-[$^{32}$P]-labeled PCR-primers

Primers 1 and 4 were 5'-[$^{32}$P]-labeled employing T4-polynucleotide kinase (Epicentre Technologies) and(γ-$^{32}$P)-ATP. (BLU/NGG/502A, Dupont, Germany) according to the protocols of the manufacturer. The reactions were performed substituting 10% of primer 1 and 4 in PCR with the labeled primers under otherwise unchanged reaction conditions. The amplified DNAs were separated by gel electrophoresis on a 10% polyacrylamide. gel. The appropriate bands were excised and counted on a Packard TRI-CARB 460C liquid scintillation system (Packard, Conn., USA).

Primer-cleavage from Ribo-modified PCR-product

The amplified DNA was purified using Ultrafree-MC filter units (30,000 NMWL), it was then redissolved in 100 µl of 0.2 mol/L NaOH and heated at 95° C. for 25 minutes. The solution was then acidified with HCl (1 mol/L) and further purified for MALDI-TOF analysis employing Ultrafree-MC filter units (30,000 NMWL) as described below.

Purification of PCR Products

All samples were purified and concentrated using Ultrafree-MC units 30,000 NMWL (Millipore, Eschborn, Germany) according to the manufacturer's description. After lyophilization, PCR products were redissolved in 5 µl (3 µl for the 200-mer) of ultrapure water. This analyte solution was directly used for MALDI-TOF measurements.

MALDI-TOF MS

Aliquots of 0.5 µl of analyte solution and 0.5 µl of matrix solution (0.7 mol/L 3-HPA and 0.07 mol/L ammonium citrate in acetonitrile/water (1:1, v/v) were mixed on a flat metallic sample support. After drying at ambient temperature the sample was introduced into the mass spectrometer for analysis. The MALDI-TOF mass spectrometer used was a Finnigan MAT Vision 2000 (Finnigan MAT, Bremen, Germany). Spectra were recorded in the positive ion reflectron mode with a 5 keV ion source and 20 keV postacceleration. The instrument was equipped with a nitrogen laser (337 nm wavelength). The vacuum of the system was $3-4 \cdot 10^{-8}$ hPa in the analyzer region and $1-4 \cdot 10^{-7}$ hPa in the source region. Spectra of modified and unmodified DNA samples were obtained with the same relative laser power; external calibration was performed with a mixture of synthetic oligodeoxynucleotides (7- to 50-mer).

Results and Discussion

Enzymatic Synthesis of 7-deazapurine-nucleotide-Containing Nucleic Acids by PCR

Figure 36:
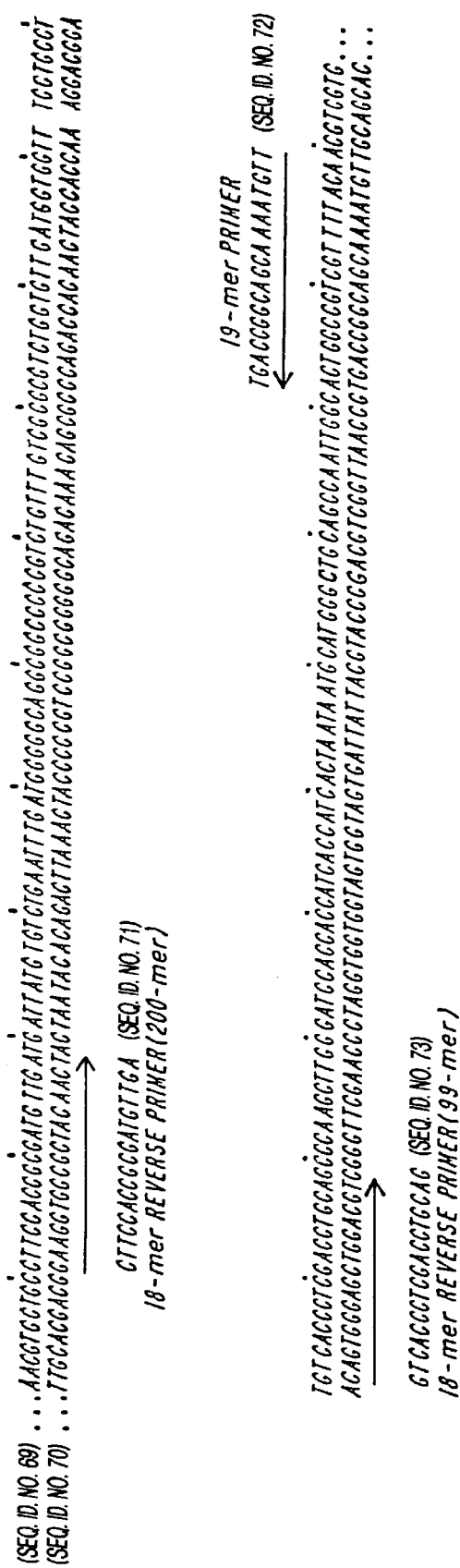
FIG. 36 shows the portion of the sequence of pRFc1 DNA, which was used as template for PCR amplification of unmodified and 7-deazapurine containing 99-mer and 200-mer nucleic acids as well as the sequences of the 19-mer primers and the two 18-mer reverse primers.
Figure 37:
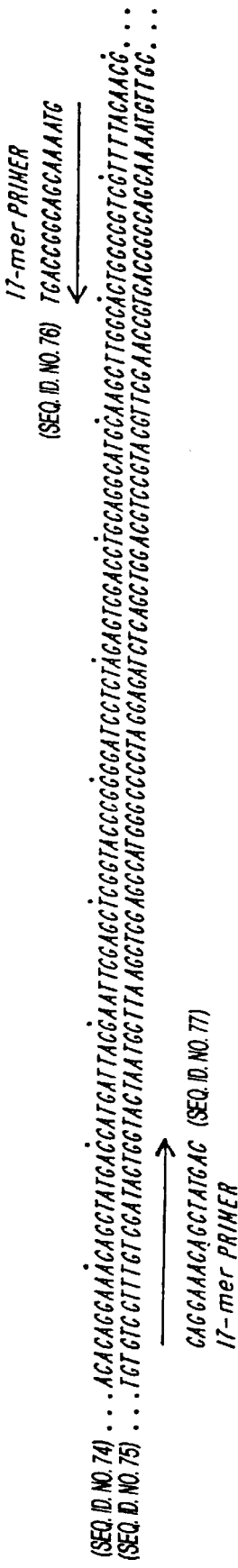
FIG. 37 shows the portion of the nucleotide sequence of M13mp18 RFI DNA, which was used for PCR amplification of unmodified and 7-deazapurine containing 103-mer nucleic acids. Also shown are nucleotide sequences of the 17-mer primers used in the PCR.

In order to demonstrate the feasibility of MALDI-TOF MS for the rapid, gel-free analysis of short PCR products and to investigate the effect of 7-deazapurine modification of nucleic acids under MALDI-TOF conditions, two different primer-template systems were used to synthesize DNA fragments. Sequences are displayed in FIGS. 36 and 37. While the two single strands of the 103-mer PCR product had nearly equal masses (▼M=8 u), the two single strands of the 99-mer differed by 526 u.

Considering that 7-deaza purine nucleotide building blocks for chemical DNA synthesis are approximately 160 times more expensive than regular ones (Product Information, Glen Research Corporation, Sterling, Va.) and their application in standard β-cyano-phosphoamidite chemistry is not trivial (Product Information, Glen Research Corporation, Sterling, Va.; Schneider, K. and B. T. Chait, Nucleic Acids Res. 23: 1570 (1995)) the cost of 7-deazapurine-modified primers would be very high. Therefore, to increase the applicability and scope of the method, all PCRs were performed using unmodified oligonucleotide primers which are routinely available. Substituting dATP and dGTP by $c^7$-dATP and $c^7$-dGTP in polymerase chain reaction led to products containing approximately 80% 7-deaza-purine-modified nucleosides for the 99-mer and 103-mer; and about 90% for the 200-mer, respectively. Table I shows the base composition of all PCR products.

TABLE I

Base composition of the 99-mer, 103-mer and 200-mer PCR amplification products (unmodified and 7-deaza purine modified)

| DNA-fragments[1] | C | T | A | G | c[7]-deaza-A | c[7]-deaza-6 | rel. mod.[2] |
|---|---|---|---|---|---|---|---|
| 200-mer s | 54 | 34 | 56 | 56 | — | — | — |
| modified 200-mer s | 54 | 34 | 6 | 5 | 50 | 51 | 90% |
| 200-mer a | 56 | 56 | 34 | 54 | — | — | — |
| modified 200-mer a | 56 | 56 | 3 | 4 | 31 | 50 | 92% |
| 103-mer s | 28 | 23 | 24 | 28 | — | — | — |
| modified 103-mer s | 28 | 23 | 6 | 5 | 18 | 23 | 79% |
| 103-mer a | 28 | 24 | 23 | 28 | — | — | — |
| modified 103-mer a | 28 | 24 | 7 | 4 | 16 | 24 | 78% |
| 99-mer s | 34 | 21 | 24 | 20 | — | — | — |
| modified 99-mer s | 34 | 21 | 6 | 5 | 18 | 15 | 75% |
| 99-mer a | 20 | 24 | 21 | 34 | — | — | — |
| modified 99-mer a | 20 | 24 | 3 | 4 | 18 | 30 | 87% |

[1]"s" and "a" describe "sense" and "antisense" strands of the double-stranded amplified product.
[2]indicates relative modification as percentage of 7-deaza-purine-modified nucleotides of total amount of purine nucleotides.

Figure 38:
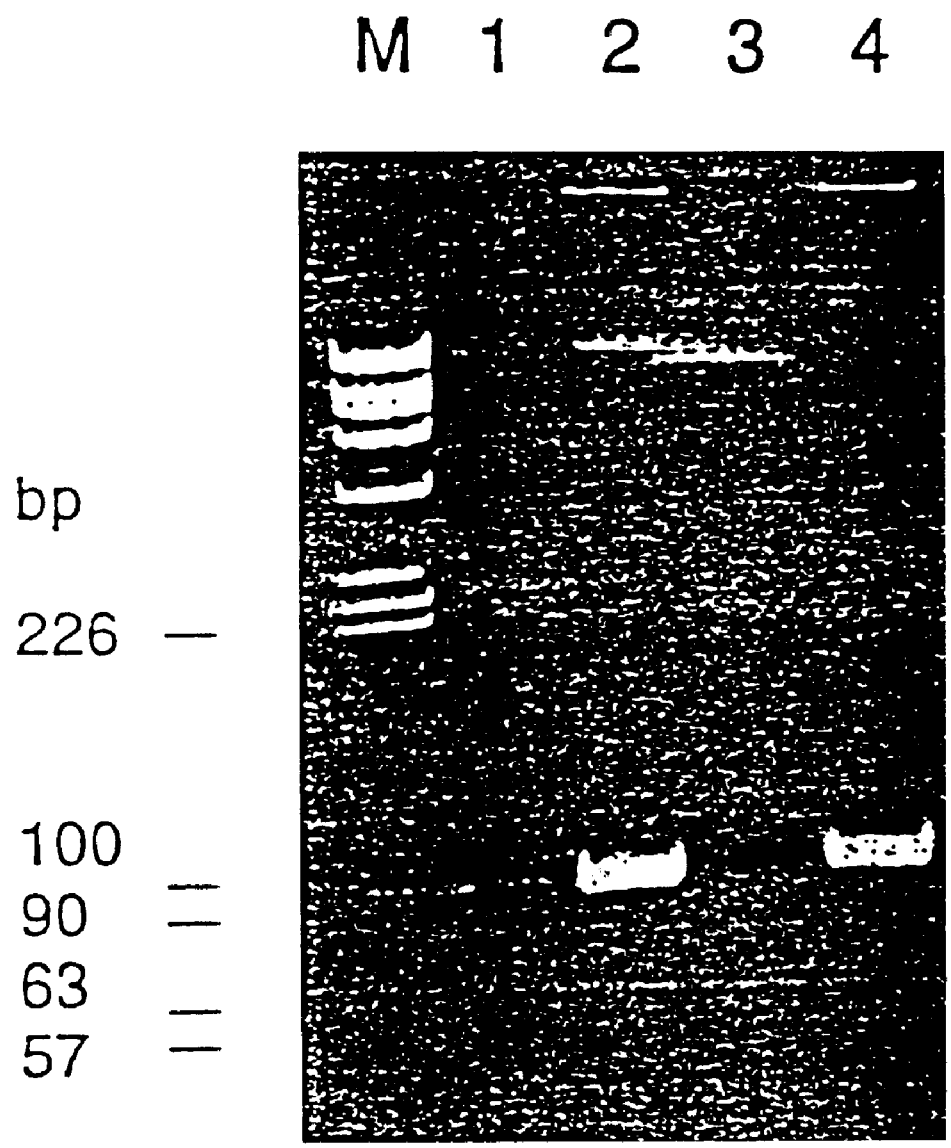
FIG. 38 shows the result of a polyacrylamide gel electrophoresis of PCR products purified and concentrated for MALDI-TOF MS analysis. M: chain length marker, lane 1:7-deazapurine containing 99-mer PCR product, lane 2: unmodified 99-mer, lane 3:7-deazapurine containing 103-mer and lane 4: unmodified 103-mer PCR product.

However, it remained to be determined whether 80–90% 7-deaza-purine modification is sufficient for accurate mass spectrometer detection. It was therefore important to determine whether all purine nucleotides could be substituted during the enzymatic amplification step. This was not trivial since it had been shown that c[7]-dATP cannot fully replace dATP in PCR if Taq DNA polymerase is employed (Seela, F. and A. Roelling, *Nucleic Acids Res*. 20: 55–61 (1992)). Fortunately we found that exo(-)Pfu DNA polymerase indeed could accept c[7]-dATP and c[7]-dGTP in the absence of unmodified purine triphosphates. However, the incorporation was less efficient leading to a lower yield of PCR product (FIG. 38). Ethidium-bromide stains by intercalation with the stacked bases of the DNA-doublestrand. Therefore lower band intensities in the ethidium-bromide stained gel might be artifacts since the modified DNA-strands do not necessarily need to give the same band intensities as the unmodified ones.

Figure 39:
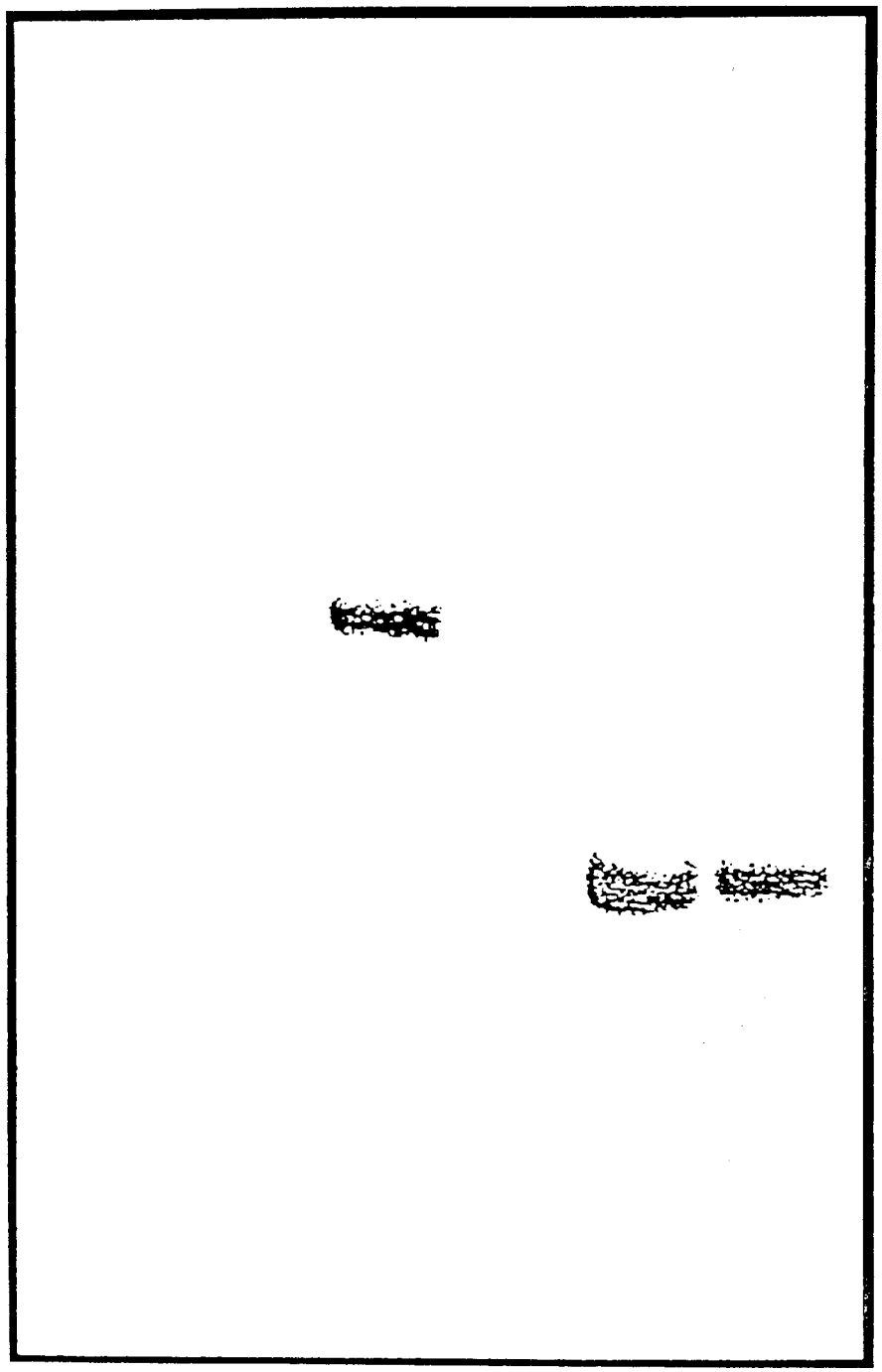
FIG. 39: an autoradiogram of polyacrylamide gel electrophoresis of PCR reactions carried out with 5',-[$^{32}$P]-labeled primers 1 and 4. Lanes 1 and 2: unmodified and 7-deazapurine modified 200-mer (71123 and 39582 counts), lanes 3 and 4: unmodified and 7-deazapurine modified 200-mer (71123 and 39582 counts) and lanes 5 and 6.

To verify these results, the PCRs with [32P]-labeled primers were repeated. The autoradiogram (FIG. 39) clearly shows lower yields for the modified PCR-products. The bands were excised from the gel and counted. For all PCR products the yield of the modified nucleic acids was about 50%, referring to the corresponding unmodified amplification product. Further experiments showed that exo(-)Deep Vent and Vent DNA polymerase were able to incorporate c[7]-dATP and c[7]-dGTP during PCR as well. The overall performance, however, turned out to be best for the exo(-) Pfu DNA polymerase giving the least side products during amplification. Using all three polymerases, if was found that such PCRs employing c[7]-dATP and c[7]-dGTP instead of their isosteres showed fewer side-reactions giving a cleaner PCR-product. Decreased occurrence of amplification side products may be explained by a reduction of primer mismatches due to a lower stability of the complex formed from the primer and the 7-deaza-purine-containing template which is synthesized during PCR. Decreased melting point for DNA duplexes containing 7-deaza-purine have been described (Mizusawa, S. et al., *Nucleic Acids Res*. 14: 1319–1324 (1986)). In addition to the three polymerases specified above (exo(-) Deep Vent DNA polymerase, Vent DNA polymerase and exo(-) (Pfu) DNA polymerase), it is anticipated that other polymerases, such as the Large Klenow fragment of *E.coli* DNA polymerase, Sequenase, Taq DNA polymerase and U AmpliTaq DNA polymerase can be used. In addition, where RNA is the template, RNA polymerases, such as the SP6 or the T7 RNA polymerase, must be used.

MALDI-TOF Mass Spectrometry of Modified and Unmodified PCR Products

The 99-mer, 103-mer and 200-mer PCR products were analyzed by MALDI-TOF MS. Based on past experience, it was known that the degree of depurination depends on the laser energy used for desorption and ionization of the analyte. Since the influence of 7-deazapurine modification on fragmentation due to depurination was to be investigated, all spectra were measured at the same relative laser energy.

FIGS. 40A and 40B show the mass spectra of the modified and unmodified 103-mer nucleic acids. In case of the modified 103-mer, fragmentation causes a broad (M+H)+ signal. The maximum of the peak is shifted to lower masses so that the assigned mass represents a mean value of the (M+H)+ signal and signals of fragmented ions, rather than the (M+H)+ signal itself. Although the modified 103-mer still contains about 20% A and G from the oligonucleotide primers, it shows less fragmentation which is featured by much more narrow and symmetric signals. Peak tailing, especially on the lower mass side due to depurination, is substantially reduced. Hence, the difference between measured and calculated mass is strongly reduced although it is still below the expected mass. For the unmodified sample, a (M+H)+ signal of 31670 was observed, which is a 97 u or 0.3% difference to the calculated mass, while in the case of the modified sample, this mass difference diminished to 10 u or 0.03% (31713 u found, 31723 u calculated). These observations are verified by a significant increase in mass resolution of the (M+H)+ signal of the two signal strands (m/$\Delta$m=67 as opposed to 18 for the unmodified sample with $\Delta$m=full width at half maximum, fwhm). Because of the low mass difference between the two single strands (8u), their individual signals were not resolved.

With the results of the 99 base pair DNA fragments, the effects of increased mass resolution for 7-deazapurine-containing DNA becomes even more evident. The two single strands in the unmodified sample were not resolved even though the mass difference between the two strands of the PCR product was very high with 526 u due to unequal distribution of purines and pyrimidines (FIG. 41A). In contrast to this, the modified DNA showed distinct peaks for the two single strands (FIG. 41B) which makes the superiority of this approach for the determination of molecular weights to gel electrophoretic methods even more profound. Although base line resolution was not obtained, the individual masses were able to be assigned with an accuracy of 0.1% (Δm=27 u for the lighter (calc. mass=30224 u) and Δm=14 u for the heavier strand (calc. mass=30750 u)). Again, it was found that the full width at half maximum was substantially decreased for the 7-deazapurine containing sample.

In case of the 99-mer and the 103-mer, the 7-deazapurine containing nucleic acids seem to give higher sensitivity despite the fact that they still contain about 20% unmodified purine nucleotides. To get comparable signal-to-noise ratio at similar intensities for the $(M+H)^+$ signals, the unmodified 99-mer required 20 laser shots in contrast to 12 for the modified one and the 103-mer required 12 shots for the unmodified sample as opposed to three for the 7-deazapurine nucleoside-containing PCR product.

Comparing the spectra of the modified and unmodified 200-mer amplicons, improved mass resolution was again found for the 7-deaza-purine-containing sample as well as increased signal intensities (FIGS. 42A and 42B). While the signal of the single strands predominates in the spectrum of the modified sample the DNA-duplex and dimers of the single strands gave the strongest signal for the unmodified sample.

A complete 7-deaza purine modification of nucleic acids may be achieved either using modified primers in PCR or cleaving the unmodified primers from the partially modified PCR product. Since disadvantages are associated with modified primers, as described above, a 100-mer was synthesized using primers with a ribo-modification. The primers were cleaved hydrolytically with NaOH according to a method developed earlier in our laboratory (Köster et al., *Z. Physiol. Chem.* 359: 1579–1589 (1978)). Both hydrolyzed PCR product as well as the two released primers could be detected, together with a small signal from residual uncleaved 100-mer. This procedure is especially useful for the MALDI-TOF analysis of very short PCR-products since the share of unmodified purines originating from the primer increases with decreasing length of the amplified sequence.

The remarkable properties of 7-deazapurine modified nucleic acids can be explained by either more effective desorption and/or ionization, increased ion stability and/or a lower denaturation energy of the double stranded purine-modified nucleic acid. The exchange of the N-7 for a methine group results in the loss of one acceptor for a hydrogen bond which influences the ability of the nucleic acid to form secondary structures due to non-Watson-Crick base pairing (Seela, F. and A. Kehne, *Biochemistry* 26: 2232–2238 (1987)), which should be a reason for better desorption during the MALDI process. In addition to this, the aromatic system of 7-deazapurine has a lower electron density that weakens Watson-Crick base pairing resulting in a decreased melting point (Mizusawa, S. et al., *Nucleic Acids Res.* 14: 1319–1324 (1986)) of the double-strand. This effect may decrease the energy needed for denaturation of the duplex in the MALDI process. These aspects as well as the loss of a site which probably will carry a positive charge on the N-7 nitrogen renders the 7-deazapurine-modified nucleic acid less polar and may promote the effectiveness of desorption.

Because of the absence of N-7 as proton acceptor and the decreased polarization of the C-N bond in 7-deazapurine nucleosides, depurination following the mechanisms established for hydrolysis in solution is prevented. Although a direct correlation of reactions in solution and in the gas phase is problematic, less fragmentation due to depurination of the modified nucleic acids can be expected in the MALDI process. Depurination may either be accompanied by loss of charge, which decreases the total yield of charged species, or it may produce charged fragmentation products, which decreases the intensity of the non-fragmented molecular ion signal.

The observation of both increased sensitivity and decreased peak tailing of the $(M+H)^+$ signals on the lower mass side due to decreased fragmentation of the 7-deazapurine-containing samples indicate that the N-7 atom indeed is essential for the mechanism of depurination in the MALDI-TOF process. In conclusion, 7-deazapurine-containing nucleic acids show distinctly increased ion-stability and sensitivity under MALDI-TOF conditions and therefore provide for higher mass accuracy and mass resolution.

EXAMPLE 9

Solid State Sequencing and Mass Spectrometer Detection

Materials and Methods

Oligonucleotides were purchased from Operon Technologies (Alameda, Calif.) in an unpurified form. Sequencing reactions were performed on a solid surface using reagents from the sequencing kit for Sequenase Version 2.0 (Amersham, Arlington Heights, Ill.).

Sequencing a 39-mer Target

Sequencing complex:

5'-TCTGGCCTGGTGCAGGGCCTATTGTAGTTGTGA CGTACA-$(A^b)_a$-3' (DNA11683) (SEQ.ID.No. 23)

3'-TCAACACTGCATGT-5' (PNA16/DNA) (SEQ.ID.No. 24)

In order to perform solid-state DNA sequencing, template strand DNA11683 was 3'-biotinylated by terminal deoxynucleotidyl transferase. A 30 μl reaction, containing 60 pmol of DNA11683, 1.3 nmol of biotin 14-dATP (GIBCO BRL, Grand Island, N.Y.), 30 units of terminal transferase (Amersham, Arlington Heights, Ill.), and 1× reaction buffer (supplied with enzyme), was incubated at 3° C. for 1 hour. The reaction was stopped by heat inactivation of the terminal transferase at 70° C. for 10 min. The resulting product was desalted by passing through a TE-10 spin column (Clontech). More than one molecule of biotin-14-dATP could be added to the 3'-end of DNA11683. The biotinylated DNA11683 was incubated with 0.3 mg of Dynal streptavidin beads in 30 μl 1× binding and washing buffer at ambient temperature for 30 min. The beads were washed twice with TE, resuspended in 30 μl TE, and a 10 μl aliquot (containing 0.1 mg of beads) was used for sequencing reactions.

The 0.1 mg beads from previous step were resuspended in a 10 μl volume containing 2 μl of 5× Sequenase buffer (200 mM Tris-HCl, pH 7.5, 100 mM $MgCl_2$, and 250 mM NaCl) from the Sequenase kit and 5 pmol of corresponding primer PNA16/DNA. The annealing mixture was heated to 70° C. and allowed to cool slowly to room temperature over a 20–30 min. time period. Then 1 μl 0.1 M dithiothreitol solution, 1 μl Mn buffer (0.15 M sodium isocitrate and 0.1 M $MnCl_2$), and 2 μl of diluted Sequenase (3.25 units) were added. The reaction mixture was divided into four aliquots of 3 μl each and mixed with termination mixes (each consists of 3 μl of the appropriate termination mix: 32 μM c7dATP, 32 μM dCTP, 32 μM c7dGTP, 32 μM dTTP and 3.2 μM of one of the four ddTNPS, in 50 mM NaCl). The reaction mixtures were incubated at 37° C. for 2 min. After the completion of extension, the beads were precipitated and the supernatant was removed. The beads were washed twice and resuspended in TE and kept at 4° C.

Sequencing a 78-mer Target
  Sequencing complex:
  5'-AAGATCTGACCAGGGATTCGGTTAGCGTGACT
    GCTGCTGCTGCTGCTGCTGCTGGATGATCCGA
    CGCATCAGATCTGG-($A^b$)$_n$-3' (SEQ.ID.No. 25)
    (TNR.PLASM2)
  3'-CTACTAGGCTGCGTAGTC-5'(CM1)(SEQ.ID.No. 26)
  The target TNR.PLASM2 was biotinylated and sequenced using procedures similar to those described in previous section (sequencing a 39-mer target).
Sequencing a 15-mer Target With Partially-duplex Probe
  Sequencing complex:
  5'-F-GATGATCCGACGCATCACAGCTC-3' (SEQ.ID.No. 27)
  3'-b-CTACTAGGCTGCGTAGTGTCGAGAACCTTGGCT-5' (SEQ.ID.No. 28)

CM1B3B was immobilized on DynaBeads M280 with streptavidin (Dynal, Norway) by incubating 60 pmol of CM1B3B with 0.3 magnetic beads in 30 µl 1M NaCl and TE (1× binding and washing buffer) at room temperature for 30 min. The beads were washed twice with TE, resuspended in 30 µl TE, and a 10 or 20 µl aliquot (containing 0.1 or 0.2 mg of beads respectively) was used for sequencing reactions.

The duplex was formed by annealing a corresponding aliquot of beads from previous step with 10 pmol of DF11a5F (or 20 pmol of DF11a5F for 0.2 mg of beads) in a 9 µl volume containing 2 µl of 5× Sequenase buffer (200 mM Tris-HCl, pH 7.5, 100 mM MgCl$_2$, and 250 mM NaCl) from the Sequenase kit. The annealing mixture was heated to 65° C. and allowed to cool slowly to 37° C. over a 20–30 min time period. The duplex primer was then mixed with 10 pmol of TS10 (20 pmol of TS10 for 0.2 mg of beads) in 1 µl volume, and the resulting mixture was further incubated at 37° C. for 5 min., and room temperature for 5–10 min. Then 1 µl 0.1 M dithiothreitol solution, 1 µ; Mn buffer (0.15 M sodium isocitrate and 0.1 M MnCl$_2$), and 2 µl of diluted Sequenase (3.25 units) were added. The reaction mixture was divided into four aliquots of 3 µl each and mixed with termination mixes (each consists of 4 µl of the appropriate termination mix: 16 µM dATP, 16 µM dCTP, 16 µM dGTP, 16 µM dTTP and 1.6 µM of one of the four ddNTPs, in 50 mM NaCl). The reaction mixtures were incubated at room temperature for 5 min., and 37° C. for 5 min. After the completion of extension, the beads were precipitated and the supernatant was removed. The beads were resuspended in 20 µl TE and kept at 4° C. An aliquot of 2 µl (out of 20 µl) from each tube was taken and mixed with 8 µl of formamide, the resulting samples were denatured at 90–95° C. for 5 min.

and 2 µl (out of 10 µl total) was applied to an ALF DNA sequencer (Pharmacia, Piscataway, N.J.) using a 10% polyacrylamide gel containing 7 M urea and 0.6× TBE. The remaining aliquot was used for MALDI-TOF MS analysis.
MALDI Sample Preparation and Instrumentation Before MALDI analysis, the sequencing-ladder-loaded magnetic beads were washed twice using 50 mM ammonium citrate and resuspended in 0.5 µl pure water. The suspension was then loaded onto the sample target of the mass spectrometer and 0.5 µl of saturated matrix solution (3-hydropicolinic acid (HPA): ammonium citrate=10:1 mole ratio in 50% acetonitrile) was added. The mixture was allowed to dry prior to mass spectrometer analysis.

The reflectron TOFMS mass spectrometer (Vision 2000, Finnigan MAT, Bremen, Germany) was used for analysis. 5 kV was applied in the ion source and 20 kV was applied for postaccelaration. All spectra were taken in the positive ion mode and a nitrogen laser was used. Normally, each spectrum was averaged for more than 100 shots and a standard 25-point smoothing was applied.

Results and Discussion
Conventional Solid-state Sequencing

In conventional sequencing methods, a primer is directly annealed to the template and then extended and terminated in a Sanger dideoxy sequencing. Normally, a biotinylated primer is used and the sequencing ladders are captured by streptavidin-coated magnetic beads. After washing, the products are eluted from the beads using EDTA and formamide. However, our previous findings indicated that only the annealed strand of a duplex is desorbed and the immobilized strand remains on the beads. Therefore, it is advantageous to immobilize the template and anneal the primer. After the sequencing reaction and washing, the beads with the immobilized template and annealed sequencing ladder can be loaded directly onto the mass spectrometer target and mixed with matrix. In MALDI, only the annealed sequencing ladder will be desorbed and ionized, and the immobilized template will remain on the target.

A 39-mer template (SEQ.ID.No. 23) was first biotinylated at the 3' end by adding biotin-14-dATP with terminal transferase. More than one biotin-14-dATP molecule could be added by the enzyme. However, since the template was immobilized and remained on the beads during MALDI, the number of biotin-14-dATP added would not affect the mass spectra. A 14-mer primer (SEQ.ID.No. 29) was used for the solid-state sequencing. MALDI-TOF mass spectra of the four sequencing ladders are shown in FIGS. 44A–D and the expected theoretical values are shown in Table II.

TABLE II

| | |
|---|---|
| 1 | 5'-TCTGGCCTGGTGCAGGGCCTATTGTAGTTGTGACGTACA-($A^B$)$_n$-3' |
| 2 | 3'-TCAACACTGCATGT-5- |
| 3 | 3'-ATCAACACTGCATGT-5' |
| 4 | 3'-CATCAACACTGCATGT-5' |
| 5 | 3'-ACATCAACACTGCATGT-5' |
| 6 | 3'-AACATCAACACTGCATGT-5' |
| 7 | 3'-TAACATCAACACTGCATGT-5' |
| 8 | 3'-ATAACATCAACACTGCATGT-5' |
| 9 | 3'-GATAACATCAACACTGCATGT-5' |
| 10 | 3'-GGATAACATCAACACTGCATGT-5' |
| 11 | 3'-CGGATAACATCAACACTGCATGT-5' |
| 12 | 3'-CCGGATAACATCAACACTGCATGT-5' |
| 13 | 3'-CCCGGATAACATCAACACTGCATGT-5' |
| 14 | 3'-TCCCGGATAACATCAACACTGCATGT-5' |
| 15 | 3'-GTCCCGGATAACATCAACACTGCATGT-5' |
| 16 | 3'-CGTCCCGGATAACATCAACACTGCATGT-5' |
| 17 | 3'-ACGTCCCGGATAACATCAACACTGCATGT-5' |

TABLE II-continued

| | |
|---|---|
| 18 | 3'-CACGTCCCGGATAACATCAACACTGCATGT-5' |
| 19 | 3'-CCACGTCCCGGATAACATCAACACTGCATGT-5' |
| 20 | 3'-ACCACGTCCCGGATAACATCAACACTGCATGT-5' |
| 21 | 3'-GACCACGTCCCGGATAACATCAACACTGCATGT-5' |
| 22 | 3'-GGACCACGTCCCGGATAACATCAACACTGCATGT-5' |
| 23 | 3'-CGGACCACGTCCCGGATAACATCAACACTGCATGT-5' |
| 24 | 3'-CCGGACCACGTCCCGGATAACATCAACACTGCATGT-5' |
| 25 | 3'-ACCGGACCACGTCCCGGATAACATCAACACTGCATGT-5' |
| 26 | 3'-GACCGGACCACGTCCCGGATAACATCAACACTGCATGT-5' |
| 27 | 3'-AGACCGGACCACGTCCCGGATAACATCAACACTGCATGT-5' |

| | A-reaction | C-reaction | G-reaction | T-reaction |
|---|---|---|---|---|
| 1. | | | | |
| 2. | 4223.8 | 4223.8 | 4223.8 | 4223.8 |
| 3. | 4521.1 | | | |
| 4. | | 4810.2 | | |
| 5. | 5123.4 | | | |
| 6. | 5436.6 | | | |
| 7. | | | | 5740.8 |
| 8. | 6054.0 | | | |
| 9. | | | 6383.2 | |
| 10. | | | 6712.4 | |
| 11. | | 7001.6 | | |
| 12. | | 7290.8 | | |
| 13. | | 7580.0 | | |
| 14. | | | | 7884.2 |
| 15. | | | 8213.4 | |
| 16. | | 8502.6 | | |
| 17. | 8815.8 | | | |
| 18. | | 9105.0 | | |
| 19. | | 9394.2 | | |
| 20. | 9707.4 | | | |
| 21. | | | 10036.6 | |
| 22. | | | 10365.8 | |
| 23. | | 10655.0 | | |
| 24. | | 10944.2 | | |
| 25. | 11257.4 | | | |
| 26. | | | 11586.6 | |
| 27. | 11899.8 | | | |

The sequencing reaction produced a relatively homogenous ladder, and the full-length sequence was determined easily. One peak around 5150 appeared in all reactions was not identified. A possible explanation: is that a small portion of the template formed some kind of secondary structure, such as a loop, which hindered Sequenase extension. Misincorporation is of minor importance, since the intensity of these peaks were much lower than that of the sequencing ladders. Although 7-deaza purines were used in the sequencing reaction, which could stabilize the N-glycosidic bond and prevent depurination, minor base losses were still observed since the primer was not substituted by 7-deazapurines. The full length ladder, with a ddA at the 3' end, appeared in the A reaction with an apparent mass of 11899.8. However, a more intense peak of 122 appeared in all four reactions and is likely due to an addition of an extra nucleotide by the Sequenase enzyme.

The same technique could be used to sequence longer DNA fragments. A 78-mer template containing a CTG repeat (SEQ.ID.No. 25) was 3'-biotinylated by adding biotin-14-dATP with terminal transferase. An 18-mer primer (SEQ.ID.No. 26) was annealed right outside the CTG repeat so that the repeat could be sequenced immediately after primer extension. The four reactions were washed and analyzed by MALDI-TOF MS as usual. An example of the G-reaction is shown in FIG. 45 and the expected sequencing ladder is shown in Table III with theoretical mass values for each ladder component. All sequencing peaks were well resolved except the last component (theoretical value 20577.4) was indistinguishable from the background. Two neighboring sequencing peaks (a 62-mer and a 63-mer) were also separated indicating that such sequencing analysis could be applicable to longer templates. Again, an addition of an extra nucleotide by the Sequenase enzyme was observed in this spectrum. This addition is not template specific and appeared in all four reactions which makes it easy to be identified. Compared to the primer peak, the sequencing peaks were at much lower intensity in the long template case. Further optimization of the sequencing reaction may be required.

TABLE III

AAGATCTGACCAGGGATTCGGTTAGCGTGACTGCTGCTGCTGCTGCTGGATGATCCGACGCATCAGATCTGG-$(A^B)_n$-3'

| | |
|---|---|
| 1 | 3'-CTACTAGGCTGCGTAGTC-5' |
| 2 | 3'-CCTACTAGGCTGCGTAGTC-5' |
| 3 | 3'-ACCTACTAGGCTGCGTAGTC-5' |
| 4 | 3'-GACCTACTAGGCTGCGTAGTC-5' |
| 5 | 3'-CGACCTACTAGGCTGCGTAGTC-5' |

TABLE III-continued

| | |
|---|---|
| 6 | 3'-ACGACCTACTAGGCTGCGTAGTC-5' |
| 7 | 3'-GACGACCTACTAGGCTGCGTAGTC-5' |
| 8 | 3'-CGACGACCTACTAGGCTGCGTAGTC-5' |
| 9 | 3'-ACGACGACCTACTAGGCTGCGTAGTC-5' |
| 10 | 3'-GACGACGACCTACTAGGCTGCGTAGTC-5' |
| 11 | 3'-CGACGACGACCTACTAGGCTGCGTAGTC-5' |
| 12 | 3'-ACGACGACGACCTACTAGGCTGCGTAGTC-5' |
| 13 | 3'-GACGACGACGACCTACTAGGCTGCGTAGTC-5' |
| 14 | 3'-CGACGACGACGACCTACTAGGCTGCGTAGTC-5' |
| 15 | 3'-ACGACGACGACGACCTACTAGGCTGCGTAGTC-5' |
| 16 | 3'-GACGACGACGACGACCTACTAGGCTGCGTAGTC-5' |
| 17 | 3'-CGACGACGACGACGACCTACTAGGCTGCGTAGTC-5' |
| 18 | 3'-ACGACGACGACGACGACCTACTAGGCTGCGTAGTC-5' |
| 19 | 3'-GACGACGACGACGACGACCTACTAGGCTGCGTAGTC-5' |
| 20 | 3'-CGACGACGACGACGACGACCTACTAGGCTGCGTAGTC-5' |
| 21 | 3'-ACGACGACGACGACGACGACCTACTAGGCTGCGTAGTC-5' |
| 22 | 3'-GACGACGACGACGACGACGACCTACTAGGCTGCGTAGTC-5' |
| 23 | 3'-CGACGACGACGACGACGACGACCTACTAGGCTGCGTAGTC-5' |
| 24 | 3'-ACGACGACGACGACGACGACGACCTACTAGGCTGCGTAGTC-5' |
| 25 | 3'-GACGACGACGACGACGACGACGACCTACTAGGCTGCGTAGTC-5' |
| 26 | 3'-TGACGACGACGACGACGACGACGACCTACTAGGCTGCGTAGTC-5' |
| 27 | 3'-CTGACGACGACGACGACGACGACGACCTACTAGGCTGCGTAGTC-5' |
| 28 | 3'-ACTGACGACGACGACGACGACGACGACCTACTAGGCTGCGTAGTC-5' |
| 29 | 3'-CACTGACGACGACGACGACGACGACGACCTACTAGGCTGCGTAGTC-5' |
| 30 | 3'-GCACTGACGACGACGACGACGACGACGACCTACTAGGCTGCGTAGTC-5' |
| 31 | 3'-CGCACTGACGACGACGACGACGACGACGACCTACTAGGCTGCGTAGTC-5' |
| 32 | 3'-TCGCACTGACGACGACGACGACGACGACGACCTACTAGGCTGCGTAGTC-5' |
| 33 | 3'-ATCGCACTGACGACGACGACGACGACGACGACCTACTAGGCTGCGTAGTC-5' |
| 34 | 3'-AATCGCACTGACGACGACGACGACGACGACGACCTACTAGGCTGCGTAGTC-5' |
| 35 | 3'-CAATCGCACTGACGACGACGACGACGACGACGACCTACTAGGCTGCGTAGTC-5' |
| 36 | 3'-CCAATCGCACTGACGACGACGACGACGACGACGACCTACTAGGCTGCGTAGTC-5' |
| 37 | 3'-GCCAATCGCACTGACGACGACGACGACGACGACGACCTACTAGGCTGCGTAGTC-5' |
| 38 | 3'-AGCCAATCGCACTGACGACGACGACGACGACGACGACCTACTAGGCTGCGTAGTC-5' |
| 39 | 3'-AAGCCAATCGCACTGACGACGACGACGACGACGACGACCTACTAGGCTGCGTAGTC-5' |
| 40 | 3'-TAAGCCAATCGCACTGACGACGACGACGACGACGACGACCTACTAGGCTGCGTAGTC-5' |
| 41 | 3'-CTAAGCCAATCGCACTGACGACGACGACGACGACGACGACCTACTAGGCTGCGTAGTC-5' |
| 42 | 3'-CCTAAGCCAATCGCACTGACGACGACGACGACGACGACGACCTACTAGGCTGCGTAGTC-5' |
| 43 | 3'-CCCTAAGCCAATCGCACTGACGACGACGACGACGACGACGACCTACTAGGCTGCGTAGTC-5' |
| 44 | 3'-TCCCTAAGCCAATCGCACTGACGACGACGACGACGACGACGACCTACTAGGCTGCGTAGTC-5' |
| 45 | 3'-GTCCCTAAGCCAATCGCACTGACGACGACGACGACGACGACGACCTACTAGGCTGCGTAGTC-5' |
| 46 | 3'-GGTCCCTAAGCCAATCGCACTGACGACGACGACGACGACGACGACCTACTAGGCTGCGTAGTC-5' |
| 47 | 3'-TGGTCCCTAAGCCAATCGCACTGACGACGACGACGACGACGACGACCTACTAGGCTGCGTAGTC-5' |
| 48 | 3'-CTGGTCCCTAAGCCAATCGCACTGACGACGACGACGACGACGACGACCTACTAGGCTGCGTAGTC-5' |
| 49 | 3'-ACTGGTCCCTAAGCCAATCGCACTGACGACGACGACGACGACGACGACCTACTAGGCTGCGTAGTC-5' |
| 50 | 3'-GACTGGTCCCTAAGCCAATCGCACTGACGACGACGACGACGACGACGACCTACTAGGCTGCGTAGTC-5' |
| 51 | 3'-AGACTGGTCCCTAAGCCAATCGCACTGACGACGACGACGACGACGACGACCTACTAGGCTGCGTAGTC-5' |
| 52 | 3'-TAGACTGGTCCCTAAGCCAATCGCACTGACGACGACGACGACGACGACGACCTACTAGGCTGCGTAGTC-5' |
| 53 | 3'-CTAGACTGGTCCCTAAGCCAATCGCACTGACGACGACGACGACGACGACGACCTACTAGGCTGCGTAGTC-5' |
| 54 | 3'-TCTAGACTGGTCCCTAAGCCAATCGCACTGACGACGACGACGACGACGACGACCTACTAGGCTGCGTAGTC-5' |
| 55 | 3'-TTCTAGACTGGTCCCTAAGCCAATCGCACTGACGACGACGACGACGACGACGACCTACTAGGCTGCGTAGTC-5' |

| | ddATP | ddCTP | ddGTP | ddTTP |
|---|---|---|---|---|
| 1. | 5491.6 | 5491.6 | 5491.6 | 5491.6 |
| 2. | | 5764.8 | | |
| 3. | 6078.0 | | | |
| 4. | | | 6407.2 | |
| 5. | | 6696.4 | | |
| 6. | 7009.6 | | | |
| 7. | | | 7338.8 | |
| 8. | | 7628.0 | | |
| 9. | 7941.2 | | | |
| 10. | | | 8270.4 | |
| 11. | | 8559.6 | | |
| 12. | 8872.8 | | | |
| 13. | | | 9202.0 | |
| 14. | | 9491.2 | | |
| 15. | 9804.4 | | | |
| 16. | | | 10133.6 | |
| 17. | | 10422.88 | | |
| 18. | 10736.0 | | | |
| 19. | | | 11065.2 | |
| 20. | | 11354.4 | | |
| 21. | 11667.6 | | | |
| 22. | | | 11996.8 | |
| 23. | | 12286.0 | | |
| 24. | 12599.2 | | | |
| 25. | | | 12928.4 | |
| 26. | | | | 13232.6 |

TABLE III-continued

| # | Col A | Col B | Col C | Col D |
|---|---|---|---|---|
| 27. |  | 13521.8 |  |  |
| 28. | 13835.0 |  |  |  |
| 29. |  | 14124.2 |  |  |
| 30. |  |  | 14453.4 |  |
| 31. |  | 14742.6 |  |  |
| 32. |  |  |  | 15046.8 |
| 33. | 15360.0 |  |  |  |
| 34. | 15673.2 |  |  |  |
| 35. |  | 15962.4 |  |  |
| 36. |  | 16251.6. |  |  |
| 37. |  |  | 16580.8 |  |
| 38. | 16894.0 |  |  |  |
| 39. | 17207.2 |  |  |  |
| 40. |  |  |  | 17511.4 |
| 41. |  | 17800.6 |  |  |
| 42. |  | 18189.8 |  |  |
| 43. |  | 18379.0 |  |  |
| 44. |  |  |  | 18683.2 |
| 45. |  |  | 19012.4 |  |
| 46. |  |  | 19341.6 |  |
| 47. |  |  |  | 19645.8 |
| 48. |  | 19935.0 |  |  |
| 49. | 20248.2 |  |  |  |
| 50. |  |  | 20577.4 |  |
| 51. | 20890.6 |  |  |  |
| 52. |  |  |  | 21194.4 |
| 53. |  | 21484.0 |  |  |
| 54. |  |  |  | 21788.2 |
| 55. |  |  |  | 22092.4 |

Sequencing Using Duplex DNA Probes for Capturing and Priming

Duplex DNA probes with single-stranded overhang have been demonstrated to be able to capture specific DNA templates and also served as primers for sold-state sequencing. The scheme is shown in FIG. 46. Stacking interactions between a duplex probe and a single-stranded template allow only 5-base overhang to be to be sufficient for capturing. Based on this format, a 5' fluorescent-labeled 23-mer (5'-GAT GAT CCG ACG CAT CAC AGC TC-3') (SEQ.ID.No. 29)) was annealed to a 3'-biotinylated 18-mer (5'-GTG ATG CCT CGG ATC ATC-3') (SEQ.ID.No. 30)), leaving a 5-base overhang. A 15-mer template (5'-TCG GTT CCA AGA GCT-3') (SEQ.ID.No. 31)) was captured by the duplex and sequencing reactions were performed by extension of the 5-base overhang. MALDI-TOF mass spectra of the reactions are shown in FIGS. 47A–D. All sequencing peaks were resolved, although at relatively low intensities. The last peak in each reaction is due to unspecific addition of one nucleotide to the full length extension product by the Sequenase enzyme. For comparison, the same products were run on a conventional DNA sequencer and a stacking fluorogram of the results is shown in FIGS. 48A–D. As can be seen from the Figures, the mass spectra had the same pattern as the fluorogram with sequencing peaks at much lower intensity compared to the 23-mer primer.

Improvements of MALDI-TOF Mass Spectrometry as a Dection Technique

Sample distribution can be made more homogenous and signal intensity could potentially be increased by implementing the picoliter vial technique. In practice, the samples can be loaded on small pits with square openings of 100 $\mu$m size. The beads used in the solid state sequencing are less than 10 $\mu$m in diameter, so they should fit well in the microliter vials. Microcrystals of matrix and DNA containing "sweet spots" will be confined in the vial. Since the laser spot size is about 100 $\mu$m in diameter, it will cover the entire opening of the vial. Therefore, searching for sweet spots will be unnecessary and high repetition-rate laser (e.g. $\leqslant$10 Hz) can be used for acquiring spectra. An earlier report has shown that this device is capable of increasing the detection sensitivity of peptides and proteins by several orders of magnitude compared to the conventional MALDI sample preparation technique.

Resolution of MALDI on DNA needs to be further improved in order to extend the sequencing range beyond 100 bases. Currently, using 3-HPA/ammonium citrate as matrix and a reflectron TOF mass spectrometer with 5 kV ion source and 20 kV postacceleration, the resolution of the run-through peak in FIG. 33A (73-mer) is greater than 200 (FWHM) which is enough for sequence determination in this case. This resolution is also the highest reported for MALDI desorbed DNA ions above the 70-mer range. Use of the delayed extraction technique may further enhance resolution.

All of the above-cited references, applications and publications are herein incorporated by reference.

Equivalents

Those skilled in the art will recognize, or, be able to ascertain using no more than routine experimentation, numerous equivalents to the specific procedures described herein. Such equivalents are considered to be within the scope of this invention and are covered by the following claims.

What is claimed is:

1. A process for detecting one or more target nucleic acid sequences in a biological sample, comprising:
   a) digesting nucleic acids from the sample;
   b) analyzing digested fragments by mass spectrometry;
   c) detecting a target nucleic acid sequence by a specific molecular weight, wherein detection of the target nucleic acid by mass spectrometry indicates the presence of the target nucleic acid sequence in the biological sample.

2. The process of claim 1, further comprising the step of amplifying nucleic acid molecules in the sample prior to analysis.

3. The process of claim 1, wherein the digested fragments are conditioned prior to mass spectrometric analysis.

4. The process of claim 1, wherein dection of a target nucleic acid sequence in the sample provides a genetic diagnosis, detects chromosomal aneuploidy, detects a genetic predisposition to a disease or condition, or detects or identifies infection by a pathogen.

5. The process of claim 1, wherein a plurality of nucleic acids from the sample are immobilized on a solid support prior to mass spectrometric analysis.

6. The method of claim 5, wherein the nucleic acids are in an array and each spot on the array is subjected to mass spectrometric analysis.

7. The process of claim 5, wherein immobilization is effected by a bond cleavable by a pyrophosphatase.

8. The process of claim 7, wherein immobilization is effected by a bond cleavable by pyrophosphatase.

9. The process of claim 1, herein a nucleic acid comprising the target sequence has been contacted with an alkylating agent prior to mass spectrometric analysis.

10. The process of claim 1, wherein a nucleic acid comprising the target sequence includes one or more of the following: nucleotides that reduce sensitivity for depurination, RNA building blocks, phosphorothioate groups, nucleic acid mimetics and protein nucleic acid (PNA).

11. The process of claim 10, wherein the target nucleic acid includes an alkylated phosphorothioate group.

12. A process for detecting one or more target nucleic acid sequences in a biological sample, comprising:

a) amplifying nucleic acids from the sample;
b) analyzing nucleic acids in the sample by mass spectrometry;
c) detecting a target nucleic acid sequence by a specific molecular weight, wherein detection of the target nucleic acid by mass spectrometry indicates the presence of the target nucleic acid sequence in the biological sample.

13. The process of claim 12, wherein nucleic acids are conditioned prior to mass spectrometric analysis.

14. The process of claim 12, wherein dection of a target nucleic acid sequence in the sample provides a genetic diagnosis, detects chromosomal aneuploidy, detects a genetic predisposition to a disease or condition, or detects or identifies infection by a pathogen.

15. The process of claim 12, wherein a plurality of nucleic acids from the sample are immobilized on a solid support prior to mass spectrometric analysis.

16. The process of claim 15, wherein immobilization is effected by a bond cleavable by a pyrophosphatase.

17. The process of claim 16, wherein immobilization is effected by a bond cleavable by pyrophosphatase.

18. The method of claim 12, wherein the nucleic acids are arranged in an array and each spot on the array is subjected to mass spectrometric analysis.

19. The process of claim 12, wherein a nucleic acid comprising the target sequence has been contacted with an alkylating agent prior to mass spectrometric analysis.

20. The process of claim 12, wherein a nucleic acid comprising the target sequence includes one or more of the following: nucleotides that reduce sensitivity for depurination, RNA building blocks, phosphorothioate groups, nucleic acid mimetics and protein nucleic acid (PNA).

21. The process of claim 12, wherein the target nucleic acid includes an alkylated phosphorothioate group.

* * * * *

UNITED STATES PATENT AND TRADEMARK OFFICE
CERTIFICATE OF CORRECTION

PATENT NO. : 6,500,621 B2
DATED : December 31, 2002
INVENTOR(S) : Hubert Köster

It is certified that error appears in the above-identified patent and that said Letters Patent is hereby corrected as shown below:

Column 1,
Line 47, please replace "Klienfelter's Syndrome" with -- Klinefelter's Syndrome --

Column 5,
Lines 26-27, please replace "educts" with -- products --

Column 8,
Line 45, please replace "indicats" with -- indicates --

Column 13,
Line 18, please replace "dithioerythritol" with -- dithiothreitol --
Line 60, please replace "volatization" with -- volatilization --

Column 16,
Line 1, please replace "n MALDI" with -- In MALDI --
Line 43, please replace "Klienfelter's" with -- Klinefelter's --

Column 22,
Line 39, please replace "MALDI-TOR" with -- MALDI-TOF --

Column 27,
Line 3, please replace "steptavidin" with -- streptavidin --

Column 58, line 66 through Column 59, line 8,
Please replace claim 12 with the following claim:

12. A process for detecting one or more target nucleic acid sequences in a biological sample, comprising:
        a) amplifying nucleic acids from the sample;
        b) analyzing nucleic acids from the sample by mass spectrometry;
        c) detecting a target nucleic acid sequence by a specific molecular weight, wherein detection of the target nucleic acid by mass spectrometry indicates the presence of the target nucleic acid sequence in the biological sample.

UNITED STATES PATENT AND TRADEMARK OFFICE
CERTIFICATE OF CORRECTION

PATENT NO. : 6,500,621 B2
DATED : December 31, 2002
INVENTOR(S) : Hubert Köster

It is certified that error appears in the above-identified patent and that said Letters Patent is hereby corrected as shown below:

<u>Column 59,</u>
Line 11, please replace claim 14 with the following claim:

14. The process of claim 14, wherein detection of a target nucleic acid sequence in the sample provides a genetic diagnosis, detects chromosomal aneuploidy, detects a genetic predisposition to a disease or condition, or detects or identifies infection by a pathogen.

Signed and Sealed this

Twenty-fifth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,500,621 B2
APPLICATION NO. : 09/796416
DATED : December 31, 2002
INVENTOR(S) : Hubert Köster It is certified that error appears in the above-identified patent and that said Letters Patent is hereby corrected as shown below:

IN THE SPECIFICATION:

Please amend the specification as follows:

at column 1, line 47, please replace "Klienfelter's Syndrome" with --Klinefelter's Syndrome-- at column 5, lines 26-27, please replace "educts" with --products-- at column 8, line 45, please replace "indicats" with --indicates-- at column 13, line 18, please replace "dithioerythritol" with --dithiothreitol-- at column 13 line 60, please replace "volatization" with --volatilization-- at column 16, line 1, Please replace "n MALDI" with In --In MALDI-- at column 16, line 43, please replace "Klienfelter's" with --Klinefelter's-- at column 22, line 39, please replace "MALDI-TOR" with --MALDI-TOF-- at column 27, line 3, please replace "steptavidin" with --streptavidin--

IN THE CLAIMS:

Please replace claim 12 with the following Claim:

--12. A process for detecting one or more target nucleic acid sequences in a biological sample, comprising:
    a) amplifying nucleic acids from the sample;
    b) analyzing nucleic acids from the sample by mass spectrometry;
    c) detecting a target nucleic acid sequence by a specific molecular weight, wherein detection of the target nucleic acid by mass spectrometry indicates the presence of the target nucleic acid sequence in the biological sample.

UNITED STATES PATENT AND TRADEMARK OFFICE
CERTIFICATE OF CORRECTION

PATENT NO.        : 6,500,621 B2
APPLICATION NO.   : 09/796416
DATED             : December 31, 2002
INVENTOR(S)       : Hubert Köster It is certified that error appears in the above-identified patent and that said Letters Patent is hereby corrected as shown below:

IN THE CLAIMS (cont'd):
Please replace claim 14 with the following claim:

14.    The process of claim 14, wherein detection of a target nucleic acid sequence in the sample provides a genetic diagnosis, detects chromosomal aneuploidy, detects a genetic predisposition to a disease or condition, or detects or identifies infection by a pathogen.--

Signed and Sealed this

First Day of May, 2007

JON W. DUDAS
*Director of the United States Patent and Trademark Office*